United States Patent
Herbowy et al.

(10) Patent No.: US 9,730,700 B2
(45) Date of Patent: Aug. 15, 2017

(54) STENT GRAFT DELIVERY SYSTEM

(71) Applicant: NELLIX, INC., Irvine, CA (US)

(72) Inventors: Steven L. Herbowy, Palo Alto, CA (US); Michael A. Evans, Palo Alto, CA (US); Anant Kumar, San Jose, CA (US); K. T. Venkateswara Rao, San Jose, CA (US); Matthew R. Hellewell, Menlo Park, CA (US); Gil Laroya, Santa Clara, CA (US)

(73) Assignee: Nellix, Inc., Irvine, CA (US)

( * ) Notice: Subject to any disclaimer, the term of this patent is extended or adjusted under 35 U.S.C. 154(b) by 0 days.

(21) Appl. No.: 14/586,110

(22) Filed: Apr. 23, 2015

(65) Prior Publication Data
US 2015/0216535 A1    Aug. 6, 2015

Related U.S. Application Data

(60) Continuation of application No. 13/243,941, filed on Sep. 23, 2011, now Pat. No. 8,926,682, which is a (Continued)

(51) Int. Cl.
*A61B 17/12* (2006.01)
*A61M 25/10* (2013.01)
(Continued)

(52) U.S. Cl.
CPC .. *A61B 17/12118* (2013.01); *A61B 17/12136* (2013.01); *A61B 17/12186* (2013.01); (Continued)

(58) Field of Classification Search
CPC .............. A61F 2/954; A61F 2002/077; A61B 17/12118; A61B 17/12195
See application file for complete search history.

(56) References Cited

U.S. PATENT DOCUMENTS 4,565,738 A    1/1986 Purdy
4,638,803 A    1/1987 Rand
(Continued)

FOREIGN PATENT DOCUMENTS

DE    4010975 A1    10/1991
EP    0679372 A2    11/1995
(Continued)

OTHER PUBLICATIONS

Carmi et al., "Endovascular stent-graft adapted to the endoluminal environment: prototype of a new endoluminal approach," J Endovasc Ther. Jun. 2002;9(3):380-381.
(Continued)

*Primary Examiner* — Thomas McEvoy
(74) *Attorney, Agent, or Firm* — Kilpatrick, Townsend & Stockton, LLP

(57) ABSTRACT

A system for treating an aneurysm comprises an elongate flexible shaft and an expandable member. An expandable scaffold is disposed over the expandable member and may be expanded from a collapsed configuration to an expanded configuration. A double-walled filling structure is disposed over the scaffold and has an outer wall and an inner wall. The filling structure is adapted to be filled with a hardenable fluid filing medium so that the outer wall conforms to an inside surface of the aneurysm and the inner wall forms a substantially tubular lumen to provide a path for blood flow. In the expanded configuration the scaffold engages the inner wall of the filling structure. A tether is releasably coupled with the filling structure and the flexible shaft thereby constraining axial movement of the structures relative to each other.

21 Claims, 47 Drawing Sheets

Related U.S. Application Data division of application No. 12/429,474, filed on Apr. 24, 2009, now abandoned.

(60) Provisional application No. 61/048,038, filed on Apr. 25, 2008.

(51) Int. Cl.
| | | |
|---|---|---|
| *A61F 2/07* | (2013.01) | |
| *A61F 2/954* | (2013.01) | |
| *A61F 2/90* | (2013.01) | |
| A61F 2/06 | (2013.01) | |
| A61F 2/30 | (2006.01) | |
| A61F 2/95 | (2013.01) | |
| A61M 25/00 | (2006.01) | |

(52) U.S. Cl.
CPC .......... *A61B 17/12195* (2013.01); *A61F 2/07* (2013.01); *A61F 2/90* (2013.01); *A61F 2/954* (2013.01); *A61M 25/10182* (2013.11); *A61M 25/10187* (2013.11); A61F 2002/067 (2013.01); A61F 2002/077 (2013.01); A61F 2002/30583 (2013.01); A61F 2002/30604 (2013.01); A61F 2002/9511 (2013.01); A61F 2210/0085 (2013.01); A61F 2230/0034 (2013.01); A61F 2250/0003 (2013.01); A61F 2250/006 (2013.01); A61M 25/007 (2013.01); A61M 25/1018 (2013.01)

(56) References Cited

U.S. PATENT DOCUMENTS

| | | |
|---|---|---|
| 4,641,653 A | 2/1987 | Rockey |
| 4,704,126 A | 11/1987 | Baswell |
| 4,710,192 A | 12/1987 | Liotta |
| 4,728,328 A | 3/1988 | Hughes et al. |
| 4,731,073 A | 3/1988 | Robinson |
| 4,733,665 A | 3/1988 | Palmaz |
| 4,743,258 A | 5/1988 | Ikada |
| 4,763,654 A | 8/1988 | Jang |
| 4,856,516 A | 8/1989 | Hillstead |
| 4,858,264 A | 8/1989 | Reinhart |
| 4,892,544 A | 1/1990 | Frisch |
| 4,976,692 A | 12/1990 | Atad |
| 5,002,532 A | 3/1991 | Gaiser |
| 5,074,845 A | 12/1991 | Miraki |
| 5,104,404 A | 4/1992 | Wolff |
| 5,108,417 A | 4/1992 | Sawyer |
| 5,122,154 A | 6/1992 | Rhodes |
| 5,133,732 A | 7/1992 | Wiktor |
| 5,139,480 A | 8/1992 | Hickle |
| 5,156,620 A | 10/1992 | Pigott |
| 5,195,984 A | 3/1993 | Schatz |
| 5,217,484 A | 6/1993 | Marks |
| 5,222,970 A | 6/1993 | Reeves |
| 5,234,437 A | 8/1993 | Sepetka |
| 5,242,399 A | 9/1993 | Lau |
| 5,250,071 A | 10/1993 | Palermo |
| 5,261,916 A | 11/1993 | Engelson |
| 5,263,964 A | 11/1993 | Purdy |
| 5,292,331 A | 3/1994 | Boneau |
| 5,314,444 A | 5/1994 | Gianturco |
| 5,316,023 A | 5/1994 | Palmaz et al. |
| 5,330,528 A | 7/1994 | Lazim |
| 5,334,024 A | 8/1994 | Niznick |
| 5,334,217 A | 8/1994 | Das |
| 5,350,397 A | 9/1994 | Palermo |
| 5,352,199 A | 10/1994 | Tower |
| 5,375,612 A | 12/1994 | Cottenceau |
| 5,383,892 A | 1/1995 | Cardon |
| 5,421,955 A | 6/1995 | Lau |
| 5,423,849 A | 6/1995 | Engelson |
| 5,425,739 A | 6/1995 | Jessen |
| 5,425,744 A | 6/1995 | Fagan |
| 5,441,510 A | 8/1995 | Simpson |
| 5,441,515 A | 8/1995 | Khosravi |
| 5,443,477 A | 8/1995 | Marin |
| 5,443,496 A | 8/1995 | Schwartz |
| 5,449,373 A | 9/1995 | Pinchasik |
| 5,485,667 A | 1/1996 | Kleshinski |
| 5,494,029 A | 2/1996 | Lane |
| 5,496,277 A | 3/1996 | Termin |
| 5,507,767 A | 4/1996 | Maeda |
| 5,507,769 A | 4/1996 | Marin et al. |
| 5,507,771 A | 4/1996 | Gianturco |
| 5,514,115 A | 5/1996 | Frantzen |
| 5,514,154 A | 5/1996 | Lau |
| 5,522,882 A | 6/1996 | Gaterud |
| 5,531,741 A | 7/1996 | Barbacci |
| 5,534,024 A | 7/1996 | Rogers et al. |
| 5,545,210 A | 8/1996 | Hess |
| 5,549,662 A | 8/1996 | Fordenbacher |
| 5,549,663 A | 8/1996 | Cottone, Jr. |
| 5,554,181 A | 9/1996 | Das |
| 5,562,641 A | 10/1996 | Flomenblit |
| 5,562,698 A | 10/1996 | Parker |
| 5,562,728 A | 10/1996 | Lazarus |
| 5,569,295 A | 10/1996 | Lam |
| 5,578,074 A | 11/1996 | Mirigian |
| 5,578,149 A | 11/1996 | De Scheerder |
| 5,591,195 A | 1/1997 | Taheri |
| 5,591,223 A | 1/1997 | Lock |
| 5,591,226 A | 1/1997 | Trerotola |
| 5,591,228 A | 1/1997 | Edoga |
| 5,591,230 A | 1/1997 | Horn |
| 5,593,417 A | 1/1997 | Rhodes |
| 5,601,600 A | 2/1997 | Ton |
| 5,603,721 A | 2/1997 | Lau |
| 5,605,530 A | 2/1997 | Fischell |
| 5,607,442 A | 3/1997 | Fischell |
| 5,607,445 A | 3/1997 | Summers |
| 5,607,468 A | 3/1997 | Rogers |
| 5,609,605 A | 3/1997 | Marshall |
| 5,617,878 A | 4/1997 | Taheri |
| 5,618,299 A | 4/1997 | Khosravi |
| 5,624,411 A | 4/1997 | Tuch |
| 5,630,840 A | 5/1997 | Mayer |
| 5,632,760 A | 5/1997 | Sheiban |
| 5,632,762 A | 5/1997 | Myler |
| 5,632,763 A | 5/1997 | Glastra |
| 5,632,771 A | 5/1997 | Boatman |
| D380,266 S | 6/1997 | Boatman |
| 5,634,941 A | 6/1997 | Winston |
| 5,636,641 A | 6/1997 | Fariabi |
| D380,831 S | 7/1997 | Kavteladze |
| 5,662,614 A | 9/1997 | Edoga |
| 5,665,117 A | 9/1997 | Rhodes |
| 5,674,241 A | 10/1997 | Bley |
| 5,676,697 A | 10/1997 | McDonald |
| 5,683,449 A | 11/1997 | Marcade |
| 5,690,643 A | 11/1997 | WiJay |
| 5,693,038 A | 12/1997 | Suzuki et al. |
| 5,693,067 A | 12/1997 | Purdy |
| 5,693,088 A | 12/1997 | Lazarus |
| 5,697,971 A | 12/1997 | Fischell |
| 5,709,707 A | 1/1998 | Lock |
| 5,718,713 A | 2/1998 | Frantzen |
| 5,723,004 A | 3/1998 | Dereume |
| 5,725,568 A | 3/1998 | Hastings |
| 5,725,572 A | 3/1998 | Lam |
| 5,728,068 A | 3/1998 | Leone |
| 5,728,131 A | 3/1998 | Frantzen |
| 5,728,158 A | 3/1998 | Lau |
| 5,733,303 A | 3/1998 | Israel et al. |
| 5,735,892 A | 4/1998 | Myers |
| 5,735,893 A | 4/1998 | Lau |
| 5,741,327 A | 4/1998 | Frantzen |
| 5,741,333 A | 4/1998 | Frid |
| 5,746,691 A | 5/1998 | Frantzen |
| 5,755,769 A | 5/1998 | Richard |
| 5,755,773 A | 5/1998 | Evans et al. |
| 5,755,778 A | 5/1998 | Kleshinski |

(56) References Cited

U.S. PATENT DOCUMENTS

| | | |
|---|---|---|
| 5,766,151 A | 6/1998 | Valley et al. |
| 5,766,238 A | 6/1998 | Lau |
| 5,769,882 A | 6/1998 | Fogarty et al. |
| 5,776,114 A | 7/1998 | Frantzen |
| 5,776,161 A | 7/1998 | Globerman |
| 5,782,907 A | 7/1998 | Frantzen |
| 5,785,679 A | 7/1998 | Abolfathi et al. |
| 5,788,626 A | 8/1998 | Thompson |
| 5,797,953 A | 8/1998 | Tekulve |
| 5,800,393 A | 9/1998 | Sahota |
| 5,800,512 A | 9/1998 | Lentz et al. |
| 5,800,514 A | 9/1998 | Nunez |
| 5,800,525 A | 9/1998 | Bachinski |
| 5,807,404 A | 9/1998 | Richter |
| 5,810,872 A | 9/1998 | Kanesaka |
| 5,824,036 A | 10/1998 | Lauterjung |
| 5,824,037 A | 10/1998 | Fogarty et al. |
| 5,824,040 A | 10/1998 | Cox |
| 5,824,049 A | 10/1998 | Ragheb |
| 5,824,054 A | 10/1998 | Khosravi et al. |
| 5,824,056 A | 10/1998 | Rosenberg |
| 5,827,321 A | 10/1998 | Roubin |
| 5,836,966 A | 11/1998 | St. Germain |
| 5,843,160 A | 12/1998 | Rhodes |
| 5,843,175 A | 12/1998 | Frantzen |
| 5,846,246 A | 12/1998 | Dirks |
| 5,846,261 A | 12/1998 | Kotula et al. |
| 5,849,037 A | 12/1998 | Frid |
| 5,860,998 A | 1/1999 | Robinson |
| 5,863,627 A | 1/1999 | Szycher |
| 5,867,762 A | 2/1999 | Rafferty et al. |
| 5,868,685 A | 2/1999 | Powell et al. |
| 5,868,708 A | 2/1999 | Hart |
| 5,868,782 A | 2/1999 | Frantzen |
| 5,871,537 A | 2/1999 | Holman |
| 5,873,907 A | 2/1999 | Frantzen |
| 5,876,448 A | 3/1999 | Thompson et al. |
| 5,879,381 A | 3/1999 | Moriuchi |
| 5,888,660 A | 3/1999 | Landoni et al. |
| 5,902,332 A | 5/1999 | Schatz |
| 5,919,224 A | 7/1999 | Thompson |
| 5,928,279 A | 7/1999 | Shannon et al. |
| 5,931,866 A | 8/1999 | Frantzen |
| 5,944,750 A | 8/1999 | Tanner |
| 5,947,991 A | 9/1999 | Cowan |
| 5,948,184 A | 9/1999 | Frantzen |
| 5,976,178 A | 11/1999 | Goldsteen et al. |
| 5,984,955 A | 11/1999 | Wisselink |
| 5,994,750 A | 11/1999 | Yagi |
| 6,007,573 A | 12/1999 | Wallace |
| 6,015,431 A | 1/2000 | Thornton |
| 6,022,359 A | 2/2000 | Frantzen |
| 6,033,434 A | 3/2000 | Borghi |
| 6,042,606 A | 3/2000 | Frantzen |
| 6,056,776 A | 5/2000 | Lau |
| 6,066,167 A | 5/2000 | Lau |
| 6,066,168 A | 5/2000 | Lau |
| 6,083,259 A | 7/2000 | Frantzen |
| 6,093,199 A | 7/2000 | Brown |
| 6,099,548 A | 8/2000 | Taheri |
| 6,110,198 A | 8/2000 | Fogarty et al. |
| 6,123,715 A | 9/2000 | Amplatz |
| 6,123,722 A | 9/2000 | Fogarty |
| 6,124,523 A | 9/2000 | Banas et al. |
| 6,132,457 A | 10/2000 | Chobotov |
| 6,152,144 A | 11/2000 | Lesh |
| 6,152,943 A | 11/2000 | Sawhney |
| 6,168,592 B1 | 1/2001 | Kupiecki et al. |
| 6,187,033 B1 | 2/2001 | Schmitt |
| 6,187,034 B1 | 2/2001 | Frantzen |
| 6,190,402 B1 | 2/2001 | Horton et al. |
| 6,190,406 B1 | 2/2001 | Duerig et al. |
| 6,193,745 B1 | 2/2001 | Fogarty et al. |
| 6,196,230 B1 | 3/2001 | Hall et al. |
| 6,203,732 B1 | 3/2001 | Clubb |
| 6,214,022 B1 | 4/2001 | Taylor et al. |
| 6,231,562 B1 | 5/2001 | Khosravi et al. |
| 6,235,050 B1 | 5/2001 | Quiachon et al. |
| 6,241,761 B1 | 6/2001 | Villafana |
| 6,254,633 B1 | 7/2001 | Pinchuk et al. |
| 6,261,305 B1 | 7/2001 | Marotta et al. |
| 6,280,466 B1 | 8/2001 | Kugler |
| 6,283,991 B1 | 9/2001 | Cox et al. |
| 6,290,722 B1 | 9/2001 | Wang |
| 6,290,731 B1 | 9/2001 | Solovay et al. |
| 6,293,960 B1 | 9/2001 | Ken |
| 6,296,603 B1 | 10/2001 | Turnlund et al. |
| 6,299,597 B1 | 10/2001 | Buscemi et al. |
| 6,299,604 B1 | 10/2001 | Ragheb |
| 6,312,462 B1 | 11/2001 | McDermott et al. |
| 6,312,463 B1 | 11/2001 | Rourke et al. |
| 6,325,816 B1 | 12/2001 | Fulton, III |
| 6,325,819 B1 | 12/2001 | Pavcnik et al. |
| 6,331,184 B1 | 12/2001 | Abrams |
| 6,331,191 B1 | 12/2001 | Chobotov |
| 6,334,869 B1 | 1/2002 | Leonhardt et al. |
| 6,344,056 B1 | 2/2002 | Dehdashtian |
| 6,375,675 B2 | 4/2002 | Dehdashtian et al. |
| 6,395,019 B2 * | 5/2002 | Chobotov ............... A61F 2/07 606/198 |
| 6,409,757 B1 | 6/2002 | Trout, III et al. |
| 6,432,131 B1 | 8/2002 | Ravenscroft |
| 6,451,047 B2 | 9/2002 | McCrea |
| 6,463,317 B1 | 10/2002 | Kucharczyk et al. |
| 6,506,204 B2 | 1/2003 | Mazzocchi |
| 6,527,799 B2 | 3/2003 | Shanley |
| 6,544,276 B1 | 4/2003 | Azizi |
| 6,547,804 B2 | 4/2003 | Porter et al. |
| 6,554,858 B2 | 4/2003 | Dereume et al. |
| 6,576,007 B2 | 6/2003 | Dehdashtian et al. |
| 6,579,301 B1 | 6/2003 | Bales |
| 6,592,614 B2 | 7/2003 | Lenker et al. |
| 6,602,280 B2 * | 8/2003 | Chobotov ............... A61F 2/07 606/108 |
| 6,613,037 B2 | 9/2003 | Khosravi et al. |
| 6,645,242 B1 | 11/2003 | Quinn |
| 6,656,214 B1 | 12/2003 | Fogarty et al. |
| 6,656,220 B1 | 12/2003 | Gomez et al. |
| 6,663,607 B2 | 12/2003 | Slaikeu et al. |
| 6,663,667 B2 | 12/2003 | Dehdashtian et al. |
| 6,679,300 B1 | 1/2004 | Sommer et al. |
| 6,682,546 B2 | 1/2004 | Amplatz |
| 6,692,486 B2 | 2/2004 | Jaafar et al. |
| 6,695,833 B1 | 2/2004 | Frantzen |
| 6,729,356 B1 | 5/2004 | Baker et al. |
| 6,730,119 B1 | 5/2004 | Smalling |
| 6,733,521 B2 | 5/2004 | Chobotov |
| 6,761,733 B2 | 7/2004 | Chobotov |
| 6,773,454 B2 | 8/2004 | Wholey et al. |
| 6,776,771 B2 | 8/2004 | Van Moorlegem et al. |
| 6,827,735 B2 | 12/2004 | Greenberg |
| 6,843,803 B2 | 1/2005 | Ryan et al. |
| 6,878,161 B2 | 4/2005 | Lenker |
| 6,878,164 B2 | 4/2005 | Kujawski |
| 6,887,268 B2 | 5/2005 | Butaric et al. |
| 6,918,926 B2 | 7/2005 | Letort |
| 6,945,989 B1 | 9/2005 | Betelia et al. |
| 6,958,051 B2 | 10/2005 | Hart et al. |
| 6,960,227 B2 | 11/2005 | Jones et al. |
| 6,964,667 B2 | 11/2005 | Shaolian et al. |
| 7,001,431 B2 | 2/2006 | Bao et al. |
| 7,022,100 B1 | 4/2006 | Aboul-Hosn et al. |
| 7,105,012 B2 | 9/2006 | Trout, III |
| 7,112,217 B1 | 9/2006 | Kugler |
| 7,122,052 B2 | 10/2006 | Greenhalgh |
| 7,131,991 B2 | 11/2006 | Zarins et al. |
| 7,147,661 B2 | 12/2006 | Chobotov et al. |
| 7,175,651 B2 | 2/2007 | Kerr |
| 7,229,472 B2 | 6/2007 | DePalma et al. |
| 7,314,483 B2 | 1/2008 | Landau et al. |
| 7,326,237 B2 | 2/2008 | Depalma et al. |
| 7,435,253 B1 | 10/2008 | Hartley et al. |
| 7,530,988 B2 | 5/2009 | Evans et al. |
| 7,666,220 B2 | 2/2010 | Evans et al. |

(56) References Cited

U.S. PATENT DOCUMENTS

| | | |
|---|---|---|
| 7,682,383 B2 | 3/2010 | Robin |
| 7,708,773 B2 | 5/2010 | Pinchuk et al. |
| 7,790,273 B2 | 9/2010 | Lee et al. |
| 7,828,838 B2 | 11/2010 | Bolduc et al. |
| 7,872,068 B2 | 1/2011 | Khosravi et al. |
| 7,951,448 B2 | 5/2011 | Lee et al. |
| 8,044,137 B2 | 10/2011 | Khosravi et al. |
| 8,048,145 B2 | 11/2011 | Evans et al. |
| 8,182,525 B2 | 5/2012 | Herbowy et al. |
| 2001/0020184 A1 | 9/2001 | Dehdashtian et al. |
| 2001/0027337 A1 | 10/2001 | DiCaprio |
| 2001/0027338 A1 | 10/2001 | Greenberg |
| 2001/0044655 A1 | 11/2001 | Patnaik et al. |
| 2002/0019665 A1 | 2/2002 | Dehdashtian et al. |
| 2002/0026217 A1 | 2/2002 | Baker et al. |
| 2002/0045848 A1 | 4/2002 | Jaafar et al. |
| 2002/0045931 A1 | 4/2002 | Sogard et al. |
| 2002/0052643 A1 | 5/2002 | Wholey et al. |
| 2002/0077594 A1 | 6/2002 | Chien et al. |
| 2002/0151953 A1 | 10/2002 | Chobotov |
| 2002/0151956 A1 | 10/2002 | Chobotov |
| 2002/0151958 A1 | 10/2002 | Chuter |
| 2002/0156518 A1 | 10/2002 | Tehrani |
| 2002/0165521 A1 | 11/2002 | Cioanta et al. |
| 2002/0169497 A1 | 11/2002 | Wholey et al. |
| 2002/0183629 A1 | 12/2002 | Fitz |
| 2003/0004560 A1 | 1/2003 | Chobotov |
| 2003/0009132 A1 | 1/2003 | Schwartz et al. |
| 2003/0014075 A1 | 1/2003 | Rosenbluth et al. |
| 2003/0028209 A1 | 2/2003 | Teoh et al. |
| 2003/0036745 A1 | 2/2003 | Khosravi et al. |
| 2003/0051735 A1 | 3/2003 | Pavcnik et al. |
| 2003/0074056 A1 | 4/2003 | Killion et al. |
| 2003/0078647 A1 | 4/2003 | Vallana et al. |
| 2003/0093145 A1 | 5/2003 | Lawrence-Brown et al. |
| 2003/0130720 A1 | 7/2003 | DePalma et al. |
| 2003/0130725 A1 | 7/2003 | DePalma et al. |
| 2003/0135269 A1 | 7/2003 | Swanstrom |
| 2003/0204242 A1 | 10/2003 | Zarins et al. |
| 2003/0204249 A1 | 10/2003 | Letort |
| 2003/0216802 A1 | 11/2003 | Chobotov et al. |
| 2003/0225446 A1 | 12/2003 | Hartley |
| 2004/0016997 A1 | 1/2004 | Ushio |
| 2004/0044358 A1 | 3/2004 | Khosravi et al. |
| 2004/0082989 A1 | 4/2004 | Cook et al. |
| 2004/0091543 A1 | 5/2004 | Bell et al. |
| 2004/0098096 A1 | 5/2004 | Eton |
| 2004/0116997 A1 | 6/2004 | Taylor et al. |
| 2004/0147811 A1 | 7/2004 | Diederich et al. |
| 2004/0153025 A1 | 8/2004 | Seifert et al. |
| 2004/0167607 A1 | 8/2004 | Frantzen |
| 2004/0193245 A1 | 9/2004 | Deem et al. |
| 2004/0204755 A1 | 10/2004 | Robin |
| 2004/0215172 A1 | 10/2004 | Chu et al. |
| 2004/0215316 A1 | 10/2004 | Smalling |
| 2004/0220522 A1 | 11/2004 | Briscoe et al. |
| 2004/0243057 A1 | 12/2004 | Vinten-Johansen et al. |
| 2005/0004660 A1 | 1/2005 | Rosenbluth et al. |
| 2005/0027238 A1 | 2/2005 | Fago et al. |
| 2005/0028484 A1 | 2/2005 | Littlewood |
| 2005/0065592 A1 | 3/2005 | Holzer |
| 2005/0090804 A1 | 4/2005 | Chobotov et al. |
| 2005/0096731 A1 | 5/2005 | Looi et al. |
| 2005/0215989 A1 | 9/2005 | Abboud et al. |
| 2005/0245891 A1 | 11/2005 | McCormick et al. |
| 2005/0251251 A1 | 11/2005 | Cribier |
| 2006/0015173 A1 | 1/2006 | Clifford et al. |
| 2006/0025853 A1 | 2/2006 | Evans et al. |
| 2006/0074481 A1* | 4/2006 | Vardi ............ A61F 2/07 623/1.36 |
| 2006/0135942 A1 | 6/2006 | Fernandes et al. |
| 2006/0142836 A1 | 6/2006 | Hartley et al. |
| 2006/0155369 A1 | 7/2006 | Edwin et al. |
| 2006/0161244 A1 | 7/2006 | Seguin |
| 2006/0184109 A1 | 8/2006 | Gobel |
| 2006/0206197 A1 | 9/2006 | Morsi |
| 2006/0222596 A1 | 10/2006 | Askari et al. |
| 2006/0265043 A1 | 11/2006 | Mandrusov et al. |
| 2006/0292206 A1 | 12/2006 | Kim et al. |
| 2007/0032850 A1 | 2/2007 | Ruiz et al. |
| 2007/0043420 A1 | 2/2007 | Lostetter |
| 2007/0050008 A1 | 3/2007 | Kim et al. |
| 2007/0055355 A1 | 3/2007 | Kim et al. |
| 2007/0061005 A1 | 3/2007 | Kim et al. |
| 2007/0150041 A1 | 6/2007 | Evans et al. |
| 2007/0162109 A1 | 7/2007 | Davila et al. |
| 2007/0208416 A1 | 9/2007 | Burpee et al. |
| 2007/0276477 A1 | 11/2007 | Lee et al. |
| 2008/0039923 A1 | 2/2008 | Taylor et al. |
| 2008/0154368 A1 | 6/2008 | Justis et al. |
| 2008/0228259 A1 | 9/2008 | Chu |
| 2008/0294237 A1 | 11/2008 | Chu |
| 2009/0099649 A1 | 4/2009 | Chobotov et al. |
| 2009/0209855 A1 | 8/2009 | Drilling et al. |
| 2009/0216125 A1 | 8/2009 | Lenker |
| 2009/0318949 A1 | 12/2009 | Ganpath et al. |
| 2009/0319029 A1 | 12/2009 | Evans et al. |
| 2010/0004728 A1 | 1/2010 | Rao et al. |
| 2010/0036360 A1 | 2/2010 | Herbowy et al. |
| 2010/0106087 A1 | 4/2010 | Evans et al. |
| 2010/0217383 A1 | 8/2010 | Leonhardt et al. |
| 2012/0016456 A1 | 1/2012 | Herbowy et al. |
| 2012/0046684 A1 | 2/2012 | Evans et al. |

FOREIGN PATENT DOCUMENTS

| | | |
|---|---|---|
| EP | 1325717 A2 | 7/2003 |
| EP | 1903985 | 4/2008 |
| FR | 2834199 A1 | 7/2003 |
| JP | H04-322665 A | 11/1992 |
| JP | 2003-525692 A | 9/2003 |
| JP | 2004-537353 A | 12/2004 |
| JP | 2005-505380 A | 2/2005 |
| JP | 2005-532120 A | 10/2005 |
| JP | 2008-510502 A | 4/2008 |
| WO | 97/17912 A1 | 5/1997 |
| WO | 97/19653 A1 | 6/1997 |
| WO | 98/53761 A1 | 12/1998 |
| WO | 99/00073 A1 | 1/1999 |
| WO | 99/44539 A2 | 9/1999 |
| WO | 00/29060 A2 | 5/2000 |
| WO | 00/51522 A1 | 9/2000 |
| WO | 01/21108 A1 | 3/2001 |
| WO | 01/66038 A2 | 9/2001 |
| WO | 02/078569 A2 | 10/2002 |
| WO | 02/083038 A2 | 10/2002 |
| WO | 02/102282 A1 | 12/2002 |
| WO | 03/007785 A2 | 1/2003 |
| WO | 03/032869 A1 | 4/2003 |
| WO | 03/037222 A2 | 5/2003 |
| WO | 03/053288 A1 | 7/2003 |
| WO | 2004/004603 A1 | 1/2004 |
| WO | 2004/026183 A2 | 4/2004 |
| WO | 2004/037116 A2 | 5/2004 |
| WO | 2004/045393 A2 | 6/2004 |
| WO | 2006/012567 A2 | 2/2006 |
| WO | 2006/116725 A2 | 11/2006 |
| WO | 2007/008600 A2 | 1/2007 |
| WO | 2007/142916 A2 | 12/2007 |

OTHER PUBLICATIONS

Donayre et al., "Fillable Endovascular Aneurysm Repair," Endovascular Today, pp. 64-66, Jan. 2009.

Gilling-Smith, "Stent Graft Migration After Endovascular Aneurysm Repair," presented at 25th International Charing Cross Symposium, Apr. 13, 2003 [Power Point Presentation and Transcript], 56 pages total.

Journal of Endovascular Therapy; Apr. 2000; pp. 111, 114, 132-140; vol. 7' No. 2; International Society of Endovascular Specialists; Phoenix, AZ.

(56) References Cited

OTHER PUBLICATIONS

Patrick W. Serruys and Michael JB Kutryk; Handbook of Coronary Stents, Second Edition; 1998; pp. 45, 55, 78, 103, 112, 132, 158, 174, 185, 190, 207, 215, 230, 239; Martin Dunitz; UK.
Shan-e-ali Haider et al. Sac behavior after aneurysm treatment with the Gore Excluder low-permeability aortic endoprosthesis: 12-month comparison to the original Excluder device. Journal of Vascular Surgery. vol. 44, No. 4. 694-700. Oct. 2006.
Susan M. Trocciola et al. The development of endotension is associated with increased transmission of pressure and serous components in porous expanded polytetrafluoroethylene stent-grafts: Characterization using a canine model. Journal of Vascular Surgery. Jan. 2006. p. 109-116.
William Tanski, Mark Fillinger. Outcomes of original and low-permeability Gore Excluder endoprosthesis for endovascular abdominal aortic aneurysm repair. Journal of Vascular Surgery. Feb. 2007. p. 243-249.
U.S. Appl. No. 60/855,889, filed Oct. 31, 2006; first named inventor: Steven L. Herbowy.
U.S. Appl. No. 61/052,059, filed May 9, 2008; first named inventor: Gwendolyn A. Watanabe.
Examination Report of Japanese Patent Application No. 2011-506487, dated Jun. 11, 2013, 7 pages.
Examination report of European Application No. 09733719.0 dated Nov. 7, 2013, 6 pages.
Examination report of European Application No. 06751879.5, dated Mar. 24, 2014. 5 pages.
Examination Report of Japanese Patent Application No. 2011-506487, dated May 7, 2014, 7 pages.

\* cited by examiner

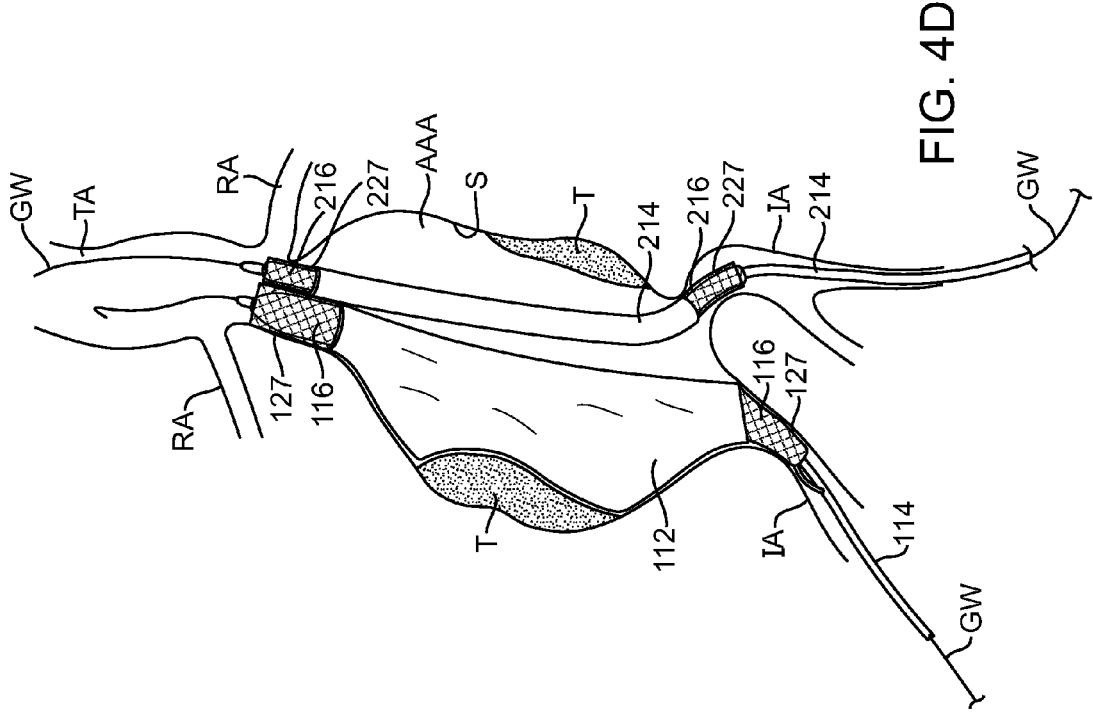
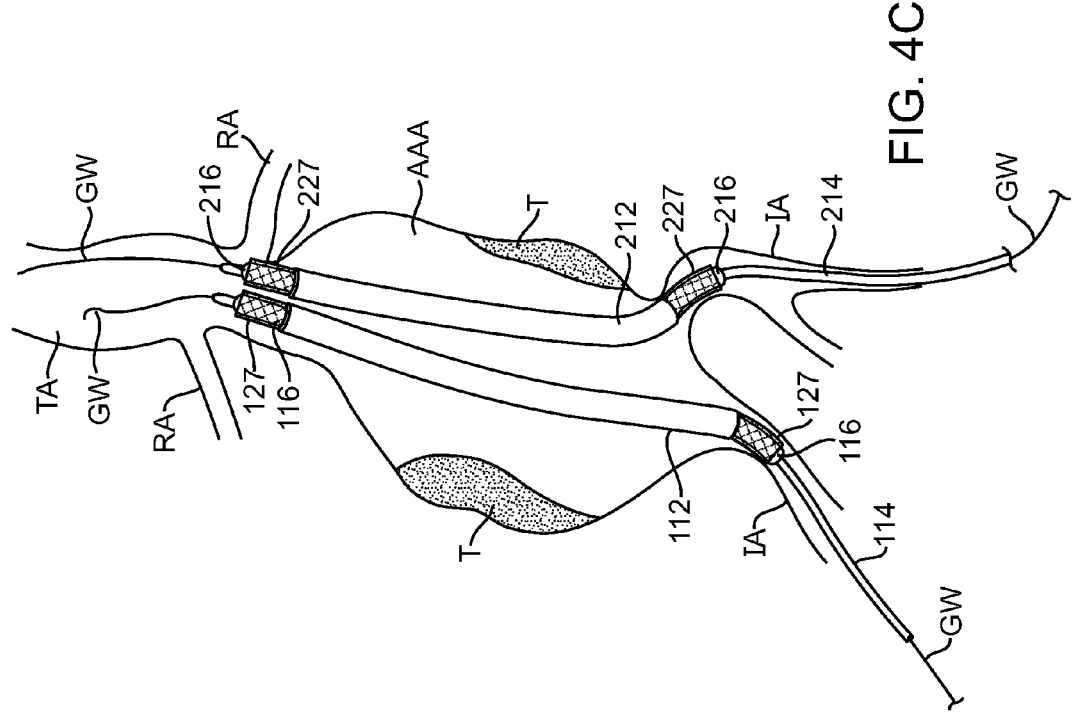

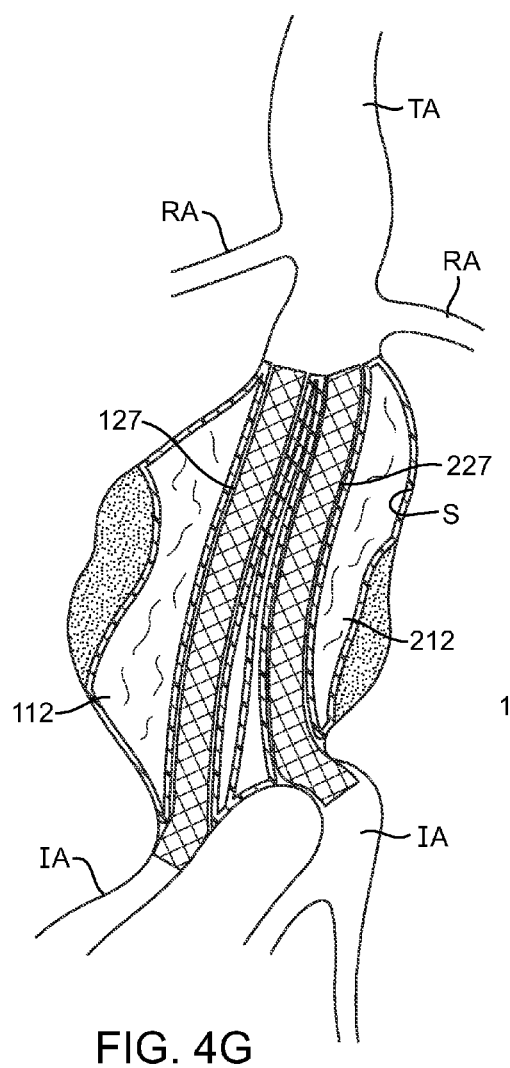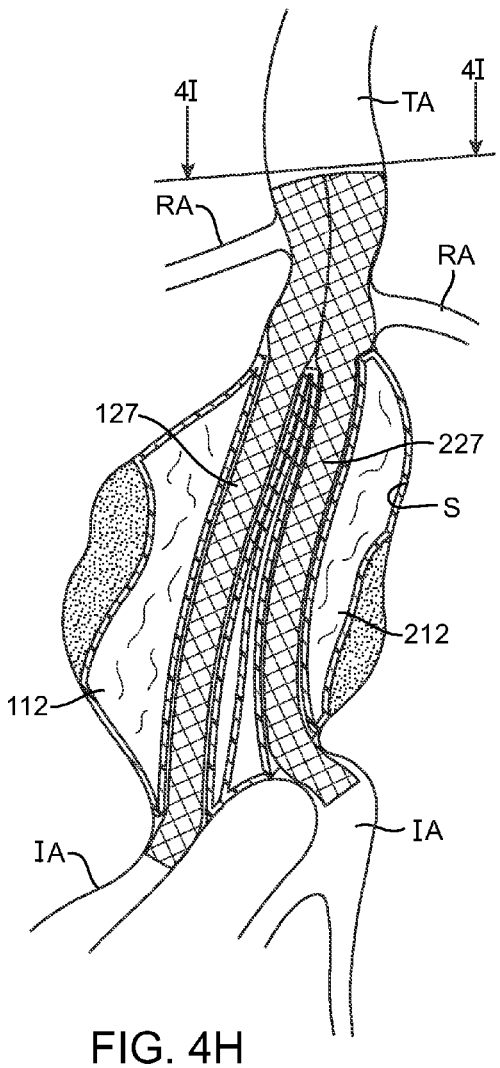
FIG. 4G  FIG. 4H
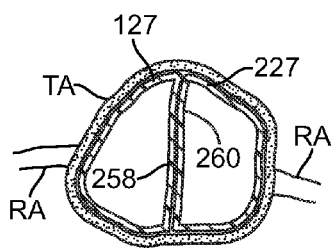
FIG. 4I

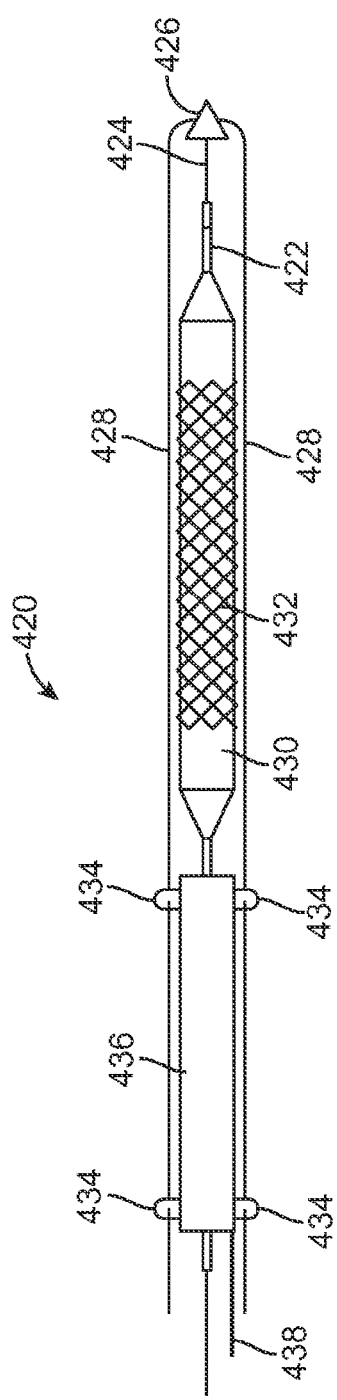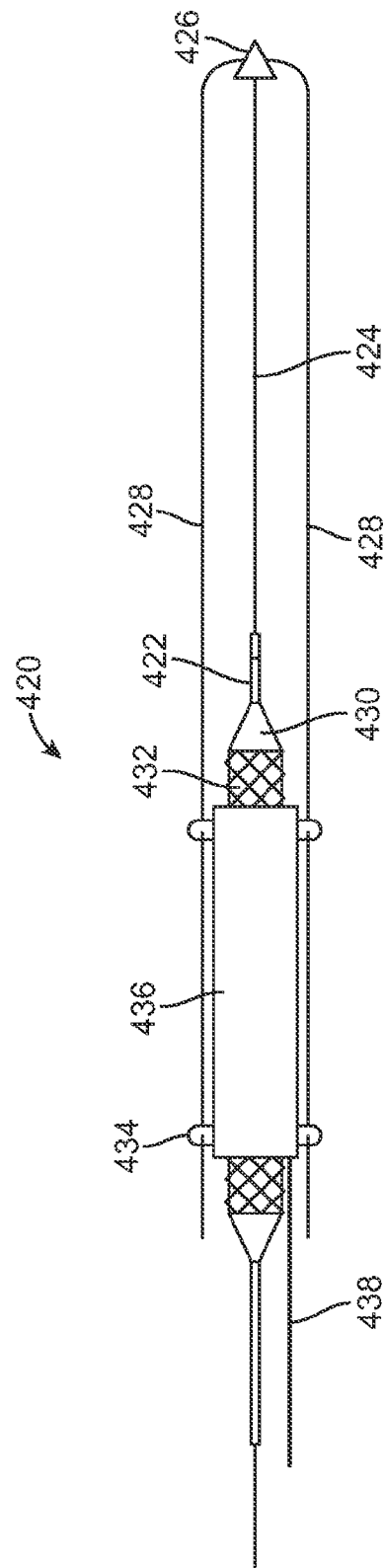
FIG. 11A
FIG. 11B

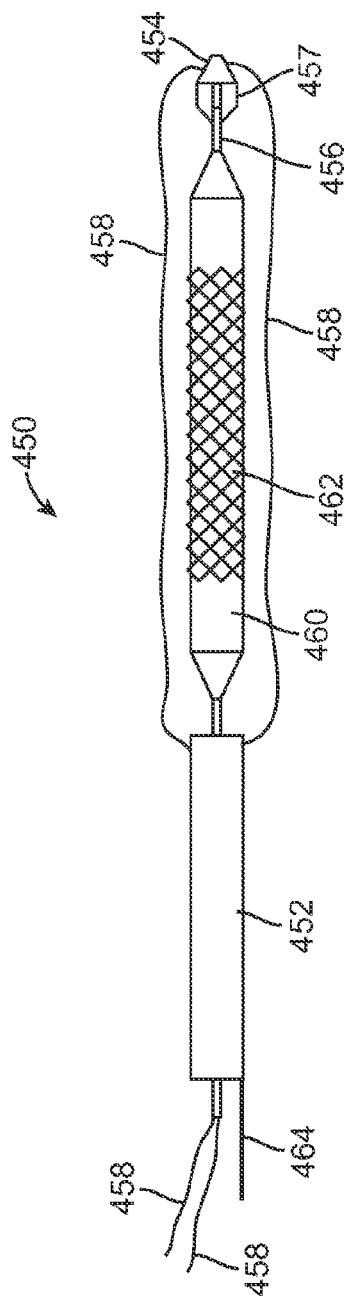
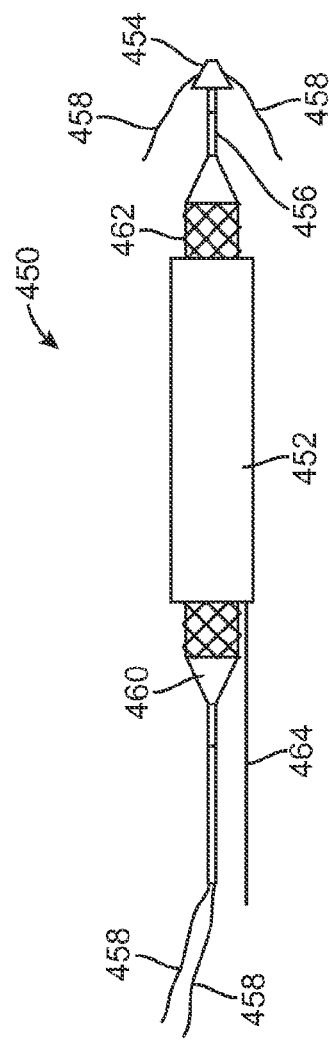
FIG. 12A
FIG. 12B

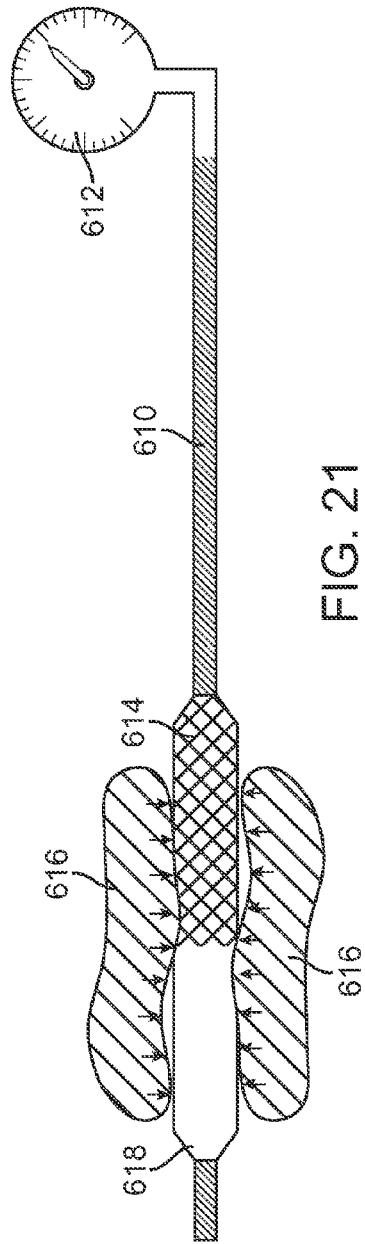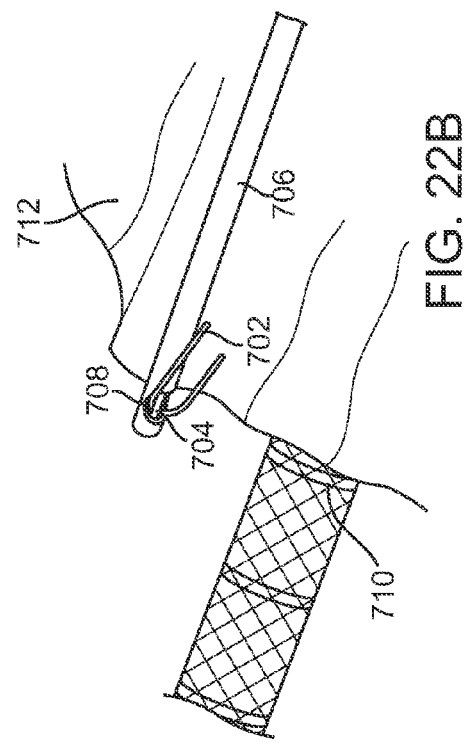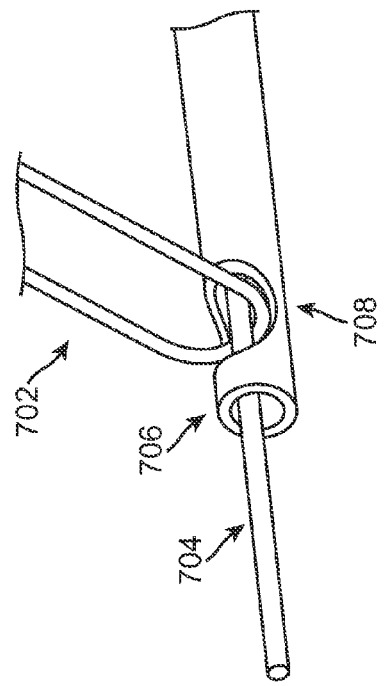
FIG. 21
FIG. 22A
FIG. 22B

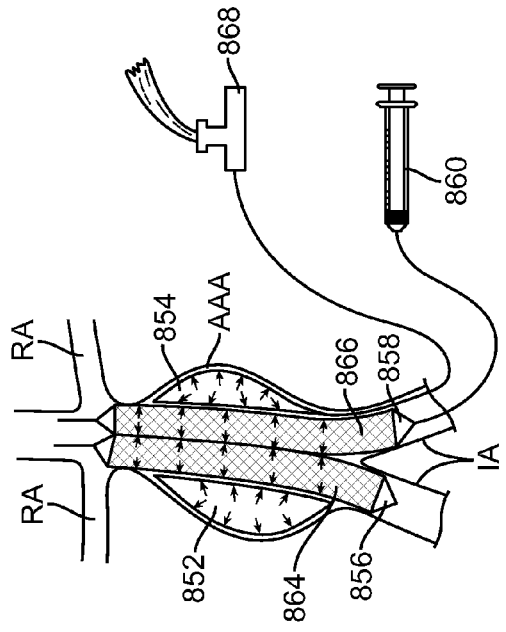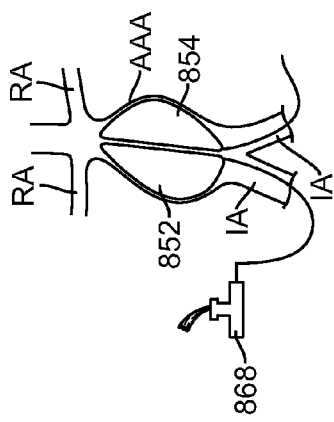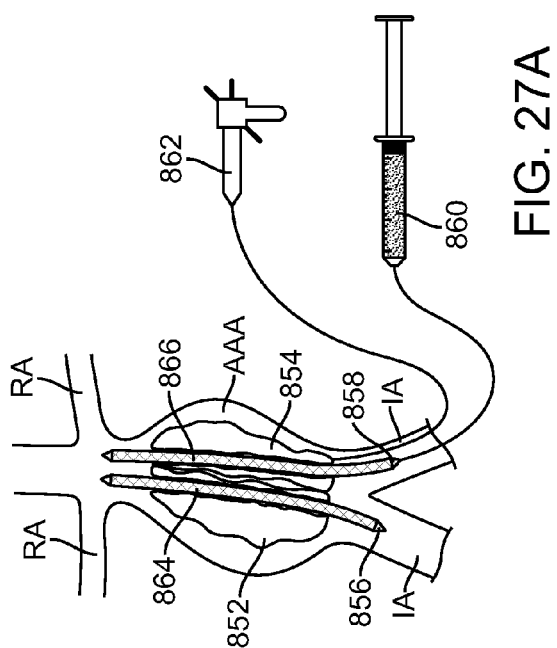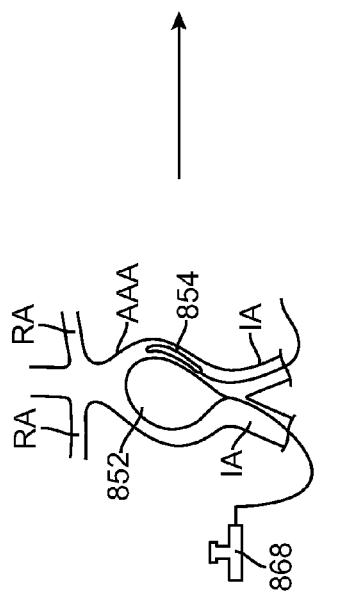
FIG. 27A
FIG. 27B
FIG. 28A
FIG. 28B

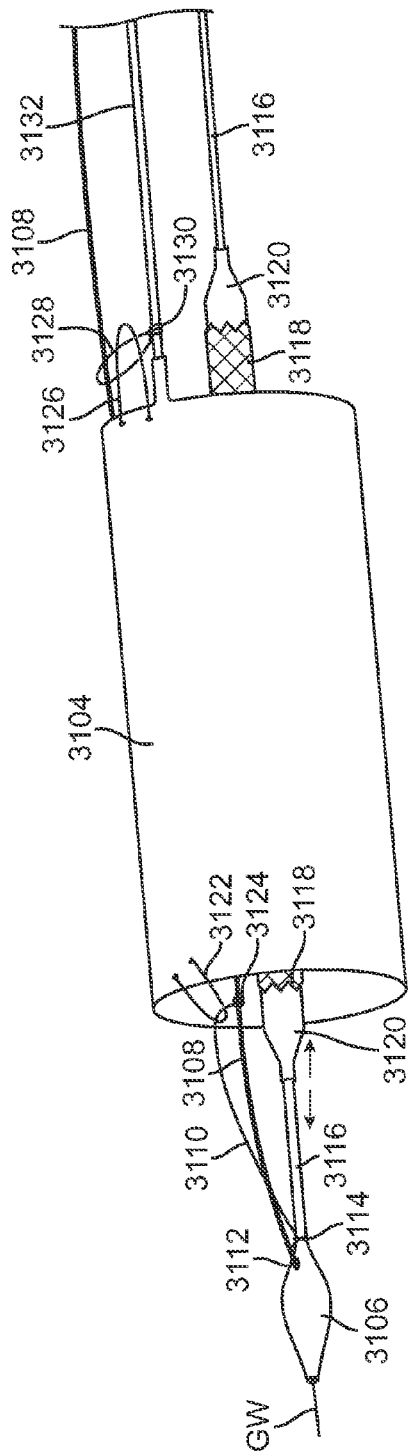
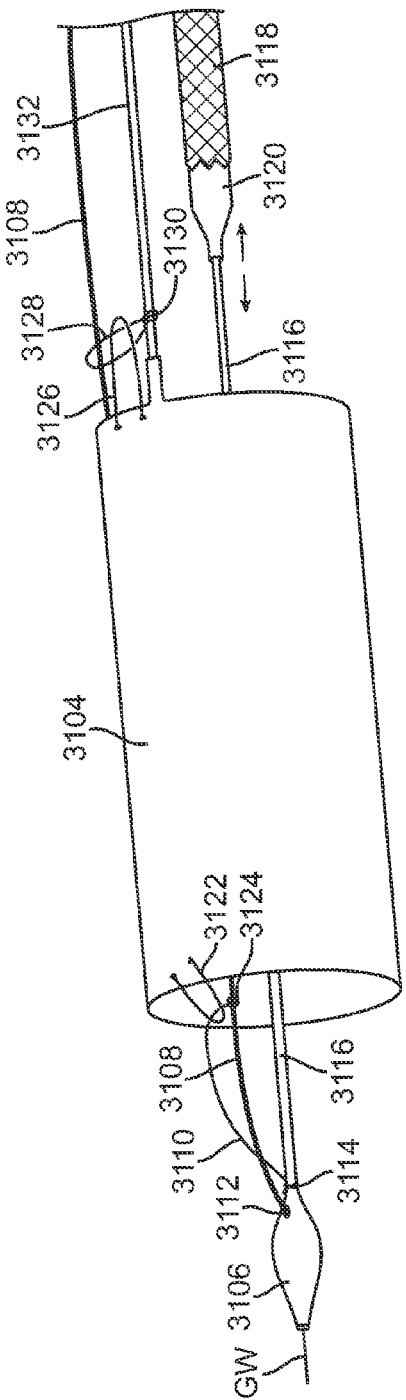
FIG. 32A
FIG. 32B

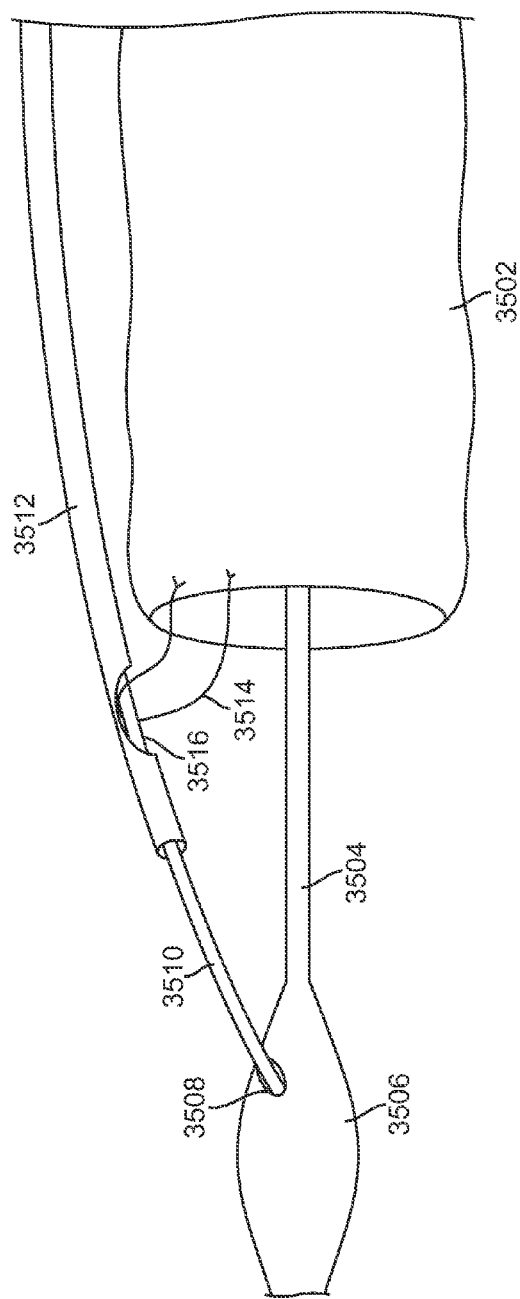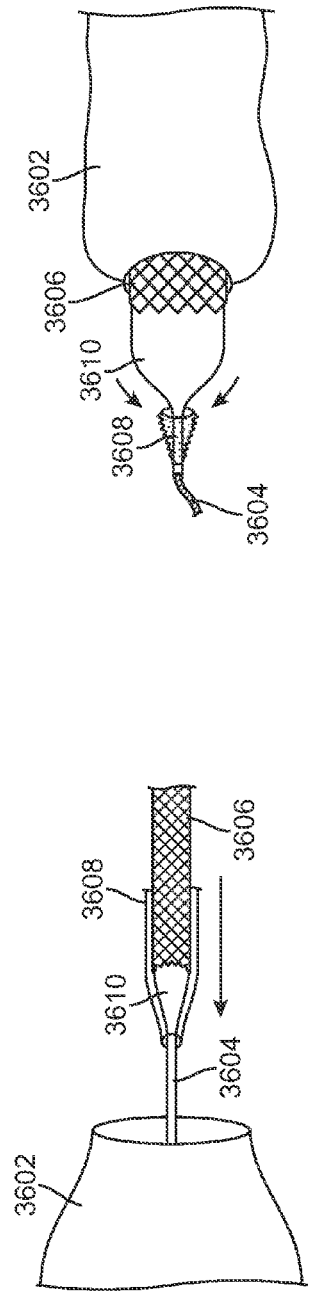
FIG. 35
FIG. 36A
FIG. 36B

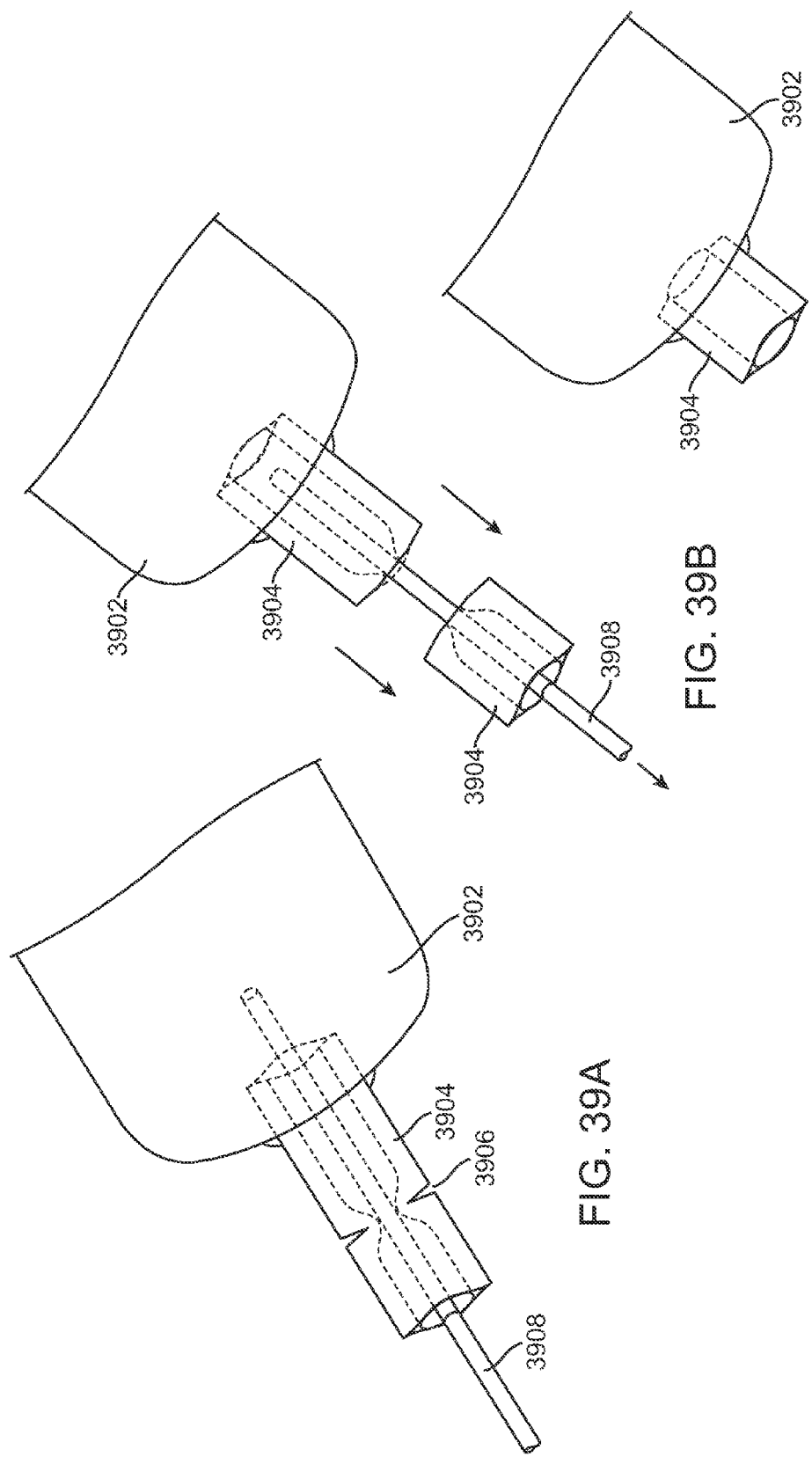

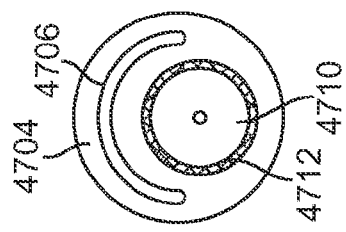
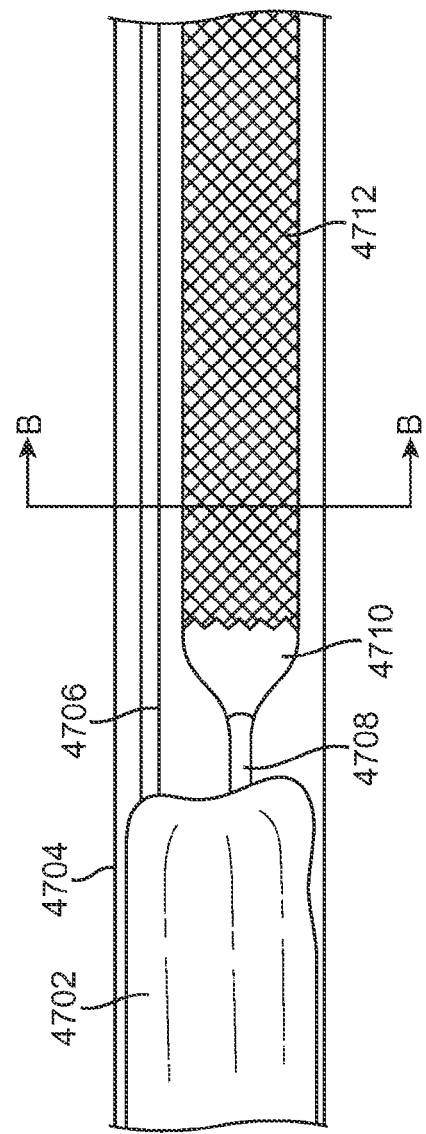
FIG. 47B
FIG. 47A

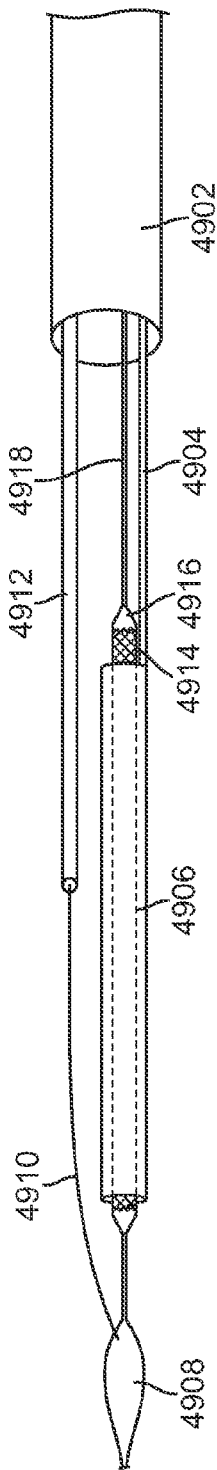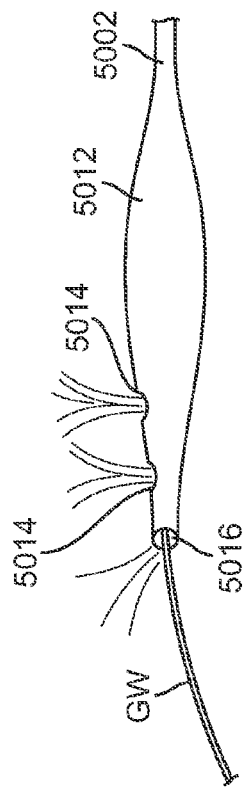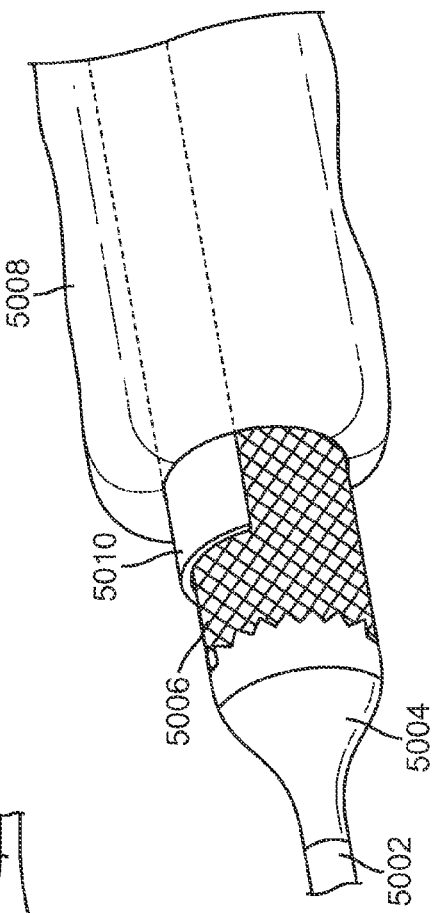
FIG. 49
FIG. 50A
FIG. 50B

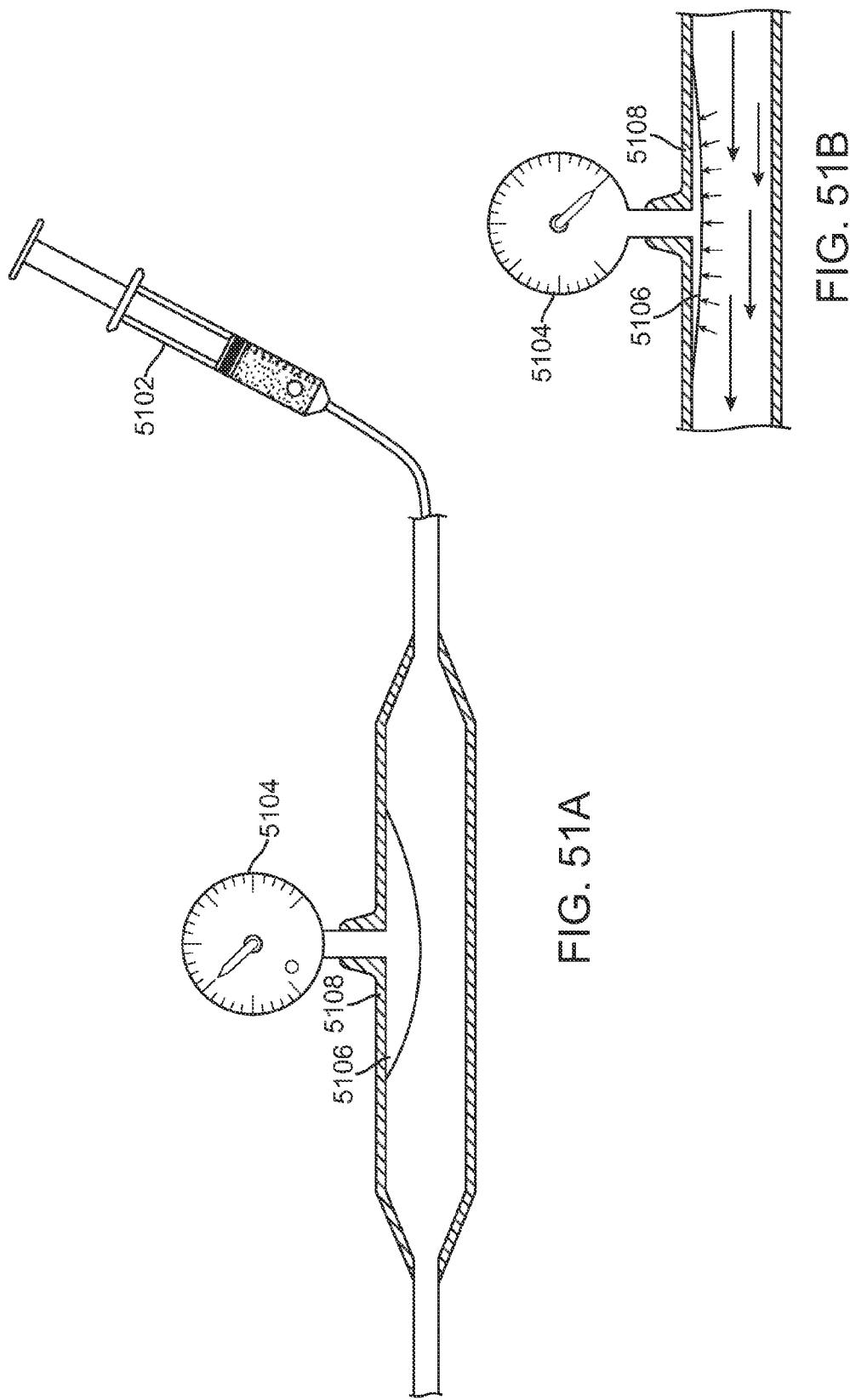

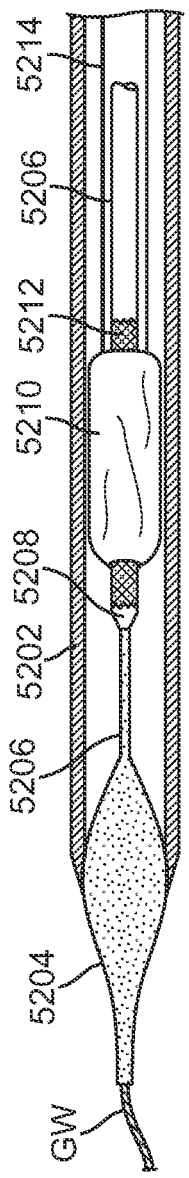
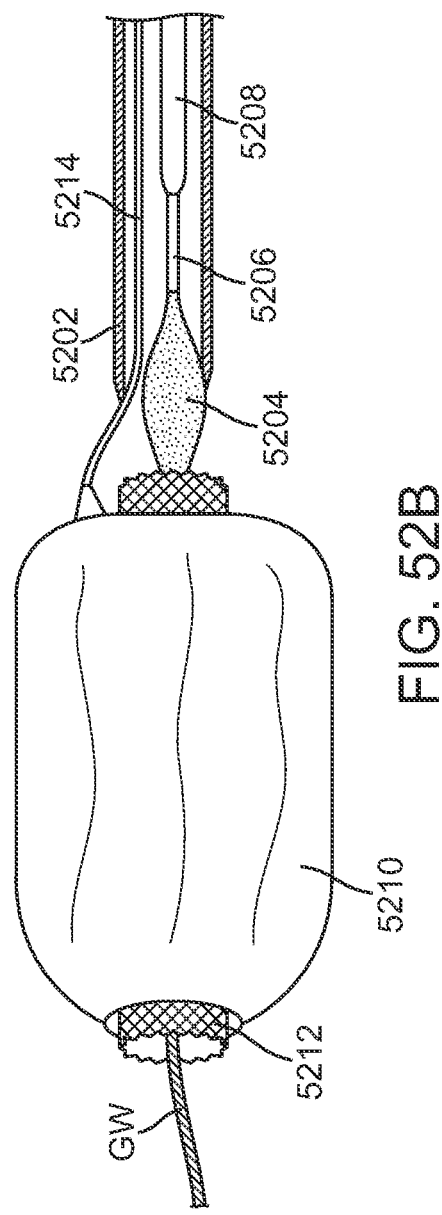
FIG. 52A
FIG. 52B

STENT GRAFT DELIVERY SYSTEM

CROSS-REFERENCES TO RELATED APPLICATIONS

This application is a continuation of U.S. application Ser. No. 13/243,941 filed on Sep. 23, 2011, which is a divisional of U.S. application Ser. No. 12/429,474 filed on Apr. 24, 2009, which is a non-provisional of, and claims the benefit of U.S. Provisional Application No. 61/048,038, filed on Apr. 25, 2008, the full disclosures of which are incorporated herein by reference.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

1. Field of the Invention

The present invention relates generally to medical systems and methods for treatment. More particularly, the present invention relates to systems and methods for treating aneurysms.

Aneurysms are enlargements or "bulges" in blood vessels which are often prone to rupture and which therefore present a serious risk to the patient. Aneurysms may occur in any blood vessel but are of particular concern when they occur in the cerebral vasculature or the patient's aorta.

The present invention is particularly concerned with aneurysms occurring in the aorta, particularly those referred to as aortic aneurysms. Abdominal aortic aneurysms (AAA's) are classified based on their location within the aorta as well as their shape and complexity. Aneurysms which are found below the renal arteries are referred to as infrarenal abdominal aortic aneurysms. Suprarenal abdominal aortic aneurysms occur above the renal arteries, while thoracic aortic aneurysms (TAA's) occur in the ascending, transverse, or descending part of the upper aorta.

Infrarenal aneurysms are the most common, representing about eighty percent (80%) of all aortic aneurysms. Suprarenal aneurysms are less common, representing about 20% of the aortic aneurysms. Thoracic aortic aneurysms are the least common and often the most difficult to treat.

The most common form of aneurysm is "fusiform," where the enlargement extends about the entire aortic circumference. Less commonly, the aneurysms may be characterized by a bulge on one side of the blood vessel attached at a narrow neck. Thoracic aortic aneurysms are often dissecting aneurysms caused by hemorrhagic separation in the aortic wall, usually within the medial layer. The most common treatment for each of these types and forms of aneurysm is open surgical repair. Open surgical repair is quite successful in patients who are otherwise reasonably healthy and free from significant co-morbidities. Such open surgical procedures are problematic, however, since access to the abdominal and thoracic aortas is difficult to obtain and because the aorta must be clamped off, placing significant strain on the patient's heart.

Over the past decade, endoluminal grafts have come into widespread use for the treatment of aortic aneurysm in patients who cannot undergo open surgical procedures. In general, endoluminal repairs access the aneurysm "endoluminally" through either or both iliac arteries in the groin. The grafts, which typically have been fabric or membrane tubes supported and attached by various stent structures, are then implanted, typically requiring several pieces or modules to be assembled in situ. Successful endoluminal procedures have a much shorter recovery period than open surgical procedures.

Present endoluminal aortic aneurysm repairs, however, suffer from a number of limitations. For example, a significant number of endoluminal repair patients experience leakage at the proximal juncture (attachment point closest to the heart) within two years of the initial repair procedure. While such leaks can often be fixed by further endoluminal procedures, the need to have such follow-up treatments significantly increases cost and is certainly undesirable for the patient. A less common but more serious problem has been graft migration. In instances where the graft migrates or slips from its intended position, open surgical repair is required. This is a particular problem since the patients receiving the endoluminal grafts are often those who are not considered to be good surgical candidates.

Further shortcomings of the present endoluminal graft systems relate to both deployment and configuration. For example, many of the commercially available endovascular systems are too large (above 12 F) for percutaneous introduction. Moreover, current devices often have an annular support frame that is stiff and difficult to deliver as well as unsuitable for treating many geometrically complex aneurysms, particularly infrarenal aneurysms with little space between the renal arteries and the upper end of the aneurysm, referred to as short-neck or no-neck aneurysms. Aneurysms having torturous geometries, are also difficult to treat.

For these reasons, it would be desirable to provide improved methods and systems for the endoluminal and minimally invasive treatment of aortic aneurysms. In particular, it would be desirable to provide systems having lower delivery profile and methods which can be delivered percutaneously and that can track and be deployed in tortuous vessels. It would also be desirable to provide prostheses with minimal or no endoleaks, which resist migration, which are flexible and relatively easy to deploy, and which can treat many if not all aneurismal configurations, including short-neck and no-neck aneurysms as well as those with highly irregular and asymmetric geometries. It would be further desirable to provide systems and methods which are compatible with current designs for endoluminal stents and grafts, including single lumen stents and grafts, bifurcated stents and grafts, parallel stents and grafts, as well as with double-walled filling structures which are the subject of the commonly owned, copending applications described below. It would also be desirable to provide systems and methods that provide feedback to the operator as to the positioning and deployment of the endoluminal repair device in the aneurysm. The systems and methods would preferably be deployable with the stents and grafts at the time the stents and grafts are initially placed. Additionally, it would be desirable to provide systems and methods for repairing previously implanted aortic stents and grafts, either endoluminally or percutaneously. At least some of these objectives will be met by the inventions described hereinbelow.

2. Description of the Background Art

U.S. Patent Publication No. 2006/0025853 describes a double-walled filling structure for treating aortic and other aneurysms. Copending, commonly owned U.S. Patent Publication No. 2006/0212112, describes the use of liners and extenders to anchor and seal such double-walled filling structures within the aorta. The full disclosures of both these publications are incorporated herein by reference. PCT Publication No. WO 01/21108 describes expandable implants attached to a central graft for filling aortic aneurysms. See also U.S. Pat. Nos. 5,330,528; 5,534,024; 5,843,160; 6,168,592; 6,190,402; 6,312,462; 6,312,463; U.S. Patent Publications 2002/0045848; 2003/0014075; 2004/0204755; 2005/0004660; and PCT Publication No. WO 02/102282.

BRIEF SUMMARY OF THE INVENTION

The present invention provides systems and methods for the treatment of aneurysms, particularly aortic aneurysms including both abdominal aortic aneurysms (AAA) and thoracic aortic aneurysms (TAA). The systems may be introduced percutaneously or by surgical cutdown into a patient and may have an outer diameter ranging preferably from 10 French to 18 French and more preferably from 12 French to 16 French.

In a first aspect of the present invention, a system for treating an aneurysm in a blood vessel comprises an elongate flexible shaft having a proximal region and a distal region. A first double-walled filling structure is disposed over the distal region of the shaft and has an outer wall and an inner wall. The filling structure may be filled with a hardenable fluid filing medium so that the outer wall conforms to an inside surface of the aneurysm and the inner wall forms a first substantially tubular lumen to provide a path for blood flow. The system also includes a first expandable scaffold disposed adjacent the filling structure. The first scaffold is radially expandable within at least a portion of the tubular lumen of the filling structure and the filling structure is separate from the first scaffold and axially separated therefrom.

In some embodiments, the first scaffold may be proximal to the filling structure while in other embodiments, the first scaffold is distal to the filling structure. Sometimes there is a gap or spacing between one end of the first scaffold and one end of the filling structure. The first scaffold may be slidably received by the filling structure so that the first scaffold and the filling structure are concentric with one another, and the filling structure provides a covering around the scaffold.

Sometimes the delivery system may include a sheath that is disposed at least partially over the filling structure and/or the scaffold. The sheath may have a tapered tip and may have axially oriented slits. The system may also include a pusher tube that is disposed at least partially over the flexible shaft and that slidably engages with the first double-walled filling structure. A first tether may be coupled with the filling structure and the tether may extend between the proximal and distal regions of the flexible shaft. The tether may be adapted to guide movement of the first double-walled filling structure relative to the first scaffold axially along the shaft. The tether may also be used to pull the filling structure as it is axially moved relative to the first scaffold, thereby slidably engaging and positioning the filling structure with the first scaffold. Sometimes the delivery system may also comprise a second tether that is coupled with the filling structure and the second tether may extend between the proximal and distal regions of the flexible shaft. Systems may include one or more eyelets or suture loops coupled with the first filling structure and they may be adapted to receive the tethers or a tube and act as guides or the filling structure may comprise a receptacle coupled with a wall of the filling structure that can slidably receive a tube. The system may also include a nosecone coupled with the distal region of the flexible shaft and sometimes the tethers are coupled thereto. Portions of the tether may extend outside of a patient's body. The tether may be releasably coupled with the filling structure.

The system may further comprise an inflation device, such as a syringe, that is fluidly coupled with the filling structure and a pressure monitor. The pressure monitor may also be coupled with the filling structure so as to permit pressure monitoring of the filling structure as the filling structure is filled with the hardenable fluid filling medium. The pressure monitor may comprise a pressure gage, a digital display or the like.

Sometimes the filling structure comprises a relief valve and an optional reservoir may be fluidly coupled thereto. The relief valve may be fluidly isolated from the first filling structure and the reservoir may be adapted to receive the hardenable fluid filling medium from the relief valve at a predetermined pressure. The reservoir may be radiopaque when at least partially filled with the hardenable fluid filling medium. Other embodiments of the system may have a visual indicator fluidly coupled with the filling structure. The visual indicator may have first and second positions wherein the indicator moves from the first position to the second position when a predetermined pressure is applied to the visual indicator. This indicator may be visible under fluoroscopy.

Other embodiments may comprise a collapsible member such as a balloon that is fluidly coupled with a pressure gage. The collapsible member may be positioned between the outer wall of the filling structure and the inside surface of the aneurysm and thus the pressure gage indicates the pressure of the filling structure as it is filled. Other embodiments may also include a collapsible member such as a balloon that is similarly positioned between the aneurysm wall and the filling structure wall, and that is fluidly coupled with a compression mechanism, such as a spring, having first and second positions. The compression mechanism provides a predetermined force opposing the force exerted by the collapsible member as the filling structure is filled. The compression mechanism moves from the first position to the second position when the force exerted by the collapsible member exceeds the predetermined value. The collapsible member may be a balloon. Some systems may also include a locking mechanism which prevents fluid from filling the filling structure when the filling structure is filled to a predetermined pressure.

In some embodiments, the filling structure may comprise a compliant compartment that deforms as the outer wall of the filling structure conforms to the inside surface of the aneurysm. The compartment may have a substantially flat section and may be fluidly coupled with a pressure indicator.

Sometimes the first or second scaffold may comprise crushable regions and remainder regions. The crushable regions collapse when the filling structure is pressurized to a predetermined value while the remainder regions remain fully expanded. In yet other embodiments, the system may further comprise an expandable member such as a balloon, that expands from a contracted configuration to an expanded configuration and that is coupled with the shaft near the distal region. The expandable member may be fluidly coupled with a pressure monitoring device. The expandable member may have a pre-shaped, curved or tapered region.

The scaffold may be comprised of a metal and may be balloon expandable. The scaffold or filling structure may also carry a therapeutic agent that can be released therefrom in a controlled manner. Some therapeutic agents include anti-thrombogenics like heparin or agents which promote endothelial and smooth muscle cell growth, sealing and attachment. The filling structure may comprise a polymer.

The system may also comprise a second double-walled filling structure having an outer wall and an inner wall. The double-walled filling structure may be placed adjacent the first filling structure in the aneurysm and may be filled with a hardenable fluid filling medium so that the outer wall conforms to the inside surface of the aneurysm and to the first filling structure and forms a second generally tubular lumen to provide a path for blood flow. The system may also include a second scaffold separate from the first scaffold and the filling structures which can be expanded within at least a portion of the second tubular lumen of the second filling structure. The second scaffold may be axially separated from the second filling structure. Both the second scaffold and the second filling structure generally take the same form as the first scaffold and first filling structure. A flowable polymer that may be cured in situ may be used to as the filling material for both the first and second filling structures.

The system may also comprise a releasable coupling mechanism that is coupled with the first filling structure and the shaft. The coupling mechanism is adapted to reduce axial movement along the shaft of the filling structure relative to the scaffold. The releasable coupling mechanism may comprise a tether that is releasably coupled with the shaft and the filling structure. The filling structure may also comprise a filling tube that is fluidly coupled therewith and that is adapted to fill the filling structure with the filling medium. The filling tube may also comprise an inner tube that is slidably disposed in the filling tube. Both the inner tube and the filling tube may be fluidly coupled with the filling structure.

In another aspect of the present invention, a method for treating an aneurysm comprises providing an elongate flexible shaft having a proximal end and a distal end. The flexible shaft carries a first double-walled filling structure and a first scaffold adjacent the distal end. Advancing the elongate shaft in a patient's vasculature allows the first double-walled filling structure to traverse the aneurysm. Filling the first filling structure with a fluid filling medium expands the filling structure so that an outer wall of the first filling structure conforms to an inside surface of the aneurysm and an inner wall of the first filling structure forms a first substantially tubular lumen to provide a first blood flow path across the aneurysm. Axially moving the first scaffold relative to the first filling structure positions at least a portion of the first scaffold within the first substantially tubular lumen and radially expanding the first scaffold expands the first scaffold from a contracted configuration to an expanded configuration.

Axially moving the first scaffold may comprise moving the first scaffold distally into the first lumen or axially moving the first scaffold may comprise proximally retracting the first filling structure over the first scaffold. Axially moving the first scaffold may also comprise proximally retracting the first scaffold into the first lumen or moving the first filling structure distally over the first scaffold. Sometimes axially moving the first scaffold may comprise guiding the first filling structure over a tether line or pulling the first filling structure with a tether line. The method may also include retracting a sheath from the first filling structure or the first scaffolding so that that portion is unconstrained from expansion. The method may also comprise engaging a pusher tube with the first filling structure so as to prevent motion thereof. The method may also further comprise hardening the filling medium in the first filling structure.

The method may also include monitoring a pressure or controlling the filling of the first or second filling structures by changing pressure or volume of the filling medium. Filling the filling structure may comprise controlling pressure and/or volume of the filling medium. The pressure may be one that is exerted by the filling medium within the first filling structure. The monitored pressure may also be a pressure that is within a space between an external wall of the first filling structure and a wall of the aneurysm. Monitoring the pressure may include placing a fluid filled balloon catheter or a pressure transducer in the space between the filling structure and aneurysm wall. Often, the method may further include regulating flow of the filling medium in response to the monitored pressure.

Filling the filling structure may include actuating an injection device and pressure may be monitored at a position adjacent the injection device. The method also may include relieving pressure in the filling structure with a relief valve when the pressure exceeds a predetermined value. Sometimes, the relief valve may be fluidly isolated from the first filling structure. The fluid relieved from the filling structure may fill a reservoir that is fluidly coupled with the relief valve and an operator may observe the reservoir to determine inflation status of the filling structure. Some pressure monitoring devices may include a visual indicator that is coupled with the first filling structure. The indicator may have a first and a second position, and the indicator moves from the first position to the second position when a predetermined pressure is applied to the indicator. An operator may observe the indicator position to determine fillings status of the filling structure.

Other embodiments may include positioning a collapsible member such as a balloon between the outer wall of the filling structure and the inside wall of the aneurysm. An operator observes a compression mechanism having first and second positions that is coupled with the filling structure. The compression mechanism provides a predetermined force opposite to the force exerted by the collapsible member as the filling structure is filled and the compression mechanism moves from the first position to the second position when the force exerted by the collapsible member exceed the predetermined force. The compression mechanism may comprise a spring and the collapsible member may be comprise a balloon.

The method may also include the step of stopping the filling of the filling structure when the monitored pressure reaches a predetermined pressure. Stopping filling may be achieved by mechanically locking a filling device so that fluid may not be delivered therefrom. Monitoring pressure may also include observing the first scaffold. The first scaffold may have crushable regions and remainder regions and the crushable regions collapse when the filling structure is pressurized to a predetermined value while the remainder regions remain fully expanded.

The method may further comprise providing a second elongate flexible shaft having a proximal and distal end. The second shaft carries a second double walled filling structure and a second scaffold adjacent the distal end. Advancing the second elongate shaft in the patient's vasculature allows the second double walled filling structure to traverse the aneurysm. Filling the second filling structure with a fluid filling medium expands the filling structure so that an outer wall of the second filling structure forms a second substantially tubular lumen to provide a second blood flow path across the aneurysm. Filling the second filling structure may also comprise controlling pressure or volume of the fluid filling medium. Axially moving the second scaffold relative to the second filling structure positions at least a portion of the second scaffold within the second substantially tubular lumen and radially expanding the second scaffold expands the scaffold from a contracted configuration to an expanded configuration.

Axially moving the second scaffold may comprise moving the second scaffold distally into the second lumen or proximally retracting the second filling structure over the second scaffold. Axially moving the second scaffold may also comprise proximally retracting the second scaffold into the second lumen or moving the second filling structure distally over the second scaffold.

The method may also comprise retracting a sheath from either the second filling structure and/or the second scaffolding so that either or both are unconstrained from expansion. Retracting the sheath may also comprise splitting the sheath. The method also may comprise hardening the fluid filling medium in the second filling structure and monitoring a second pressure. The second pressure may be exerted by the filling medium in the second filling structure. Often, the flow of the filling medium may be regulated in response to the second monitored pressure. In some embodiments, the method may comprise filling either the first or the second filling structure until it engages the other filling structure resulting in filling medium being discharged from either the first or second filling structure. In still other embodiments, the method may comprise inflating a balloon on either the first or the second elongate shaft so as to compress the first and second filling structures against one another and against the aneurysm wall. Often filling medium will be discharged from either the first or second filling structure when the balloons are inflated. Radially expanding any of the scaffolds may comprise inflating a balloon disposed near the distal end of the shaft. The balloon may comprise a preshaped, curved or tapered region.

The method may also comprise releasing a releasable coupling mechanism that couples the filling structure with the shaft to allow axial movement of the filling structure relative to the scaffold and that also allows release of the filling structure from the shaft. Releasing the coupling mechanism may comprise releasing a knot in a tether joining the filling structure with the shaft. A filling tube may be fluidly coupled with the filling structure and the step of filling the filling structure may comprise passing fluid filling medium through the filling tube to the filling structure. The filling tube may comprise an inner tube that is slidably disposed therein and that is also in fluid communication with the filling structure. The method may comprise removing the inner tube and passing additional fluid filling medium through the filling tube after the inner tube has been removed.

In another aspect of the present invention, a system for treating an aneurysm in a blood vessel comprises an elongate flexible shaft having a proximal region and a distal region. An expandable member is disposed adjacent the distal region and a first expandable scaffold is disposed over the expandable member. The first scaffold is radially expandable from a collapsed configuration to an expanded configuration. A first double-walled filling structure is disposed over the first scaffold. The filling structure has an outer wall and an inner wall and the filling structure is adapted to be filled with a hardenable fluid filing medium so that the outer wall conforms to an inside surface of the aneurysm and the inner wall forms a first substantially tubular lumen to provide a path for blood flow. In the expanded configuration, the first scaffold engages the inner wall of the filling structure. A first releasable coupling mechanism releasably couples the filling structure with the flexible shaft and the coupling mechanism may comprise a tether that is releasably coupled with the filling structure and the flexible shaft. The coupling mechanism constrains axial movement of the filling structure relative to the flexible shaft.

The first tether may comprise a suture, and in some embodiments the system may include a lockwire disposed alongside the flexible shaft. A distal end of the lockwire may be releasably coupled with the flexible shaft. The flexible shaft may comprise a tapered nosecone having an aperture therein and the nosecone may be coupled with the distal region of the flexible shaft such that the distal end of the lockwire may be releasably coupled with and slidably received in the nosecone aperture. The first tether may be releasably coupled to the lockwire. The filling structure may include a first tether loop fixedly attached thereto, and the first tether may pass through the tether loop. The first tether loop may be disposed on a distal end of the filling structure. In some embodiments, the first tether may be releasably coupled to the lockwire with a knot such as a constrictor knot. One end of the first tether may be fixedly attached with the flexible shaft.

The system may further comprise a second releasable coupling mechanism. The second mechanism may comprise a tether that is releasably coupled with the filling structure and the flexible shaft. The second tether may be on an opposite end of the filling structure as the first tether, and the second tether may constrain axial movement of the filling structure relative to the flexible shaft. The second tether may comprise a suture and may be releasably coupled to the lockwire. The second tether may be looped around the lockwire. In some embodiments, the filling structure comprises a second tether loop fixedly attached thereto and disposed on an opposite end as the first tether loop, and the second tether may pass through the second tether loop. The second tether may be coupled to the flexible shaft and may be releasably coupled to the flexible shaft with a knot, such as a constrictor knot.

The system may further comprise a second releasable coupling mechanism, such as a tether that is releasably coupled with the filling structure and the flexible shaft. The second tether may be disposed on the same end of the filling structure as the first tether, and the second tether may constrain axial movement of the filling structure relative to the flexible shaft. The second tether may comprise a suture. In some embodiments, the system may further comprise a second lockwire disposed alongside the flexible shaft. A distal end of the second lockwire may be releasably coupled with the flexible shaft. The distal region of the flexible shaft may include a tapered nosecone having a second aperture and the distal end of the second lockwire may be releasably coupled with and slidably received in the second nosecone aperture. The second tether may be releasably coupled to the lockwire.

In some embodiments, the filling structure may comprise a second tether loop fixedly attached thereto, and wherein the second tether passes through the second tether loop. The second tether loop may be disposed on the same end of the filling structure as the first tether loop. The second tether may be releasably coupled to the lockwire with a knot such as a constrictor knot. One end of the second tether may be fixedly attached with the flexible shaft.

The system may further comprise a filling tube fluidly coupled with the filling structure. The filling tube may be adapted to deliver the hardenable filling medium to the filling structure. The filling tube may comprise a plurality of apertures near a distal end thereof and that are adapted to allow the hardenable filling medium to flow therethrough into the filling structure. The filling tube may comprise an inner filling tube and an outer filling tube slidably disposed thereover, both fluidly coupled with the filling structure. A stylet may be disposed in the filling tube. Some embodiments may include a filling tab fluidly coupled with the filling structure and fluidly coupled with the filling tube. The filling tab may comprise a scored region adapted to permit separation of the filling tab into two portions, the first portion remaining coupled with the filling structure after filling thereof with the hardenable filling medium and the second portion discrete and independent of the first portion.

In still other embodiments, the system may further comprise an outer sheath having a lumen. The filling structure, the scaffold and the expandable member may be disposed in the sheath lumen during delivery of the system to a treatment site. Other embodiments may include a second elongate flexible shaft having a proximal region and a distal region and a second expandable member disposed adjacent the distal region. A second expandable scaffold may be disposed over the second expandable member. The second scaffold may be radially expandable from a collapsed configuration to an expanded configuration. The system may also include a second double-walled filling structure disposed over the second scaffold. The second filling structure may have an outer wall and an inner wall, wherein the second filling structure is adapted to be filled with a hardenable fluid filing medium so that the outer wall conforms to an inside surface of the aneurysm and the inner wall forms a first substantially tubular lumen to provide a path for blood flow. The second scaffold in the expanded configuration may engage the inner wall of the filling structure, and the system may also have a tether releasably coupled with the second filling structure and the second flexible shaft. The tether may constrain axial movement of the second filling structure relative to the second flexible shaft.

In yet another aspect of the present invention, a method for treating an aneurysm in a patient comprises providing an elongate flexible shaft having a proximal end, a distal end, and an expandable member near the distal end. The flexible shaft carries a first radially expandable scaffold over the expandable member and a first double walled filling structure disposed over the first scaffold. Advancing the shaft in the vasculature of the patient allows the first filling structure to be delivered to the aneurysm. Radially expanding the first scaffold expands the scaffold from a contracted configuration to an expanded configuration, wherein in the expanded configuration the first scaffold engages the inner wall of the first filling structure. Filling the first filling structure with a first fluid filling medium allows an outer wall of the first filling structure to conform to an inside surface of the aneurysm and an inner wall of the first filling structure forms a first substantially tubular lumen to provide a first blood flow path across the aneurysm. Filling the first filling structure with the first fluid filling medium also allows assessment of the filling volume by removing and recording the first filling medium. Filling the first filling structure with a second fluid filling medium allows an outer wall of the first filling structure to conform to an inside surface of the aneurysm and an inner wall of the first filling structure forms a substantially tubular lumen to provide a first blood flow path across the aneurysm. The second fluid filling medium is hardened in the first filling structure and then the first filling structure is released from the flexible shaft. The flexible shaft is then retracted away from the first filling structure.

The method may further comprise pre-filling the first filling structure with a pre-filling fluid until the outer wall of the first filling structure conforms to the inside surface of the aneurysm, thereby unfurling the first filling structure. The pre-filling fluid may comprise saline and may be removed from the first filling structure. The method may also comprise pre-filling the first filling structure with pre-filling fluid until the outer wall of the first filling structure conforms to the inside surface of the aneurysm. The pressure and volume of the pre-filling fluid used to pre-fill the first filling structure may be measured and then the pre-filling fluid may be removed from the first filling structure. Filling the first filling structure with the first fluid filling medium may comprise filling the first filling structure with the first filling medium using substantially the same pressure and volume as measured. The pre-filling fluid may comprise saline or contrast media to assist visualizing the filling process under x-ray fluoroscopy. The first filling medium may be passed through a filling tube that is fluidly coupled with the first filling structure.

Radially expanding the scaffold may comprise inflating a balloon that is disposed on the flexible shaft. Hardening the first fluid filling medium in the first filling structure may comprise polymerizing the first fluid filling medium in situ. The first fluid filling medium may comprise polyethylene glycol.

A releasable coupling mechanism such as a tether may couple the first filling structure with the flexible shaft and the step of releasing the first filling structure from the flexible shaft may comprise releasing the coupling mechanism or de-coupling the tether from the first filling structure. One end of the tether may be releasably coupled with a lockwire and the step of de-coupling the tether may comprise retracting the lockwire thereby detaching the tether from the lockwire. De-coupling the tether may comprise releasing the tether from a tether loop on the first filling structure. In some embodiments, a second releasable coupling mechanism, such as a tether may couple the first filling structure with the flexible shaft and the step of releasing the first filling structure from the flexible shaft may comprise de-coupling the second tether from the first filling structure. Releasing one or more of the coupling mechanisms may permit separation of a filling tube from the filling structure.

The method may further comprise the step of retracting a sheath away from the first filling structure and the first scaffold to allow expansion thereof. Pressure may be monitored during filling of the first filling structure. The monitored pressure may be a pressure of the filling medium in the first filling structure or a pressure in a space between the outer wall of the first filling structure and a wall of the aneurysm. A filling tube may be released from the first filling structure after the hardenable filling medium has been delivered thereto. Releasing the filling tube may comprise severing a filling tab coupled with the first filling structure.

In some embodiments, the method may further comprise providing a second elongate flexible shaft having a proximal end, a distal end, and a second expandable member near the distal end. The second flexible shaft may carry a second radially expandable scaffold over the second expandable member and a second double walled filling structure may be disposed over the second scaffold. The second shaft may be advanced in the vasculature of the patient so that the second filling structure is delivered to the aneurysm and the second filling structure is filled with a second fluid filling medium so that an outer wall of the second filling structure conforms to an inside surface of the aneurysm and an inner wall of the second filling structure forms a second substantially tubular lumen to provide a second blood flow path across the aneurysm. The second scaffold is radially expanded from a contracted configuration to an expanded configuration wherein in the expanded configuration the second scaffold engages the inner wall of the second filling structure. The second fluid filling medium may be hardened in the second filling structure and the second flexible shaft is released from the second filling structure. The second shaft may be retracted away from the second filling structure.

The first filling structure may comprise a filling tube that is fluidly coupled therewith and the step of filling the first filling structure may comprise passing filling medium through the filling tube. The filling tube may comprise an inner tube that is slidably disposed therein and that is also fluidly coupled with the filling structure. The method may further comprise removing the inner tube from the filling tube and supplying additional filling medium to the filling structure by passing the filling medium through the filling tube after the inner tube has been removed therefrom.

These and other embodiments are described in further detail in the following description related to the appended drawing figures.

BRIEF DESCRIPTION OF THE DRAWINGS

FIGS. 4A-4I illustrate exemplary usage of the system in FIG. 3 for treating an infrarenal abdominal aortic aneurysm.

FIGS. 11A-11B show the use of a tether line to help guide movement of the filling structure relative to the scaffold.

FIGS. 12A-12B show the use of a tether line to help pull the filling structure toward the scaffold.

FIG. 21 illustrates an aneurysm treatment system with integrated pressure monitoring.

FIGS. 22A-22B illustrate the use of a hitch to hold the filling structure.

FIGS. 27A-27B show how filling may be controlled with the balloons on a delivery catheter.

FIGS. 28A-28B illustrate how filling may be controlled with the filling structures themselves.

FIGS. 32A-32B illustrate positioning of a filling structure relative to an endoframe.

FIG. 35 illustrates the use of a support post and lockwire.

FIGS. 36A-36B illustrate use of a sheath.

FIGS. 39A-39C illustrate separation of the filling tube from a filling structure.

FIGS. 47A-47B illustrate an exemplary delivery system.

FIG. 49 illustrates an exemplary embodiment of a delivery system.

FIGS. 50A-50B illustrate various embodiments for introducing contrast media.

FIGS. 51A-51B illustrate a pressure measuring device that can mask pressure spikes.

FIGS. 52A-52D illustrate the use of a split sheath.

DETAILED DESCRIPTION OF THE INVENTION

Figure 1:
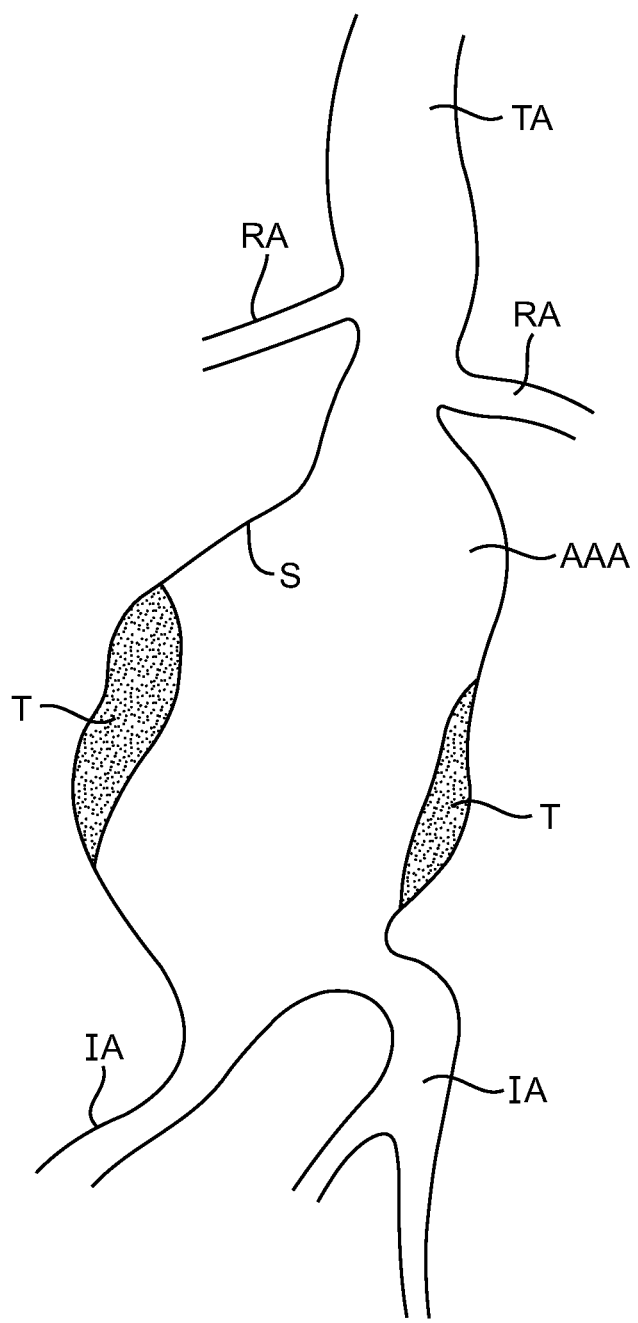
FIG. 1 illustrates the anatomy of an infrarenal abdominal aortic aneurysm.

FIG. 1 illustrates the anatomy of an infrarenal abdominal aortic aneurysm comprising the thoracic aorta (TA) having renal arteries (RA) at an end above the iliac arteries (IA). The abdominal aortic aneurysm (AAA) typically forms between the renal arteries (RA) and the iliac arteries (IA) and may have regions of mural thrombus (T) over portions of its inner surface (S).

Figure 2:
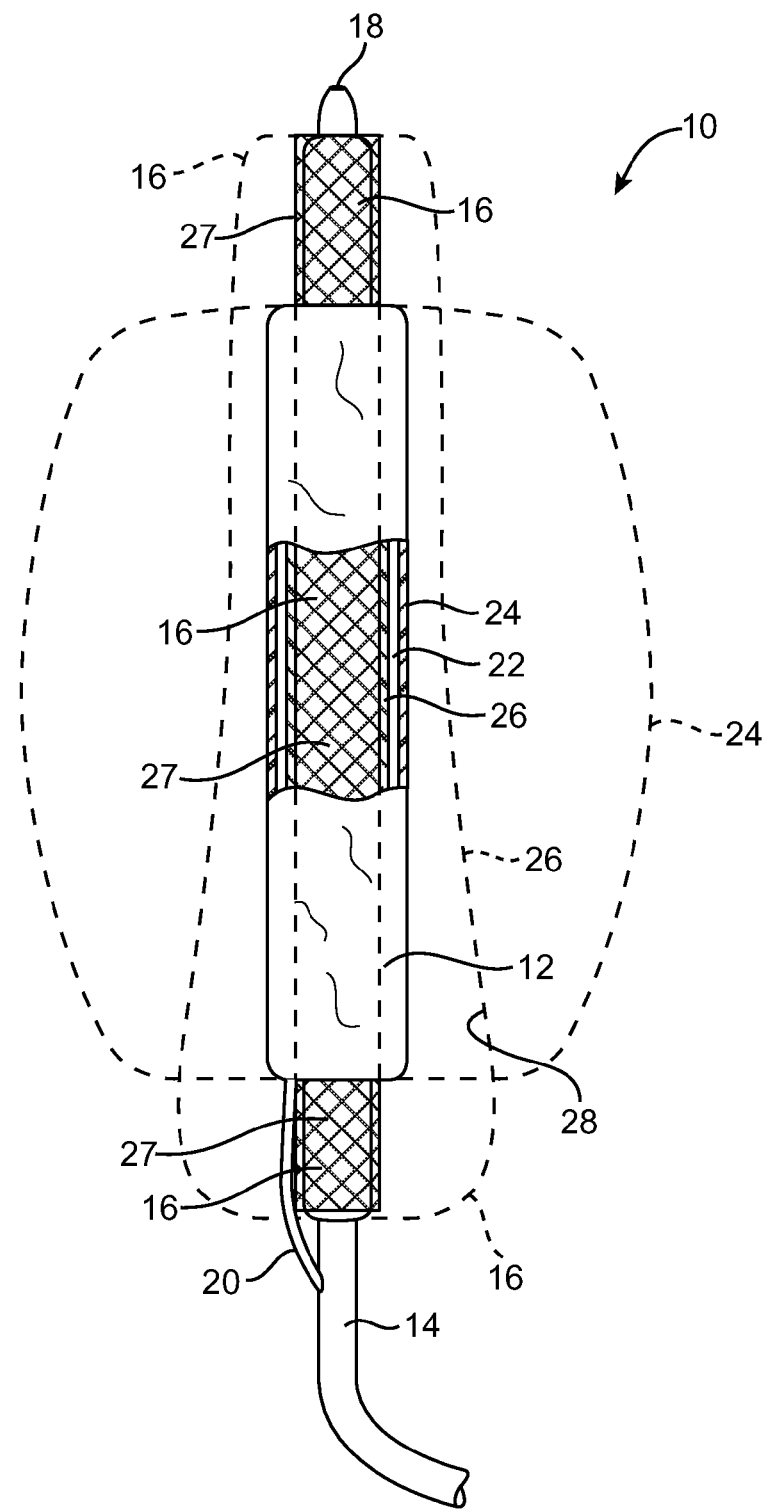
FIG. 2 illustrates a delivery catheter carrying a single prosthesis system which comprises a filling structure mounted over a scaffold structure.

Referring now to FIG. 2, a system 10 constructed in accordance with the principles of the present invention for delivering a double-walled filling structure 12 (also referred to as an endograft in this disclosure) to an aneurysm includes the filling structure 12 disposed over a radially expandable endoframe 27 (also referred to as a scaffold, stent or scaffolding in this disclosure), both of which are then mounted on a delivery catheter 14 having an expandable element 16, typically an inflatable balloon, at its distal end. Expandable element 16 traverses the entire length of the endoframe 27 so that the endoframe 27 may be radially expanded upon expansion of the expandable element 16. Endoframe 27 traverses the entire length of filling structure 12 and most of endoframe 27 is covered by filling structure 12, however endoframe 27 also has proximal and a distal regions that extend uncovered beyond the filling structure 12. One of skill in the art will appreciate that lengths of the filling structure, endoframe and expandable element may be adjusted as required and thus the relative lengths are not limited to those disclosed above. Further details about the double-walled filling structure are disclosed in U.S. Patent Publication No. 2006/0212112 and preferred embodiments of an endoframe scaffold are disclosed in U.S. Provisional Patent Application No. 61/029,225 and U.S. patent application Ser. No. 12/371,087, both of which the entire contents are incorporated herein by reference. The catheter 14 will comprise a guidewire lumen 18, a balloon inflation lumen (not illustrated) or other structure for expanding other expandable components, and a filling tube 20 for delivering a filling medium or material to an internal space 22 of the double-walled filling structure 12. The internal space 22 is defined between an outer wall 24 and inner wall 26 of the filling structure. Upon inflation with the filling material or medium, the outer wall 24 will expand radially outwardly, as shown in broken line, as will the inner wall 26, also shown in broken line. Expansion of the inner wall 26 defines an internal lumen 28. The expandable balloon or other structure 16 will be expandable to correspondingly expand the endoframe 27 to provide support and to shape an inner surface of the lumen 28. In this embodiment, the expandable balloon is substantially cylindrically shaped and therefore the lumen will also be cylindrically shaped. In other embodiments, the balloon may be pre-shaped to more precisely match the curvature of the vessel. For example, when treating an aortic aneurysm, a tapered, pre-shaped or curved balloon may be used so that the lumen substantially matches the aorta. Various balloon configurations may be used in order to match vessel tortuosity. Pre-shaped, curved or tapered balloons may be used in any of the embodiments disclosed herein in order to obtain a desired lumen shaped.

Figure 3:
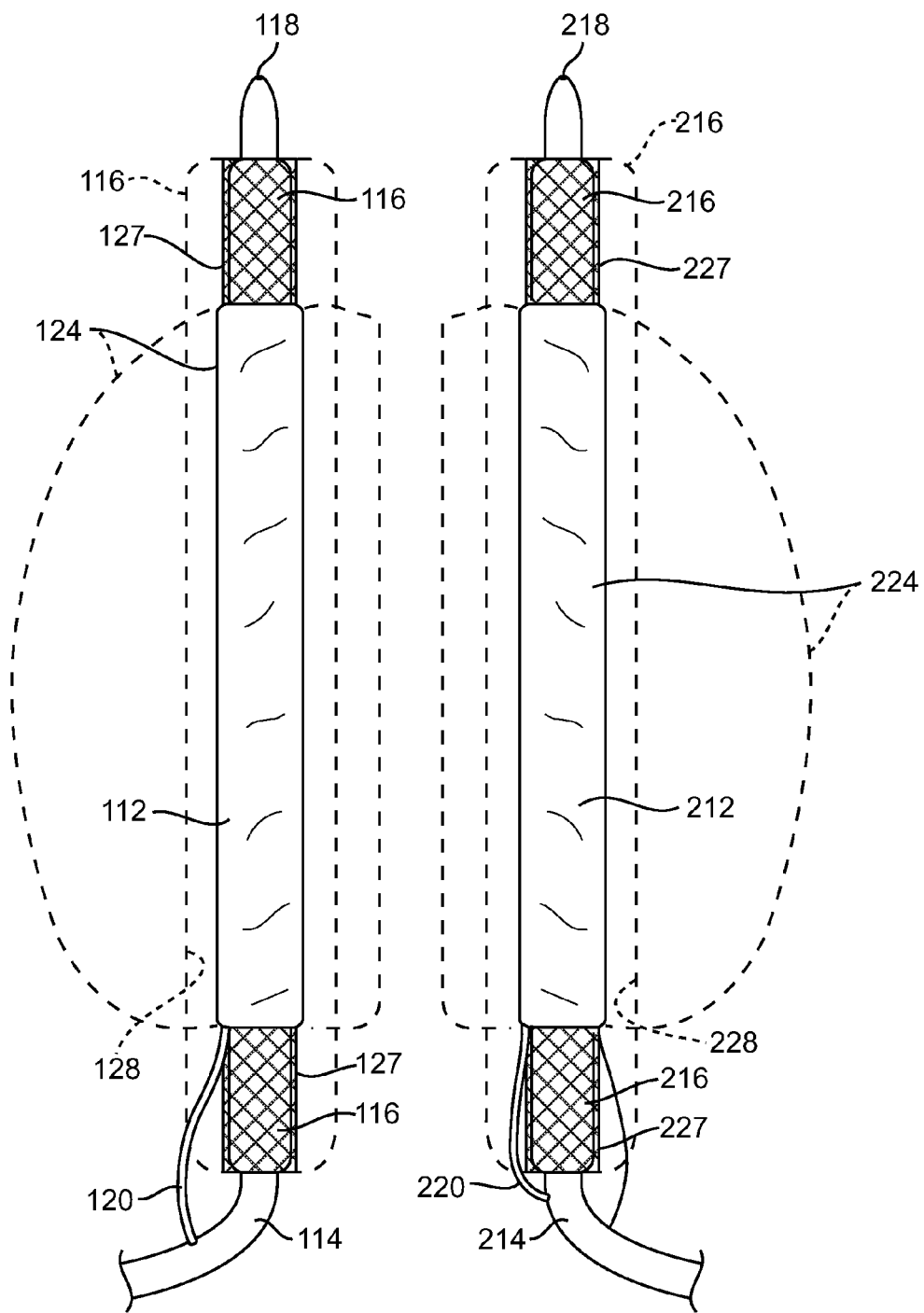
FIG. 3 illustrates a system comprising a pair of prostheses for delivery to an infrarenal abdominal aortic aneurysm, where each prosthesis comprises a delivery catheter carrying a filling structure mounted over a scaffold structure.

In a particular and preferred aspect of the present invention, a pair of double-walled filling structures will be used to treat infrarenal abdominal aortic aneurysms, instead of only a single filling structure as illustrated in FIG. 1. A system comprising such a pair of filling structures is illustrated in FIG. 3 which includes a first filling structure 112 and a second filling structure 212. Each of the filling structures 112 and 212 are mounted on delivery catheters 114 and 214, respectively and each system also has a radially expandable endoframe scaffold 127, 227. The components of the filling structures 112 and 212, the endoframes 127, 227 and delivery catheters 114 and 214 are generally the same as those described previously with respect to the single filling structure system 10 of FIG. 1. Corresponding parts of each of the filling systems 112 and 212 will be given identical numbers with either the 100 base number or 200 base number. The filling structures 112 and 212 will generally be positioned adjacent each other within the aneurismal space to fill that space, as will be described with specific reference to FIGS. 4A-4I below.

Figure 4B:
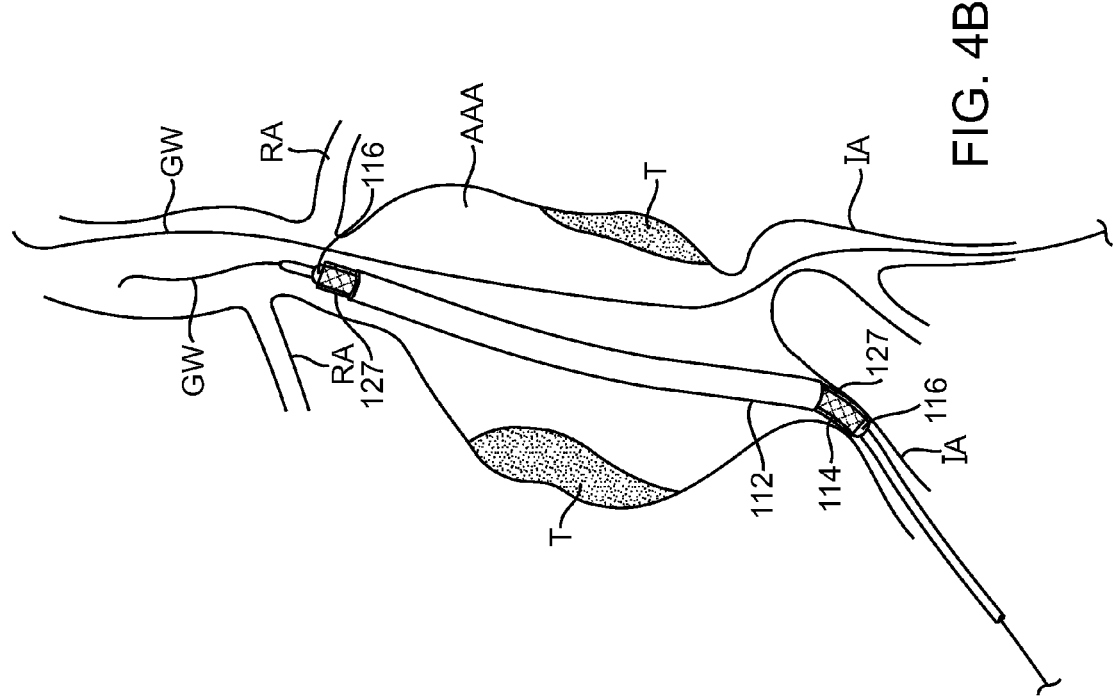
Figure 4A:
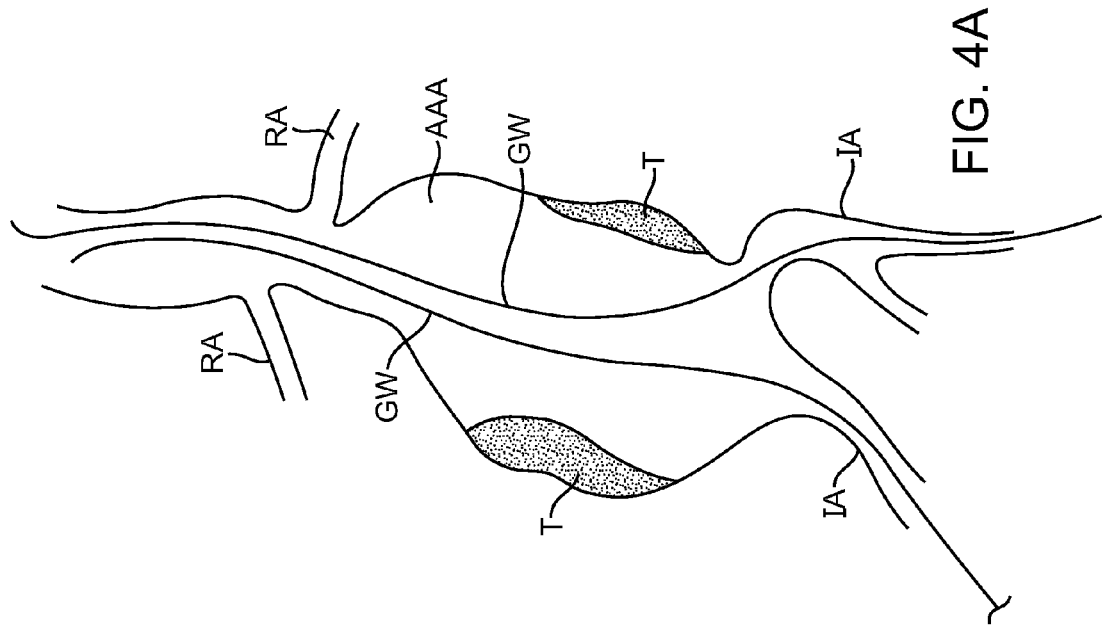
Figure 10A:
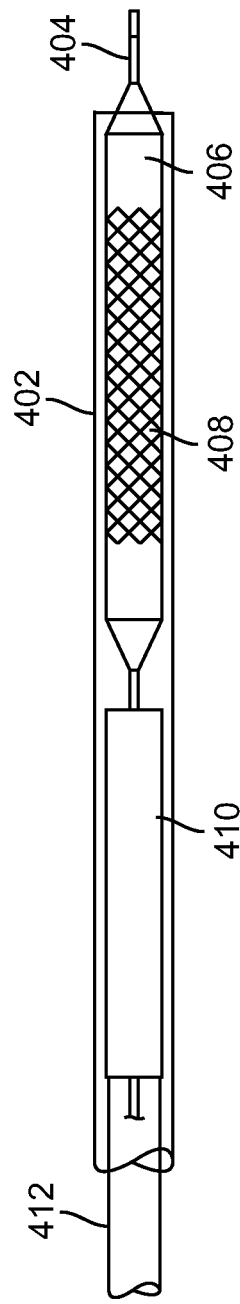
FIGS. 10A-10B illustrate the use of various sheath embodiments.

FIGS. 4A-4I illustrate an exemplary use of the system in FIG. 3 for treating an infrarenal abdominal aortic aneurysm AAA with or without mural thrombus T. An optional sheath may be disposed over the scaffold and/or filling structure as seen in FIG. 10A. In FIG. 4A a pair of guidewires (GW) will first be introduced preferably percutaneously or by surgical cut down, from each of the iliac arteries (IA) and advanced across the aneurysm toward the renal arteries (RA). Referring now to FIG. 4B, the first delivery catheter 114 having expandable balloon 116 will then be positioned over one of the guidewires GW to position the double-walled filling structure 112 across the aortic aneurysm (AAA) along with scaffold 127. The second delivery catheter 214 having expandable balloon 216 is then delivered over the other guidewire GW to position the second filling structure 212 adjacent to the first structure 112 across the aneurysm (AAA) along with scaffold 227, as illustrated in FIG. 4C. If either of the delivery catheters 114, 214 include sheaths covering their respective scaffold and/or filling structure, the sheath (not illustrated) will be retracted. Typically, one of the filling structures 112, 212 and associated balloons 116, 216 will be expanded first along with the corresponding scaffold 127, 227, followed by the other filling structure, scaffold and balloon. In some embodiments, both balloons may be radially expanded simultaneously thereby also expanding the filling structures and scaffolds simultaneously.

Alternatively, one or both filling structures 112, 212 may be filled with a hardenable material and then the filling structures 112, 212 are radially expanded along with the corresponding scaffold 127, 227. In still other embodiments, combinations of filling and expanding may be performed in different order depending on physician preference and aneurysm anatomy. In some embodiments, an optional unfurling of the filling structure may be performed prior its filling and radial expansion. In this optional step, once the delivery system is positioned across the aneurysm, the filling structure may be filled with $CO_2$ gas, contrast media, saline or other fluids to unfurl the filling structure away from the delivery catheter thereby helping to ensure more uniform filling later on. During unfurling, the filling structure may be partially filled or fully filled so that it conforms to the inner aneurysm wall. Once unfurled, the fluid may be removed from the filling structure and it may be filled with the hardenable material to expand and conform to the aneurismal space between the lumens and the inner aneurysm wall. Pressure relief valves such as those described below may also be used to ensure that the filling structure is not over filled.

In another variation of the method, an optional contrast pre-filling step may be utilized. In this embodiment, after the delivery catheter is positioned across the aneurysm and the endoframe has been radially expanded, the filling structure may be pre-filled with contrast media so as to permit observation of the filled filling structure under a fluoroscope relative to the aneurismal sac. Additionally, the pre-filling step allows the physician to record the pressure and volume of the contrast media used for optimal filling of the filling structure and this will provide an estimate of volume and pressure to be used when filling the filling structure with the hardenable filling material. In order to prevent overfilling of the filling structure, any of the pressure relief valves disclosed below may also be used to bleed off excess fluid from the filling structure.

Figure 4F:
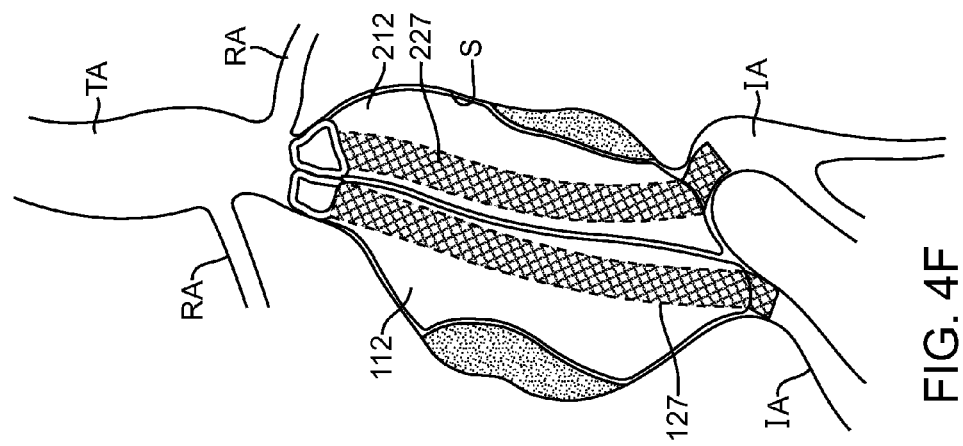
Figure 4E:
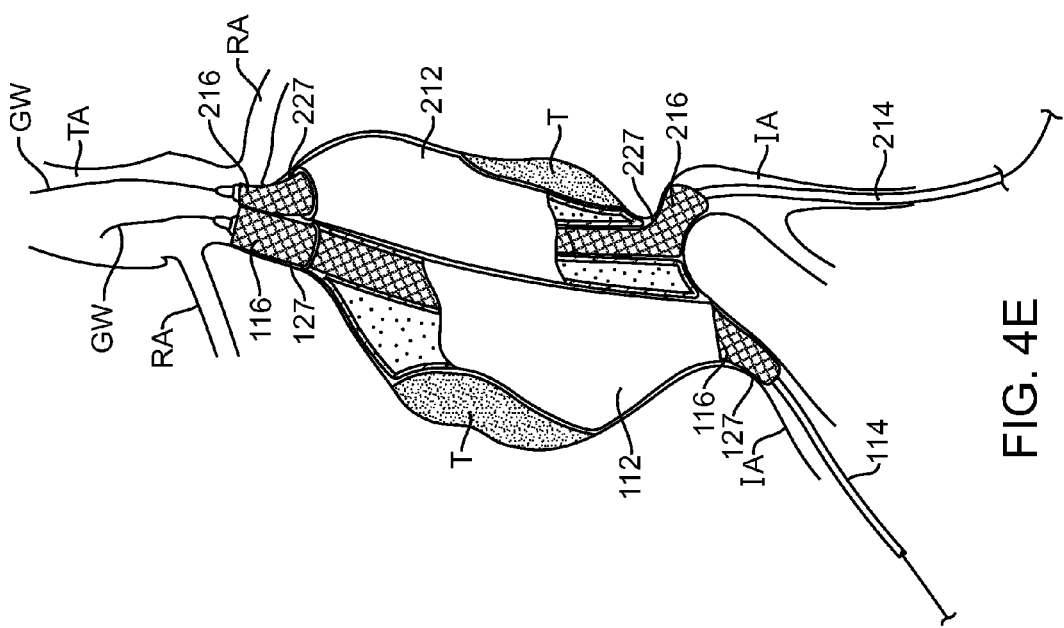

FIG. 4D illustrates inflation of balloon 116 along with scaffold 127 in addition to expansion and filling of filling structure 112. The filling structure 112 and balloon 116 are expanded and inflated to fill generally half of the aneurismal volume, as illustrated in FIG. 4D. Filling and expansion can generally be carried out as described in U.S. Patent Publication No. 2006/0212112 for one filling structure, except of course that the filling structure 112 will be expanded to occupy only about one-half of the aneurismal volume. U.S. Patent Publication No. 2006/0212112 discloses filling of one filling structure in more detail including pressures, filling materials and other details, the entire contents of which have previously been incorporated herein by reference. After the first filling structure 112 has been filled, the second filling structure 212 may be filled and expanded along with scaffold 227, as illustrated in FIG. 4E. FIG. 4E also illustrates a cut away view of the expanded scaffolds 127, 227 within the filled filling structures 112, 212. The upper ends of the balloons 116 and 216 will conform the tubular lumens of the filling structures against the walls of the aorta as well as against each other, while the lower ends of the balloons 116 and 216 will conform the tubular lumens into the respective iliac artery, IA. The expanded scaffold 127 not only provides support to filling structure 112, but also creates and shapes a lumen for blood passage from the aorta to one of the iliac arteries. Similarly, expanded scaffold 227 also provides a lumen for blood passage from the aorta into the other iliac artery. In some protocols filling of the filling structures (either both filled simultaneously or one after the other) may be performed before, during or after radial expansion of the balloons and the scaffolding 127, 227 (either both expanded simultaneously or one after the other). Additionally, as discussed above with respect to FIG. 2, the scaffolds 127, 227 may be radially expanded using a cylindrically shaped balloon to form a substantially cylindrically shaped lumen. Curved, tapered or pre-shaped balloons may also be used to expand the scaffolds 127, 227, thereby forming a lumen that also is curved, tapered or shaped. The curved, tapered or pre-shaped balloon may be selected to match the anatomy of the vessel in which the scaffold and endograft is placed. Pre-shaped, curved or tapered balloons may be used in any of the other embodiments disclosed herein in order to obtain a desired lumen shape.

After filling the filling structures 112 and 212 as illustrated in FIG. 4E, the filling materials or medium will be cured or otherwise hardened as described in U.S. Patent Publication No. 2006/0212112 and the delivery catheters 114 and 214 removed, respectively. The hardened filling structures along with the expanded scaffolds 127, 227 will then provide a pair of tubular lumens opening from the aorta beneath the renal arteries to the right and left iliac arteries, as shown more clearly in broken line in FIG. 4F. The ability of the filling structures 112 and 212 to conform to the inner surface (S) of the aneurysm, as shown in FIG. 4F, helps the structures to remain immobilized within the aneurysm with little or no migration. Immobilization of the filling structures 112 and 212 may be further enhanced by providing any of the surface features described in U.S. Patent Publication No. 2006/0212112 which has been incorporated herein by reference.

The double filling structure embodiments will include at least one separate scaffold deployed within each of the tubular blood flow lumens. The scaffolds will generally be endoskeletal structures that lay the foundation for new lumens, and will be deployed within the tubular lumens of the double-walled filling structures using balloon or other expansion catheters (in the case of malleable or balloon-expandable scaffolds) and an optional retractable constraining sheath. FIG. 4G more clearly shows the first scaffold 127 disposed within the tubular lumen of the first filling structure 112 while a second scaffold 227 is disposed in the tubular lumen of the second filling structure 212. As illustrated, in this exemplary embodiment, the scaffolds are balloon expandable structures which extend into the iliac arteries IA at the lower end of the filling structures. In other embodiments, the scaffolds may be self-expanding stent-like structures fabricated from a shape memory alloy such as Nitinol.

Referring now to FIG. 4H, first and second scaffolds 127 and 227 may extend upwardly on the aortic side of the first and second filling structures 112 and 212. When the scaffold structures extend into the thoracic aorta TA, it will usually be desirable that they be expanded so that they conform to each other along a plane or region of contact. For example, as shown in FIG. 4I, the upper ends of the scaffolds 127, 227 may be formed preferentially to have D-shaped cross-sections when expanded, although other cross-sections such as elliptical, circular, etc. may be formed. Thus, flat faces 258 and 260 will engage each other with the remaining portion of the stent conforming to the inner wall of the aorta. In this way, most of the cross-sectional area of the aorta will be covered with the scaffold, thus enhancing blood flow through the filling structures. Other configurations are disclosed in U.S. Patent Publication No. 2006/0212112 previously incorporated herein by reference.

Figure 5:
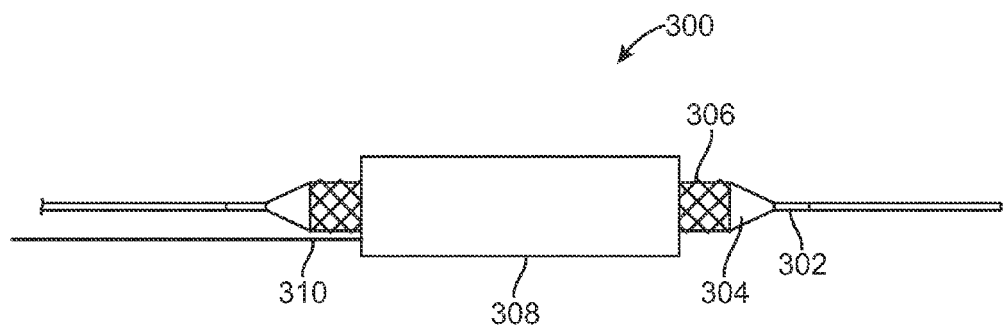
FIG. 5 illustrates an aneurysm treatment system having a filling structure and scaffold concentric with a delivery catheter.
Figure 29:
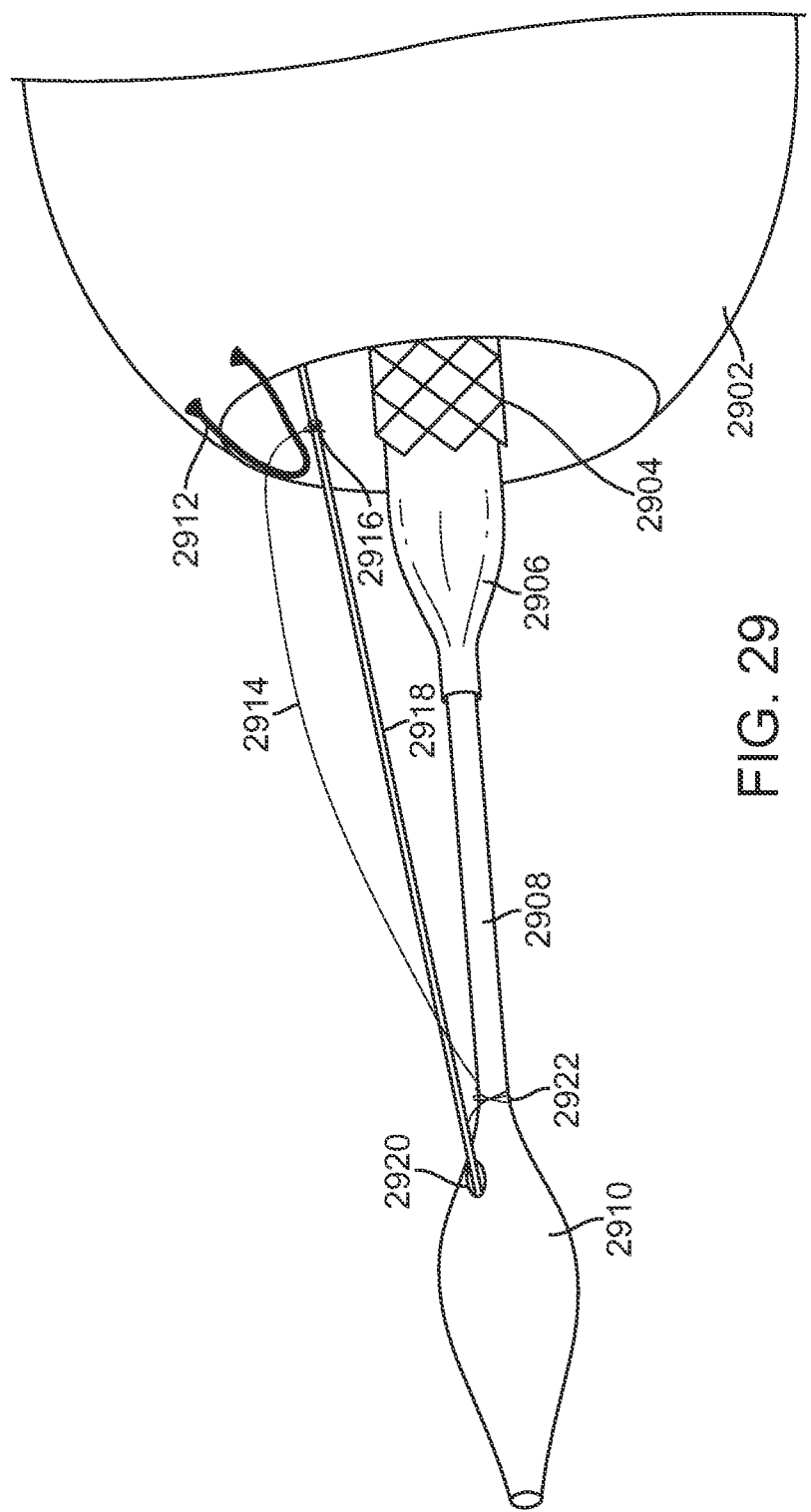
FIG. 29 illustrates the use of a tether to help minimize relative movement between a filling structure and an endoframe.
Figure 30A:
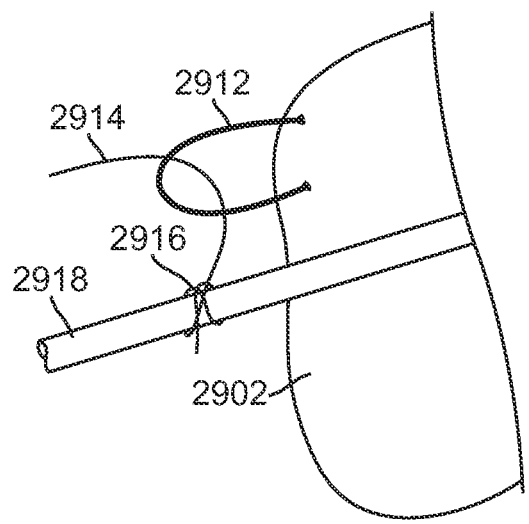
FIGS. 30A-30B illustrate use of a constrictor knot.
Figure 30B:
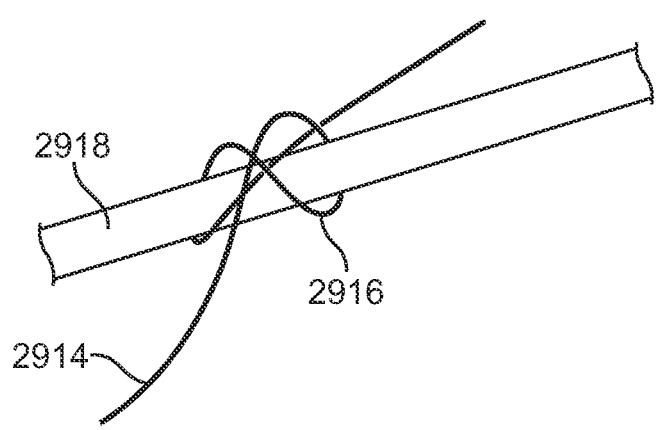

In the exemplary embodiment of FIGS. 4A-4I, the scaffold and filling structure are both disposed coaxially and generally concentrically over an expandable member coupled to a delivery catheter and the entire system is delivered to the aneurysm at one time. FIG. 5 shows a similar coaxial and concentric system 300 for treating aneurysms where a filling structure 308, also referred to as an endograft is coaxially disposed over stent-like scaffold 306, both of which are then coaxially and concentrically positioned over a radially expandable balloon 304 which is coupled to the distal region of a catheter shaft 302. Proximal and distal portions of scaffold 306 extend uncovered by filling structure 308 and a filling tube 310 allows a fluid to be delivered to the filling structure 308. While this embodiment is promising, in certain situations, the filling structure may move relative to the endoframe during delivery, thereby resulting in inaccurate placement of one or both devices. It would therefore be advantageous to provide a more effective way of coupling the filling structure with the endoframe to minimize such movement and to facilitate more accurate delivery of the scaffold and endograft to the treatment site. FIG. 29 illustrates an exemplary embodiment that employs a releasable coupling mechanism to help minimize such movement. In FIG. 29, the distal region of a delivery catheter having a filling structure and an endoframe disposed thereover is highlighted. Filling structure 2902 is disposed over an endoframe 2904, both of which are also disposed over a radially expandable balloon 2906 coupled to catheter shaft 2908. The distal end of catheter shaft 2908 includes an atraumatic tapered nosecone 2910 having a receiving aperture 2920. The releasable coupling mechanism includes a lockwire 2918 that runs substantially parallel with catheter shaft 2908, with the distal end of the lockwire 2918 disposed in the receiving aperture 2920 in nosecone 2910. The releasable coupling mechanism also uses a tether 2914. Tether 2914 is releasably coupled with the lockwire 2918, the filling structure 2912 and the catheter shaft 2908, thereby minimizing relative motion of the endoframe 2904 to the filling structure 2902 during delivery. The tether may be a thin wire fabricated from metal or a polymer or it may be a suture or other filament-like material. Coupling is accomplished by passing one end of the tether 2914 through a tether loop 2912 attached to the filling structure 2902 and one end of the tether is then releasably coupled with the lockwire 2918 using a releasable knot, here a constrictor knot 2916. Constrictor knots are well known in the art and may be seen in greater detail in FIGS. 30A-30B. The opposite end of the tether is secured to the distal region of the delivery catheter 2922 with a knot such as a constrictor knot, or bonded, welded or otherwise fixed to the catheter shaft. This configuration helps keep the filling structure 2902 from moving relative to the endoframe 2904 and the delivery catheter 2908 during delivery. FIG. 29 illustrates a single tether coupled with a single tether loop. Using the tether/pullwire coupling system, movement of the filling structure relative to the endoframe is limited to ±5 mm preferably, and more preferably to ±3 mm and the endoframe/filling structure can be positioned in the aneurysm to within ±7 mm of a target implantation site, and more preferably to within ±5 mm of the target site.

In use, once the filling structure 2902 and the endoframe 2904 have been delivered to a desired position, the lockwire 2918 may be retracted proximally so that its distal tip disengages from aperture 2920 and the lockwire is removed from under the constrictor knot 2916 allowing the knot to unfurl. This de-couples the endoframe 2902 from the delivery catheter 2908 so that the two may be separated from one another. One end of the tether remains coupled with the catheter so that the tether may also be removed from the body.

Figure 31:
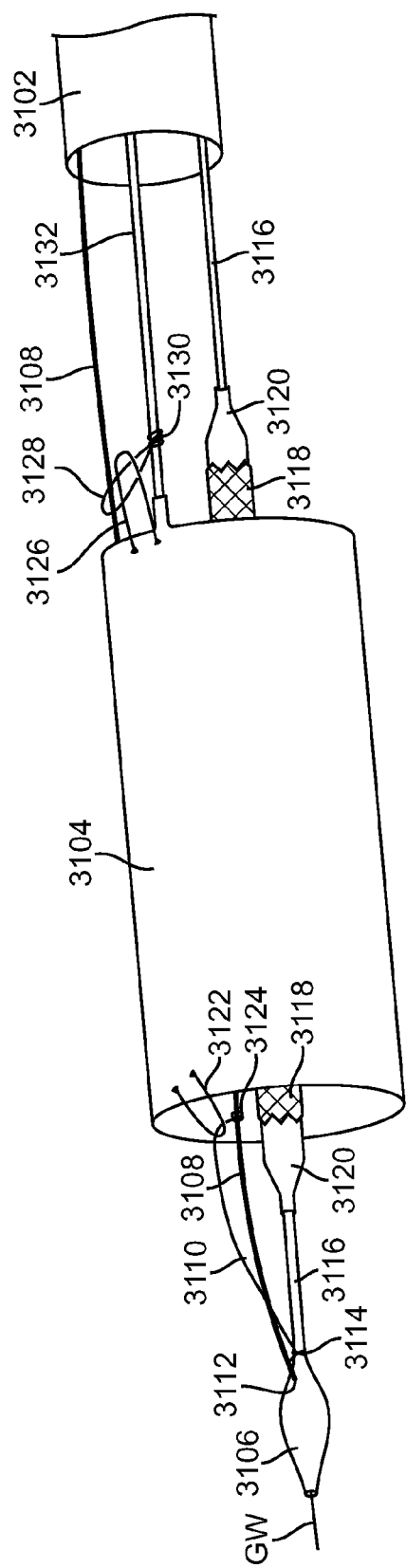
FIG. 31 illustrates use of two tethers.

The embodiment of FIG. 29 only illustrates a single tether. In other embodiments, multiple releasable coupling mechanisms using tethers may be coupled with multiple tether loops. For example, two, three, four or more releasable coupling mechanisms having two, three, four or more tethers may be disposed circumferentially and optionally symmetrically around the catheter and filling structure coupled with a matching number of tether loops coupled with the filling structure. In other embodiments, one, two, three, four, or more releasable coupling mechanisms using tethers may be coupled to both the proximal and distal ends of the filling structure with tether loops on the proximal and distal ends of the filling structure. FIG. 31 illustrates an exemplary embodiment of a device having two releasable coupling mechanisms including tethers. In FIG. 31 a delivery sheath 3102 is disposed over the endoframe 3118 and filling structure 3104 during delivery to the aneurysm, typically over a guidewire GW. Once delivered to the aneurysm, the endoframe 3118 and the filling structure 3104 are advanced and exposed from the delivery sheath 3102 (or the delivery sheath is retracted). Two releasable coupling mechanisms having two tethers 3110 and 3128 are used to help couple the filling structure 3104 with the endoframe 3118. A first tether 3110 passes through a tether loop 3122 attached to the filling structure 3104 while one end of the tether is releasably connected to the lockwire 3108 using a knot 3124 such as the constrictor knot previously disclosed above. The other end 3114 of the tether 3110 is coupled with a distal portion of delivery catheter 3116 or nose cone 3106. A second tether 3128 passes over the lockwire 3108 and through a second tether loop 3126 attached to the other end of the filling structure 3104. The second tether 3128 is then releasably coupled with the fill tube 3132 extending from the filling structure 3104 using a knot 3130 such as a constrictor knot. The fill tube 3132 allows the filling structure 3104 to be filled with hardenable medium from outside the patient's body. The lockwire 3108 runs substantially parallel with the delivery sheath 3102 and is disposed under the filling structure 3104. The distal end of the lockwire 3108 is releasably received in an aperture 3112 in tapered nosecone 3106 and the proximal end may be manipulated by the physician from outside the patient's body. In addition to helping prevent movement of the filling structure relative to the scaffold, the second tether 3128 helps to prevent release of the fill tube 3132 from the filing structure 3104, thus providing a fail safe mechanism prior to filling, and during filling or re-filling of the filling structure and until the procedure is over and it is desired to separate the filling tube from the filling structure. Endoframe 3118 is crimped over balloon 3120 which is coupled with the delivery catheter shaft 3116. In these exemplary embodiments, a tether is used in the releasable coupling mechanism to prevent unwanted movement of the filling structure relative to the scaffold. One of skill in the art will appreciate that other releasable coupling mechanisms may be used and therefore the coupling mechanism is not limited to tether embodiments. Additionally, the tether may be used as a releasable coupling mechanism in any of the embodiments disclosed in this specification.

The coupling mechanism described in FIG. 31 also allows positioning of the filling structure relative to the endoframe by movement of the delivery catheter, as illustrated in FIGS. 32A-32B. In FIG. 32A, depending on how taut the tethers 3110 and 3128 are, the delivery catheter 3116 may be advanced or retracted as indicated by the arrows to position the endoframe 3118 and delivery catheter 3116 relative to the filling structure 3104. Similarly, in FIG. 32B, the delivery catheter 3116 may be advanced into the filling structure 3104 or retracted away from the filling structure 3104 as indicated by the arrows. This embodiment may be used when in situ adjustment is desired or during "serial deployment" where either the filling structure or the endoframe is deployed before the other and then the two components are aligned in the aneurysm, as will be discussed in greater detail below. In addition to serial delivery of a scaffold and endograft, the releasable coupling mechanisms described herein (e.g. the tether embodiments described above) may also be used in parallel delivery of the two components as will be discussed in greater detail below. Thus, releasable coupling mechanisms such as tethers may be used in any of the embodiments disclosed herein. Sometimes, the lockwire will be covered with a support post. In FIG. 35, a loop 3514 coupled with the filling structure 3502 is fed into an aperture 3516 of a support post 3512. A lockwire 3510 is fed through the support post 3512 and through the loop 3514, thereby coupling the filling structure 3502 with the lockwire 3510. The distal end of the lockwire 3510 is received in an aperture 3508 on nosecone 3506 of the delivery catheter 3504. This configuration prevents the support post from having a free end that could extend and cause damage or trauma to the vasculature. Retraction of the lockwire 3510 past the aperture 3516 releases the loop 3514 from the lockwire 3510.

Figure 33:
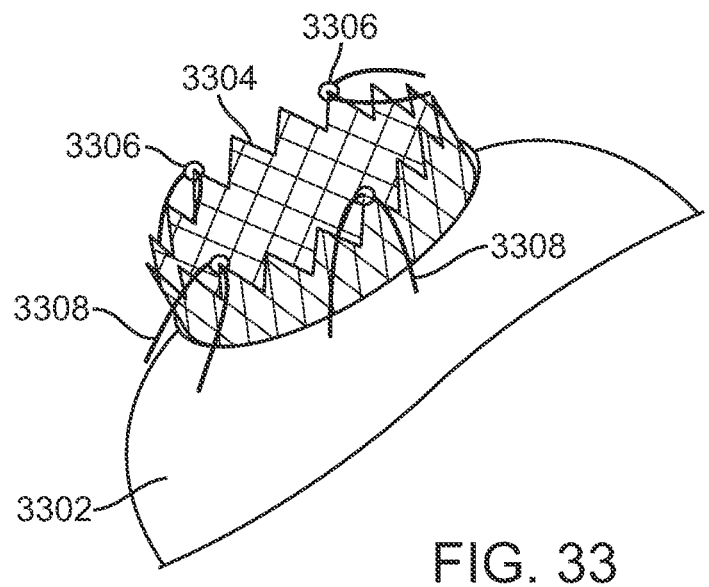
FIG. 33 illustrates coupling of the filling structure with the endoframe.

In other embodiments, the filling structure may be coupled more directly with the endoframe. For example, in FIG. 33, the endoframe 3304 includes eyelets 3306 near it's proximal and distal ends. Tether loops 3308 may then be looped through the eyelets 3306 and secured to the filling structure 3302. This way, the filling structure 3302 will be fixed relative to the endoframe as long as the tether loops are taut. Generally, this coupling mechanism will allow about ±5 mm and more preferably ±3 mm of relative movement between the filling structure and the endoframe. Also, the filling structure and endoframe should be positionable within ±7 mm and more preferably between ±5 mm of a target position within the aneurysm of the filling structure 3302.

Figure 34:
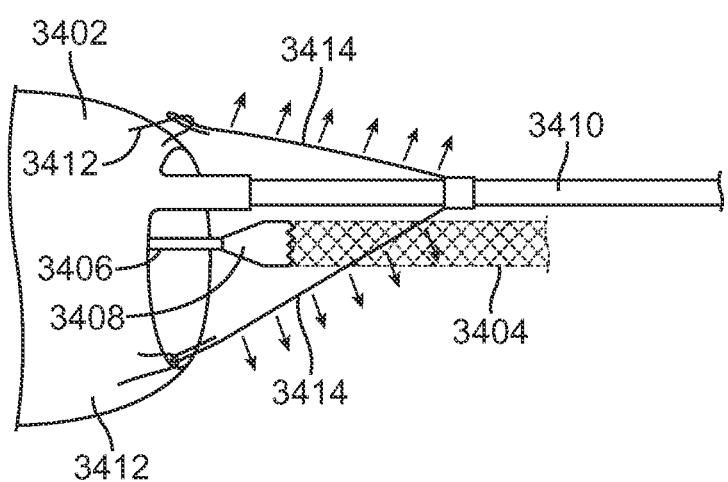
FIG. 34 illustrates the use of spring arms to help open a portion of the filling structure.

In place of tethers coupled with the filling tube (such as tether 3128 in FIGS. 32A-32B), spring loaded arms may be used. In FIG. 34, filling structure 3402 includes a filling tube 3410 for filling the filling structure with hardenable medium. A pair of spring arms 3414 are coupled with the filling tube 3410 at one end, and the opposite ends of the arms 3414 are coupled with the filling structure 3402. The ends are wrapped around a loop 3412 coupled with the filling structure 3402. In this embodiment, the arms are wire-like elements made from spring temper metal such as stainless steel or superelastic nitinol, although other materials could be used such as a resilient polymer. Since the filling structure is coupled with the filling tube, they are fixed to one another and relative movement is not possible. The arms 3414 are advantageous since upon deployment from a constraining sheath (not illustrated), the arms radially expand outward, facilitating opening of the filling structure so it is may receive the delivery catheter 3406 having an endoframe 3404 mounted over a balloon 3408. Again, this embodiment may be used when the filling structure and the endoframe are delivered separately, as discussed below.

In addition to the potential challenge of minimizing movement of the endoframe relative to the filling structure, the embodiment described in FIG. 5 may present other challenges. For example, because of the stackup of multiple elements on top of one another, the distal region of system 300 has a relatively large profile which can make it difficult to insert percutaneously into the patient's vasculature and in some cases (e.g. through tortuous vessels or through stenotic regions) it also is difficult to advance to the aneurysm. Therefore, other delivery system configurations are possible which may help reduce profile and facilitate delivery. These delivery systems have an outer diameter preferably ranging from 10 French to 18 French, and more preferably have an outer diameter ranging from 12 French to 16 French.

Figure 6:
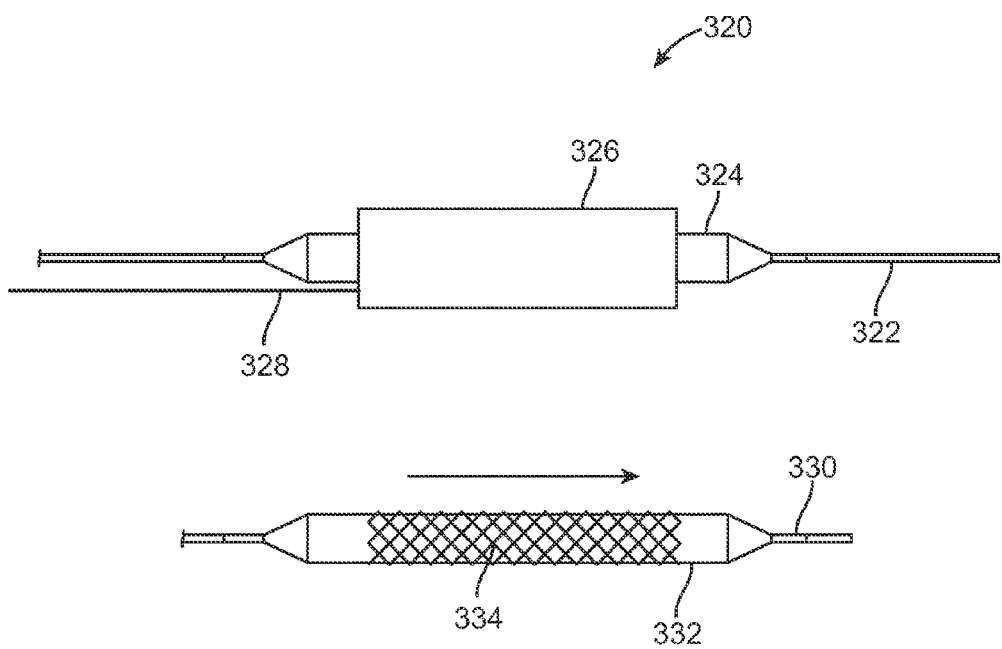
FIG. 6 illustrates an aneurysm treatment system wherein the filling structure is separate from the scaffold.

FIG. 6 illustrates an alternative embodiment where the system 320 utilizes independent delivery of the filling structure and the scaffold. In FIG. 6, a filling structure 326 is disposed over a balloon 324 which is coupled to a first delivery catheter 322. A filling tube 328 allows the filling structure 326 to be filled with a hardenable material. A second delivery catheter 330 carries a second balloon 332 having a scaffold 334 disposed thereon. In this embodiment, the endograft may be delivered to the aneurysm first where it is expanded and filled via filling tube 328 and then the first catheter 322 is removed from the filling structure 326. The second catheter 332 is then advanced into the lumen created by the filling structure 326 and then balloon 332 is expanded thereby correspondingly expanding scaffold 334 within filling structure 326. Alternatively, after filling structure 326 has been expanded and filled, delivery catheter 322 may be removed from the patient's body and scaffold 334 may be mounted on the same delivery catheter 322 for delivery and expansion into the filling structure 326. This alternative embodiment provides some advantages over the embodiment of FIG. 5 such as having a lower profile but still has challenges such as the increased cost and waste associated with using two separate delivery catheters or an increased procedure time to deliver and deploy the filling structure and scaffold independently of one another. One possible solution is to provide a delivery catheter having two independently expandable balloons disposed on a delivery catheter. The balloons are separated from one another by a predetermined distance. A scaffold is placed over one balloon and an endograft is placed over the second balloon. Thus, a single catheter may be used to deliver both the graft and scaffold to the aneurysm where the graft and scaffold are then independently deployed into the aneurysm.

Figure 7:
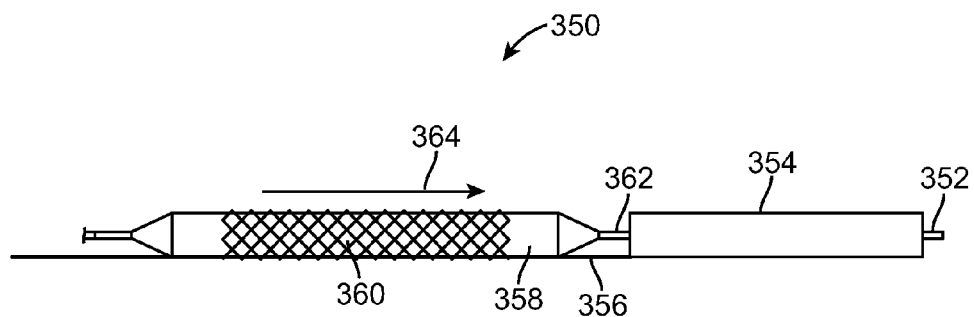
FIG. 7 shows an aneurysm treatment system having a filling structure axially separated from the scaffold.
Figure 8:
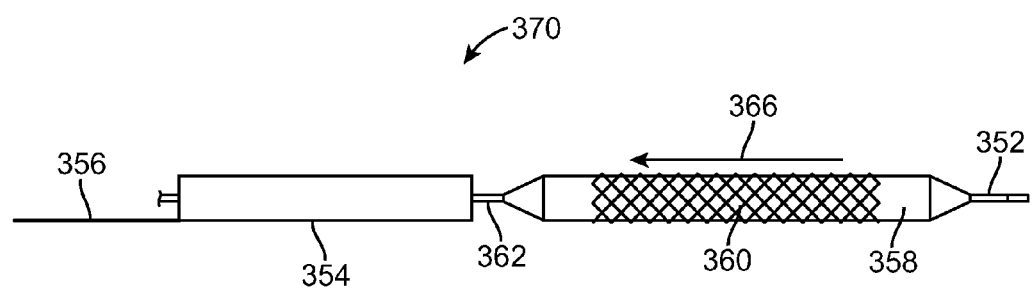
FIG. 8 illustrates an aneurysm treatment system similar to that of FIG. 7, but with the relative positions of the filling structure and scaffold reversed.

Another embodiment which reduces the need for two delivery catheters and also reduces procedure time by eliminating the need to remove the catheter from the patient and then mount a scaffold thereover is illustrated in FIG. 7. In FIG. 7, a single delivery catheter carries both scaffold and filling structure to the aneurysm while still providing a system with reduced delivery profile. Delivery system 350 includes a delivery catheter 352 having an expandable balloon 358. Scaffold 360 is mounted directly over the balloon 358 and the filling structure 354 is positioned distal to the scaffold 360 such that the two implants are axially separated from one another and a gap or spacing 362 separates them. The releasable coupling mechanisms described above, including the tether embodiments may be used to limit movement between the scaffold and the filling structure. The delivery catheter 352 may be advanced to the aneurismal treatment site such that filling structure 354 traverses the aneurysm. The filling structure 354 may be filled via filling tube 356 so that it conforms to the aneurysm and then scaffold 360 may be advanced distally in the direction of arrow 364 so that is received in the lumen of filling structure 354. Balloon 358 may then be radially expanded so as to expand scaffold 360 into the inner wall of filling structure 354. In an alternative embodiment, after filling structure 354 is positioned across the aneurysm, scaffold 360 may be advanced into the lumen of filling structure 354. Both are then radially expanded by expansion of balloon 358 and the filling structure is filled either before, during or after radial expansion. System 370 of FIG. 8 is similar to that of system 350 in FIG. 7 except that the relative positions of the scaffold 360 and filling structure 354 have been reversed. This time, in the embodiment of FIG. 8, scaffold 360 is retracted proximally in the direction of arrow 366 into the lumen of filling structure 354. One of ordinary skill in the art will appreciate the motion of the components is relative, thus instead of advancing a first component into a second component, the second component may be retracted over the first component. Similarly, retraction of a first component into a second component may also be achieved by advancing the second component over the first component.

Figure 9:
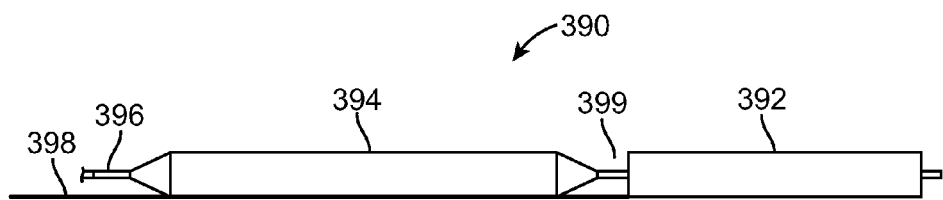
FIG. 9 illustrates an aneurysm treatment system having a filling structure axially separated from the radially expandable balloon.

Yet another embodiment that helps reduce delivery profile is illustrated by system 390 in FIG. 9. In FIG. 9, a filling structure 392 having filling tube 398 is disposed over delivery catheter 396 and axially separated from radially expandable balloon 394 by a spacing 399. In this embodiment, the filling structure 392 may be delivered to the aneurysm where it is filled and balloon 394 is expanded to help form the lumen in filling structure 392. Alternatively, the filling structure may be retracted over balloon 394 either before, during or after delivery to the aneurismal treatment site and then it may be expanded and filled. A separate scaffold (not illustrated) may then be delivered and deployed in the lumen created by the inner wall of filling structure 392. A releasable coupling mechanism, such as the tether embodiments previously described above may also be included in this embodiment to minimize movement of the filling structure relative to the scaffold.

Some delivery systems may include a sheath. Any of the embodiments previously described may include a sheath in order to protect the scaffolding and/or the filling structure. In some embodiments where the scaffolding is self-expanding, the sheath acts as a constraint to keep the scaffolding from self-expanding. FIG. 10A illustrates a delivery system having a balloon 406 disposed over a catheter shaft 404. A balloon expandable scaffolding 408 is disposed over the balloon 406 and a filling structure 410 is also disposed over the catheter shaft 404 axially separated from the balloon 406. An outer sheath 402 is disposed over both the scaffolding 408 and the filling structure 410. Moving the sheath 402 away from the scaffolding 408 exposes the scaffolding 408 and/or filling structure 410 so that either may be radially expanded by balloon 406 or allows expansion of filling structure 410 due to filling. FIG. 10A also illustrates an optional pusher tube 412 having a distal end that can engage the proximal end of the endograft. The pusher tube keeps the endograft from moving as the outer sheath 402 is retracted and also helps to support the endograft and prevent it from collapsing during sheath retraction. The pusher tube 412 and the sheath 402 may be extruded using manufacturing techniques well known to those of ordinary skill in the art and may be fabricated from a number of polymers such as polyethylene, polyurethane, Teflon, PVC, nylon and the like.

Figure 10B:
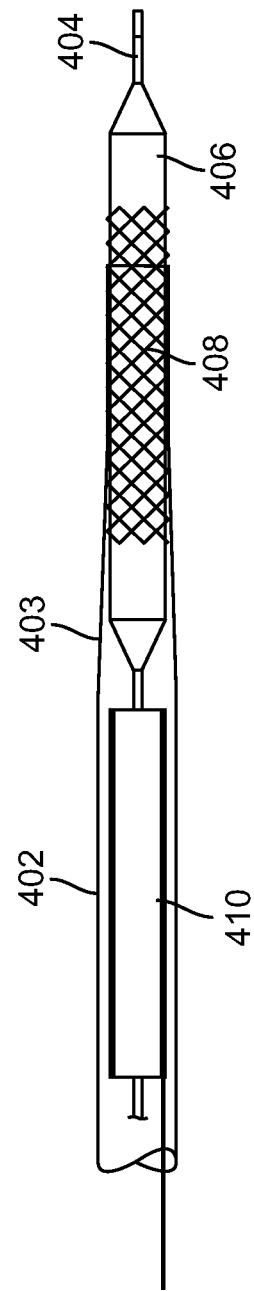

FIG. 10B illustrates another sheath embodiment similar to the embodiment of FIG. 10A, except in this embodiment the sheath has a tapered distal end. Because the balloon 406 and scaffolding 408 are distal relative to the filling structure 410 and because of the larger profile of the endograft filling structure 410 relative to the scaffolding 408, a step exists between the filling structure 410 and the scaffolding 408. Tapered region 403 in sheath 402 provides a smoother transition between these two regions. In order to facilitate retraction of the sheath over the filling structure 410, the tapered tip 403 may be perforated or longitudinally slit. Thus, as sheath 402 is retracted and as the tapered region 403 begins to engage filling structure 410, the slits or perforations will open up allowing the smaller diameter sheath tip to pass over the filling structure 410. In a preferred embodiment, two slits approximately 180 degrees apart may be imparted into the sheath tip, although it will be recognized that additional slits or even a single slit may be used.

Other variations on the orientation of the balloon, filling structure and scaffolding may also be employed. For example, in some embodiments the endoframe scaffolding and filling structure may be mounted coaxially over a catheter shaft either proximal of or distal to a balloon. The scaffolding and filling structure are positioned at the treatment site and then the balloon is positioned within the scaffolding and filling structure and expanded. In a variation of this embodiment, a thin split tubular liner may be positioned over the balloon and passes through the inner diameter of the filling structure. The thin liner acts as a guide for the balloon during use. Thus, as the balloon is axially positioned within the scaffolding and filling structure, the thin liner guides the balloon through the inner diameter of the scaffolding. When the balloon is expanded, the thin liner splits along perforations or slit regions to allow radial expansion thereof.

For example, in FIGS. 36A-36B, a smooth sheath or covering 3608 may be disposed over all or a portion of the endoframe 3606 and balloon 3610. This is useful in embodiments where the endoframe 3606 and catheter shaft 3604 are advanced into the filling structure 3602 (e.g. FIG. 7) or where the endoframe 3606 and catheter shaft 3604 are retracted into the filling structure (e.g. FIG. 8). Covering all or a portion of the balloon 3610 and endoframe 3606 allows both to easily be received into the filling structure 3602 without binding or damaging either component. When the balloon is inflated, the cover 3608 will be pushed away from and off the endoframe 3606 and balloon 3610, allowing full expansion as seen in FIG. 36B.

Figure 37:
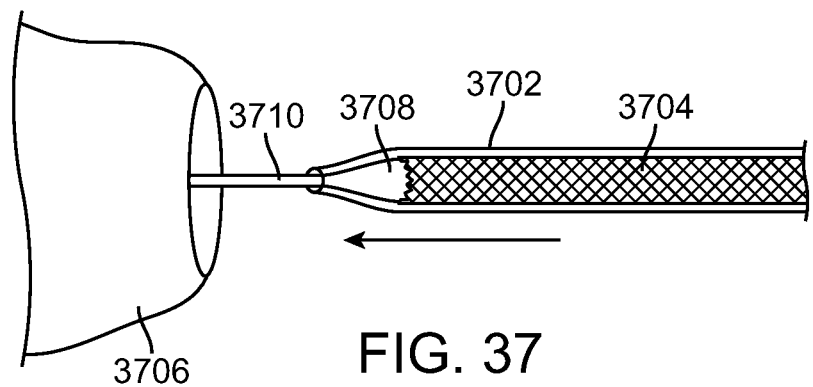
FIGS. 37-38 illustrate still other embodiments using a sheath.
Figure 38:
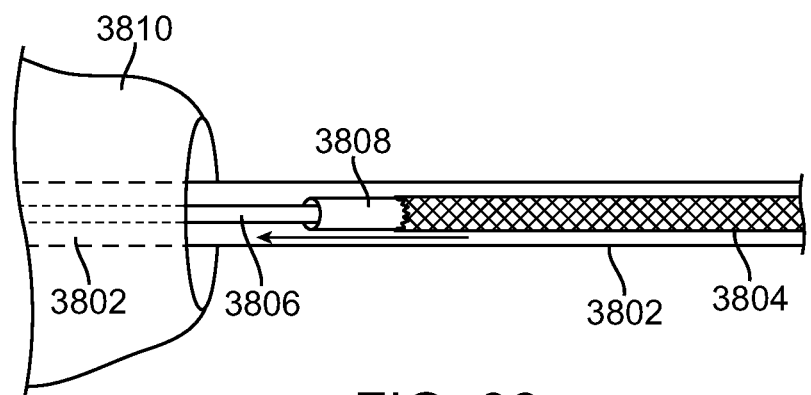

FIG. 37 illustrates another embodiment using a sheath or cover. In FIG. 37, the entire endoframe 3704 and balloon 3708 are covered by the sheath 3702 to facilitate smooth entry of the endoframe 3704 into the filling structure 3706 when the catheter shaft 3710 is moved in the direction of the arrow. FIG. 38 illustrates still another embodiment using a sheath. In FIG. 38, a sheath or sleeve 3802 not only covers the endoframe 3804 and balloon 3808, but extends all the way through the filling structure 3810. Thus, when the delivery catheter 3806 is advanced, the endoframe 3804 easily slides through the sleeve 3802 and avoids rubbing against the inner wall of the filling structure 3810. The sleeve 3802 may then be easily retracted and removed prior to deployment of the endoframe and filling structure.

Figure 52C:
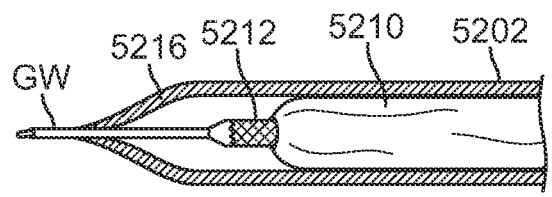
Figure 52D:
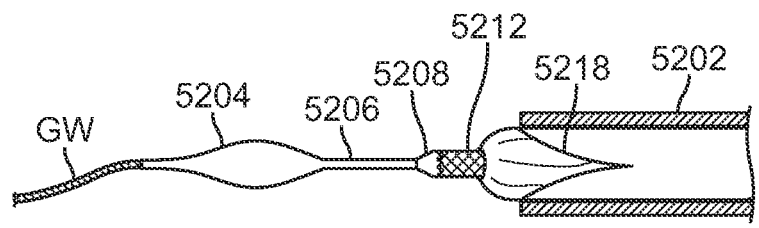

A split sheath or a perforated sheath may also be used to facilitate deployment of the device. For example, FIG. 52A illustrates a filling structure 5210 having a filling tube 5214 disposed over a scaffold 5212 which is carried by a balloon 5208 on a delivery catheter shaft 5206 having a distal nosecone 5204. The delivery catheter is delivered over a guidewire GW and covered with a sheath 5202 during delivery. Upon deployment, the sheath 5202 is retracted and the filling structure 5210 is filled and endoframe 5212 is expanded with balloon 5208. The delivery catheter 5206 is then retracted away from the expanded endoframe 5212 and expanded filling structure 5210 as seen in FIG. 52B. In some situations, the physician may desire to further expand the endoframe 5212 with a larger size balloon. This requires that the delivery catheter 5206 be removed and replaced. However, the nosecone 5204 cannot be retracted into the sheath 5202 due to interference with the filling tube 5214. A tapered split sheath or a tapered perforated sheath may be used to overcome this challenge. FIG. 52C illustrates a tapered split sheath 5216. The tapered split sheath 5216 allows for a smaller nosecone 5204, which can pass through the sheath. Because the sheath 5216 is tapered at the tip, it must split to pass over the filling structure 5210. This allows the delivery catheter to be retracted from the patient and replaced with a different catheter having a different balloon size for post-dilation of the endoframe.

In other embodiments, a tether line may be used to help guide movement of the filling structure relative to the scaffolding. FIGS. 11A-11B illustrate the use of such a tether line. In FIG. 11A, a delivery system 420 includes an elongate flexible shaft 422 having a balloon 430 disposed near the distal end of the shaft 422. A stent-like scaffolding 432 is carried by the balloon 430. A filling structure 436 with filling tube 438 is also disposed over shaft 422. Filling structure 436 has four eyelets 434 which serve as guides for tether lines 428 to pass through. Tether lines 428 extend from the proximal end of delivery system 420, through eyelets 434 and are coupled to nosecone 426. Nosecone 426 is coupled to shaft 424 which is movable relative to shaft 422. Shaft 422 is retracted over shaft 424 such that balloon 430 and scaffold 432 are slidably received by filling structure 436. FIG. 11B shows retraction of scaffolding 432 into filling structure 436 with a longer length of shaft 424 exposed. Tether lines 428 help guide the filling structure 436 so that it mates with scaffolding 432 and is retracted into the filling structure 432. In this exemplary embodiment, four eyelets 434 are used, although more or less may also be used. The eyelets 434 may be integral with the filling structure 436 or they may be separate components bonded or otherwise attached thereto. Once the scaffolding has been retracted into a desired position within filling structure 436, the tether lines 428 may be pulled from nosecone 426 and away from the filling structure 436 so that it may be expanded and filled in the aneurysm.

FIGS. 12A-12B illustrate an alternative embodiment of a system 450 employing tether lines. In FIGS. 12A-12B, tether lines are used to pull the filling structure toward the scaffolding so that the two components are properly aligned. In FIG. 12A, a catheter shaft 456 carries a balloon 460 disposed near the shaft's distal end and a scaffolding 462 is disposed over the balloon. A nosecone 454 is coupled to the distal end of shaft 456 and a filling structure 452 having a filling tube 464 is disposed over the catheter shaft adjacent the balloon 460 and scaffold 462. The nosecone has a taper 457 on the proximal end as well as an optional taper on the distal end, that way the nosecone helps guide the catheter as it is being advanced through the vasculature and the proximal taper helps the catheter pass through the filling structure as the catheter is being retracted away from the filling structure. Tether lines 458 are removably coupled to filling structure 452 and extend distally to nosecone 454. Tether lines 458 extend through nosecone 454 and then extend proximally through a lumen in shaft 456 (not shown) until the tether lines 458 exit the proximal end of the catheter shaft 456. As the proximal portion of tether lines 458 are pulled proximally away from the aneurysm, filling structure 452 is advanced until it is properly positioned over the scaffolding 462 and balloon 460. The tether lines may then be pulled free from filling structure 452 and pulled into nosecone 454 as seen in FIG. 12B. The filling structure 452 and scaffold 462 may then be filled and expanded into the aneurysm. In an alternative embodiment, the shaft 456 and scaffolding 462 may be retracted into filling structure 452.

A hitch may also be used to move the filling structure relative to the scaffolding. FIGS. 22A-22B illustrate an exemplary embodiment of a hitch. In FIG. 22A eyelet or suture loop 702 is coupled with a filling structure 712 (FIG. 22B). Here, one loop is disclosed, although additional suture loops may also be used. The suture loop 702 is used to hitch the filling structure 712 with a hypotube 760 so that the filling structure may be advanced. Hypotube 706 runs substantially parallel with the delivery catheter shaft (not illustrated here). A distal portion of the hypotube 706 is skived 708 to create a receptacle for receiving the suture loop 702. A lockwire 704 passes through the hypotube 706 and through the suture loop 702, thereby locking the suture loop 702 to the hypotube 706. When the hypotube 706 is advanced distally suture loop 702 is tensioned and thus, the filling structure may be advanced distally over the scaffolding 710. Once the filling structure 712 is placed in the desired position relative to scaffolding 710, the lockwire 704 may be refracted proximally from the hypotube 706 releasing the suture loop 702 from the skived region 708. The hypotube 706 and lockwire 704 may then be retracted away from the filling structure 712 and removed from the patient.

Figure 23A:
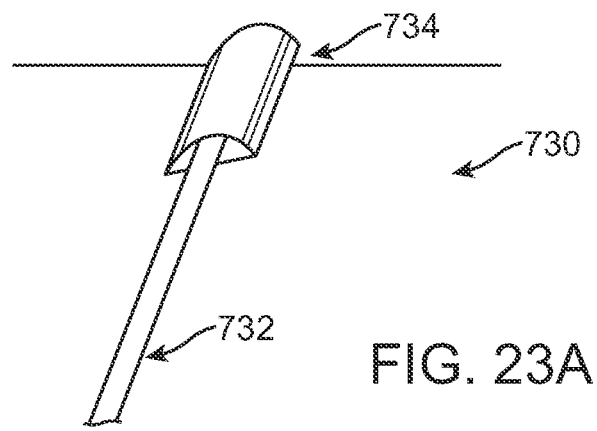
FIGS. 23A-23C illustrate a pocket feature on the filling structure.
Figure 23B:
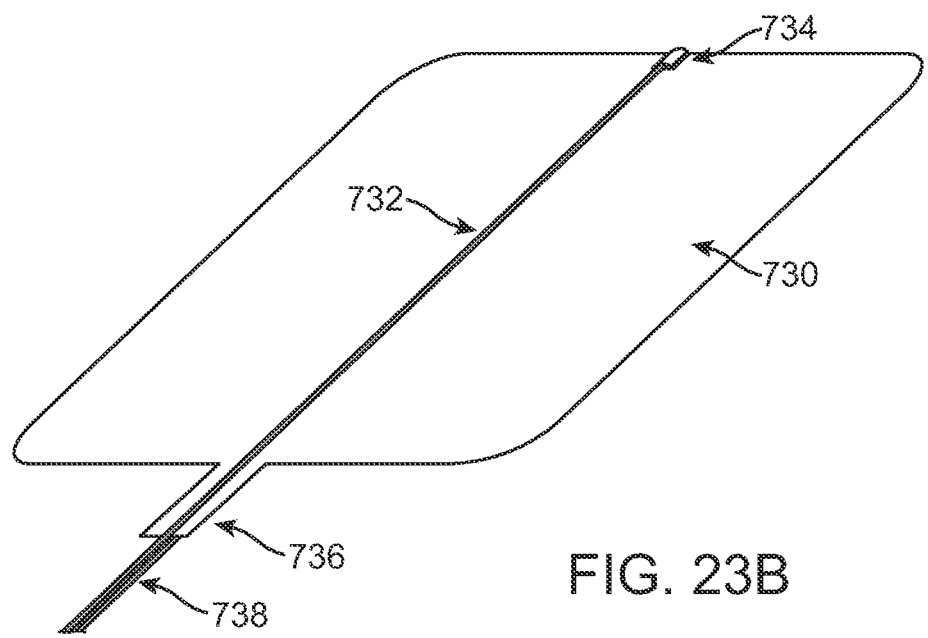
Figure 23C:
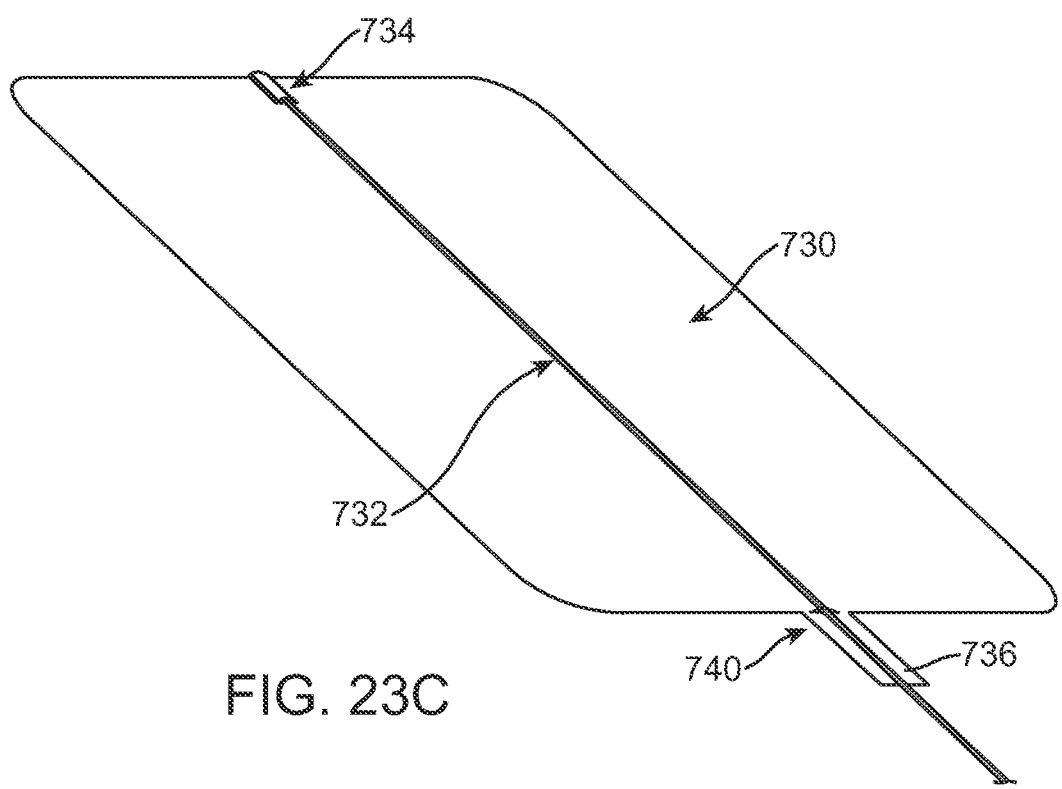

Sometimes, it may be desirable to increase the columnar strength of the endograft in order to prevent it from buckling or otherwise collapsing. Suturing the endograft to the scaffold may be used to help keep the two structures coupled together. Some embodiments utilize wires or metal frames in the filling structure or attached thereto in order to provide additional support. A pocket or receptacle on the filling structure may also provide enhanced column strength. FIGS. 23A-23C illustrate an exemplary embodiment with a pocket.

In FIG. 23A, filling structure 730 comprises a pocket or receptacle formed in a wall of the filling structure 730, near its distal end. The pocket 734 may be made from the same material as the filling structure 730, or it may be another resilient material. The pocket 734 is generally closed along three sides and has one end open, preferably proximally oriented. The opening is sized to slidably receive a tensioning tube, rod or hypotube 732. In use, the tensioning tube 732 is inserted into the pocket 734 until it's distal end bottoms out. FIG. 23B shows the tensioning tube 732 traversing the unrolled, flattened filling structure 730 substantially parallel to the longitudinal axis thereof. A filling tab 736 is coupled with a proximal end of the filling structure 730 and a filling tube 738 is fluidly connected to the filling tab 736. The filling tube 738 extends proximally so that the filling structure 730 may be filled from outside the patient's body. The filling tube 738 may be used to apply tension to the proximal end of the filling structure 730 and thus the filling structure 730 is captured between the pocket 734 on the distal end of the filling structure 730 and the filling tube 738 on the proximal end. In an alternative embodiment, the proximal end of the filling structure 730 may utilize the hitch previously disclosed in FIGS. 22A-22B. FIG. 23C shows a pocket 734 on the distal end of filling structure 730 and a suture loop 740 on the proximal end of filling structure 730. Tensioning tube 732 is inserted into pocket 734 and also uses the hitch of FIGS. 22A-22B to capture suture loop 740. In either embodiment, once the filling structure is delivered to the treatment site, filled and deployed, the tensioning tube 732 may be retracted from the pocket 734 and the hitch released, thereby disengaging the tensioning tube 732 from the filling structure 730.

Figure 24:
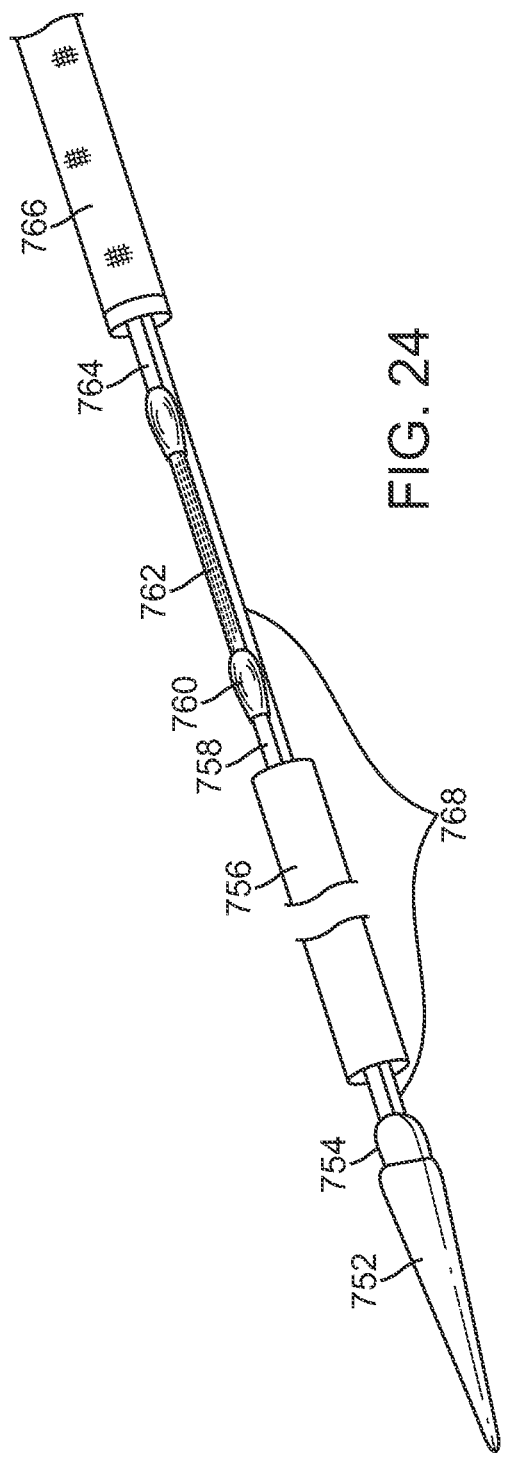
FIG. 24 shows an alternative embodiment of a filling structure and scaffolding delivery system.

Another exemplary embodiment of a filling structure and scaffolding delivery system is seen in FIG. 24. In FIG. 24, a delivery catheter has a nosecone 752 attached to a center shaft 758 via a tip 754 member. An endograft filling structure 756 is positioned coaxially over the center shaft 758. Also coaxial to the center shaft 758 and proximal to the filling structure 756 is a sliding shaft 764 which can slide axially along the center shaft 758. Attached distally to the sliding shaft 764 is an expandable member 760, here a balloon, which has a stent-like scaffolding 762 crimped thereover. Coaxial to both shafts 758, 764 is an outer sheath 766 which has an inner diameter large enough to contain both shafts 758, 764, the balloon 760, scaffolding 762 and filling structure 756. A pullwire 768 runs substantially parallel to the longitudinal axis of the shafts 758, 764, outside of the balloon 760 and scaffolding 762 and through the inner diameter of the filling structure 756. The pullwire 768 is removably coupled to the filling structure 756 at two or more positions. In use, the outer sheath 766 is retracted to expose the filling structure 756. The balloon 760 and scaffolding 762 are advanced over the center shaft 758 by advancing the sliding shaft 764, through the inner diameter of the filling structure 756 until the balloon 760 and scaffolding 762 are axially aligned with the filling structure 756. The balloon 760 may then be inflated, radially expanding the scaffolding 762 within the filling structure 756. The filling structure 756 may then be filled with a hardenable material and the pullwire 768 is retracted to release the filling structure 756 from the shaft 758 and the delivery catheter may then be removed from the patient.

Figure 41A:
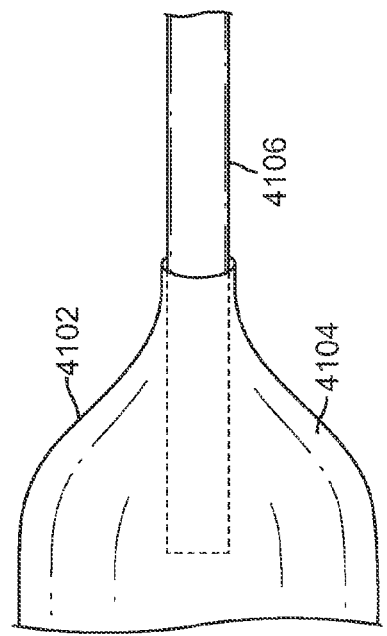
FIGS. 41A-41B illustrate separation of a filling tube from the filling structure.
Figure 41B:
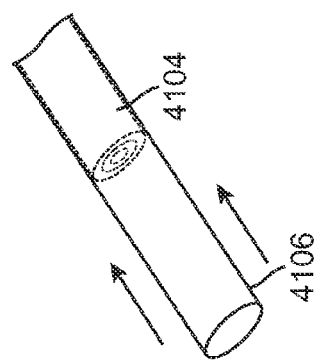
Figure 40:
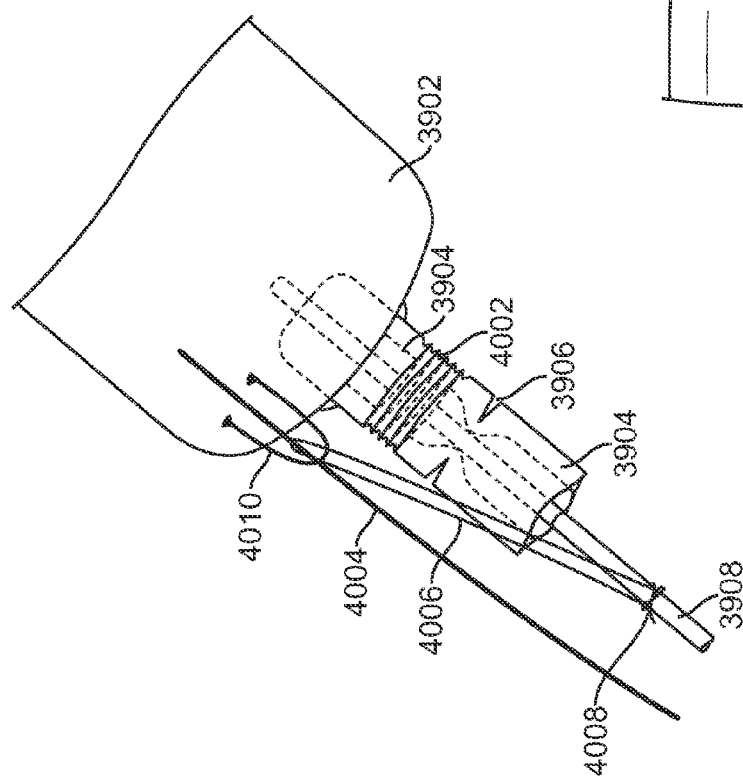
FIG. 40 illustrates an embodiment of a filling tab.
Figure 42:
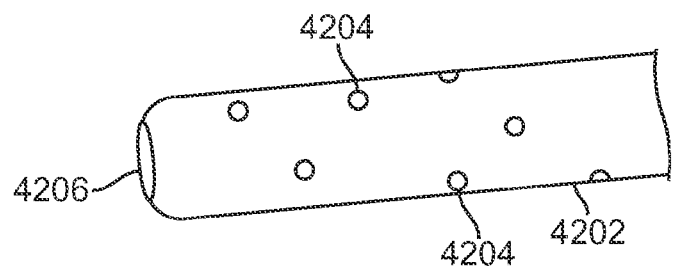
FIG. 42 illustrates filling ports in the filling tube.
Figure 43:
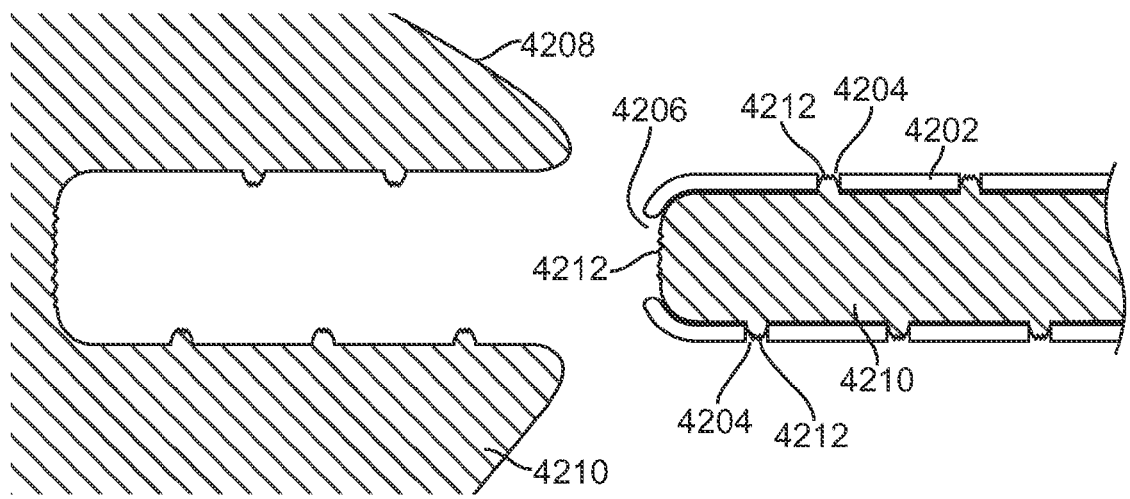
FIG. 43 illustrates separation of a filling tube from the filling structure.
Figure 44:
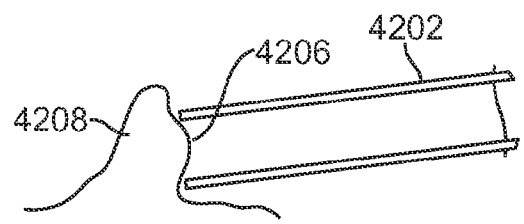
FIG. 44 illustrates blockage of a filling tube.

Many of the filling structure embodiments include a filling tube. FIG. 41A illustrates an embodiment where a single lumen filling tube 4106 may extend from the filling structure 4102 proximally so that the filling structure may be filled with a hardenable medium by a physician using a syringe, pump or other filling device. Once the filling structure is filled with hardenable medium 4104, the filling tube 4106 may be retracted and pulled away from the filling structure 4102. In some circumstances, the hardened filling medium 4104 may form a plug or tail 4108 that extends outside of the filling structure 4102. This is undesirable since the tail 4108 could break free and migrate or it could puncture or otherwise cause trauma to adjacent tissue. FIG. 41B illustrates the remaining tail 4108 after the filling tube 4106 has been released from the filling structure 4102. One embodiment that minimizes or eliminates this challenge is seen in FIG. 42. In FIG. 42, the distal portion of the filling tube 4202 has a distal port 4206 and a plurality of side ports 4204 for delivering the hardenable medium to the filling structure. Additionally, the distal end of the filling tube 4202 has a tapered and rounded tip which reduces the diameter of the plug once hardened, creating a break point when the plug is removed. FIG. 43 illustrates retraction of the filling tube 4202 away from the filling structure 4208 after hardening of the filling medium 4210. Because the filling medium is provided by multiple ports, several smaller plugs 4212 result and because of their smaller size, they easily break away from the filling material 4210 in the filling structure 4208 without leaving sharp protrusions. The polymer plugs remain inside the fill tube and break at the ports, instead of leaving a protruding tail. Additionally, having multiple ports 4204 is advantageous since the filling structure 4208 could be drawn into the lumen and block the distal portion 4206 during draining of the filling structure which can involve the use of a vacuum. The additional ports 4204 allow filling medium to be removed and/or delivered even if the distal port 4206 is blocked.

Figure 45A:
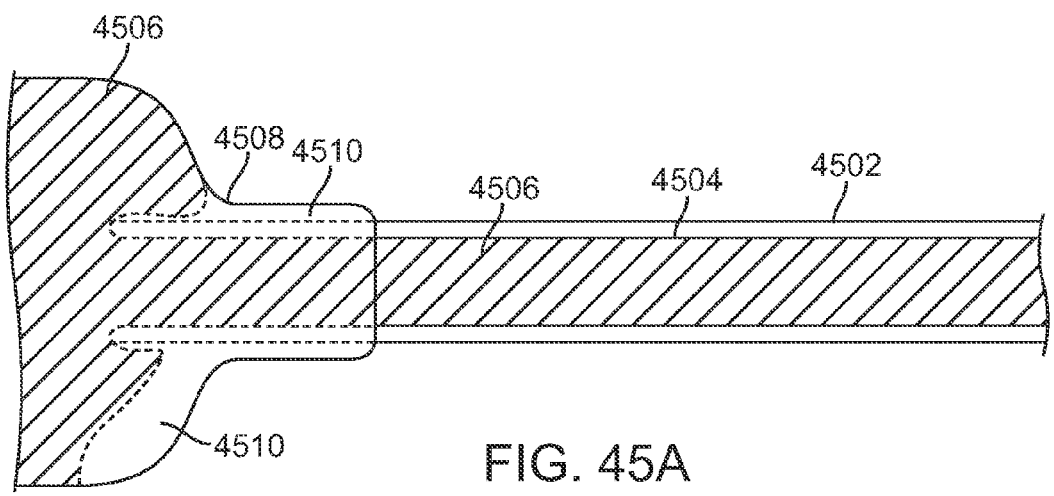
FIGS. 45A-45C illustrate the use of an inner and an outer filling tube.
Figure 45B:
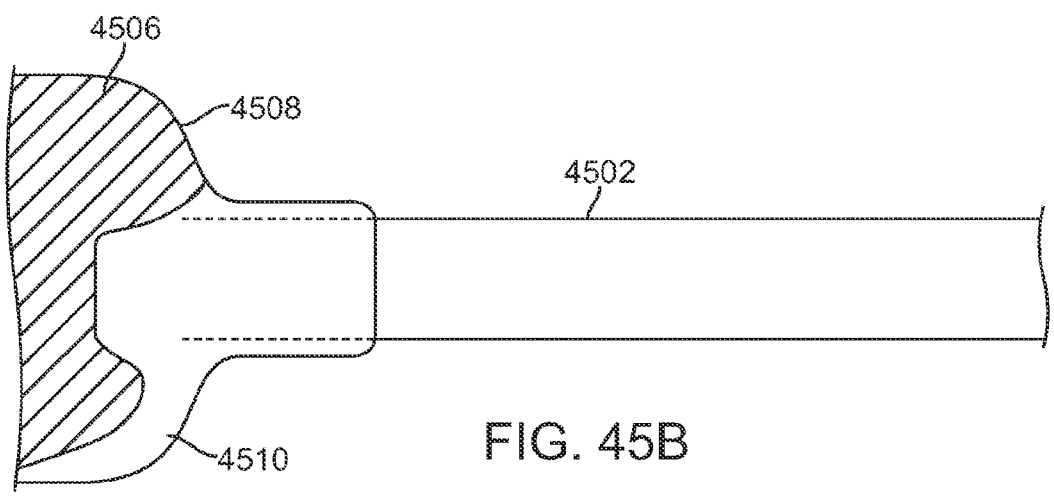
Figure 45C:
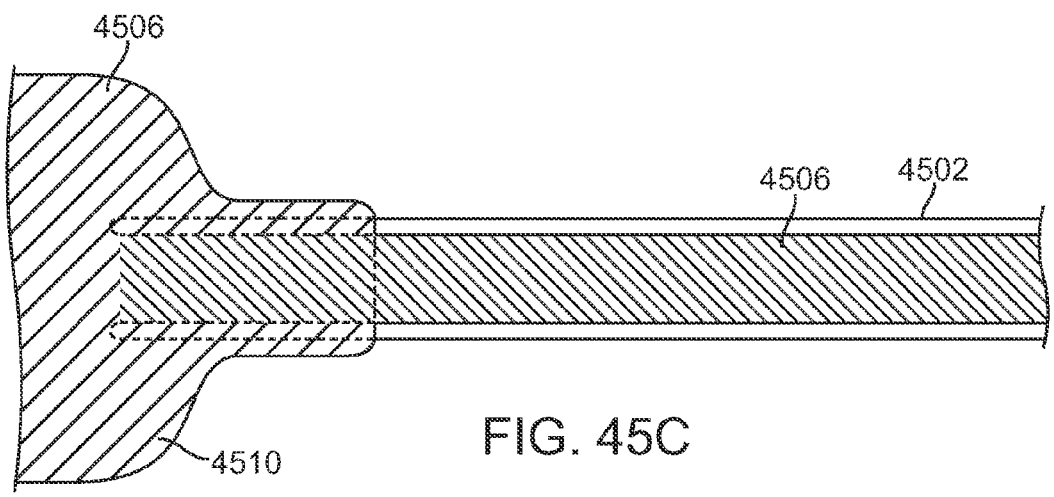

A double filling tube may be used to avoid some of the challenges discussed above. In FIG. 45A an outer filling tube 4502 has an inner filling tube 4504 extending along its length. The distal ends of both filling tube are disposed in the filling structure 4508. Filling medium 4506 can be delivered to the filling structure 4508 first, via the inner filling tube 4504. The inner filling tube may be retracted from both the filling structure 4508 and the outer filling tube 4502 after filling material has been delivered 4508 as seen in FIG. 45B. The filling structure does not always completely fill up with filling medium due to a number of reasons such as viscosity, stagnation around the filling tubes, etc. More commonly, the filling structure may not be completely filled up because the physician may not infuse an adequate volume of filling medium. Thus there may be unfilled regions 4510. Additional filling medium 4506 may be added to the filling structure 4506 using the outer filling tube 4502 or a new inner filling tube may be advanced through the outer filling tube 4502. This allows the unfilled regions 4510 to be more completely filled as seen in FIG. 45C.

Figure 46A:
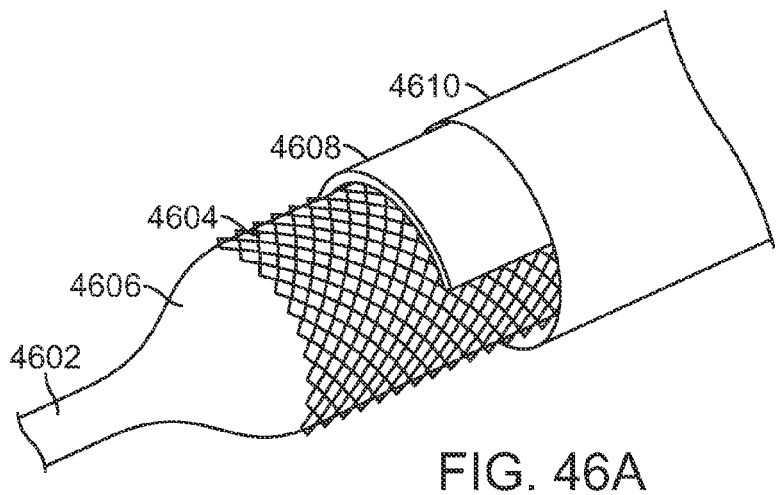
FIG. 46A-46C illustrate various filling tube geometries.
Figure 46B:
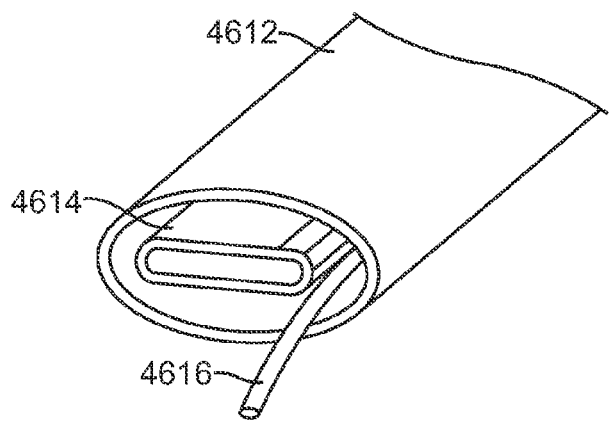
Figure 46C:
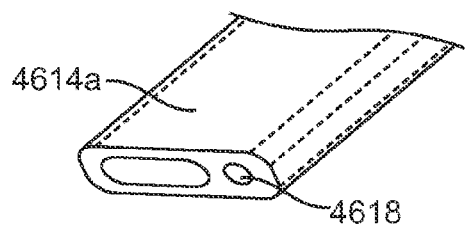

The filling tubes may have many geometries. They may be round, rectangular or other configurations. Generally, it is preferred that the filling tubes have a low profile in order to maintain a low delivery diameter of the entire system. For example, in FIG. 46A the filling tube 4608 has a width greater than its height. This allows the filling tube to more easily fit in the annular space between the inner surface of a filling structure or outer sheath 4610 and the endoframe 4604 which mounted over a balloon 4606 on a delivery catheter 4602. FIG. 46B illustrates nesting of an inner filling tube 4614 in an outer filling tube 3612 with an optional wire mandrel or stylet 4616 which may be used to prevent kinking of the filling tubes. In some embodiments, a filling tube 4614a may have a separate lumen 4618 for a stiffening mandrel. FIG. 47A illustrates an exemplary embodiment of a delivery system where the filling structure 4702 is axially separated from the endoframe 4712 and a sheath 4704 covers both during delivery. The endoframe 4712 is mounted over a balloon 4710 coupled to a catheter shaft 4708. FIG. 47B illustrates a cross section of FIG. 47A taken along the line B-B and highlights the low profile filling tube 4706 in the annular space between the sheath 4704 and the endoframe 4712. Once the sheath 4704 is retracted and the endoframe is advanced into the filling structure 4702, pressure in the filling tube 4706 will force open the filling tube 4706 and permit greater fluid flow.

It can be challenging to maintain an airtight seal between the filling structure and the removable filling tube. Additionally, when the filling medium hardens, it can be challenging to separate the filling tube from the filling structure after in situ curing. FIGS. 39A-39C illustrate one embodiment that facilitates separation of the filling tube from the filling structure while maintaining the required airtight seal. In FIG. 39A a filling tab 3904 is attached to filling structure 3902. The filling tab 3904 may be the same material as the filling structure 3902 or a different material. The filling tab may be welded, bonded, integral with, or otherwise attached to the filling structure. Filling tab 3904 has a perforation 3906 in it to allow for easy separation. Filling tube 3908 runs through filling tab 3904. A duck bill valve (not illustrated) or other one-way valve may also be incorporated into the fill tab to prevent filling medium leakage. After the filling structure 3902 has been filled and hardened, filling tube 3908 is pulled away from the filling structure 3902. The perforation 3906 allows the fill tab to easily tear away from the filling structure as seen in FIG. 39B and then the fill tube is removed from the filling structure, leaving only a small portion of filling tab 3904 connected to the filling structure 3902, as illustrated in FIG. 39C. In some situations, it may be advantageous to provide some slack in the fill tab. For example, when the filling structure is coupled with the fill tube 3908 using a tether 4006, lockwire 4004, constrictor knot 4008, tether loop 4010 (such as described above), the fill tab may be corrugated 4002 or additional material may be bunched together to allow expansion. The corrugation 4002 provides some slack in the fill tab 3904 to prevent unwanted detachment of the fill tube 3904 at the perforation 3906 when the fill tube 3908 is moved relative to the filling structure 3902. Once the lockwire 4004 is removed from the tether 4006, the tether 4006 is de-coupled from the tether loop 4010 and then the fill tab 3904 may be separated at the perforation 3906.

Various modifications of the protocols described above will be within the scope of the present invention. For example, while some of the scaffolds have been shown as being delivered at the same time as deployment of the filling structure(s), it will also be possible to deliver the scaffolds after deployment of the filling structures. The scaffolds could be delivered on the same or different delivery catheter(s) used to deliver and/or shape the filling structures. The scaffolds could then be expanded before, during or after filling the filling structure.

Pressure monitoring can also be performed at various stages of the aneurysm repair procedure to help control the filling process of the filling structure. The monitoring of pressures serves to reduce the risk of dissection, rupture or damage to the aneurysm from over-pressurization and also can be used to determine an endpoint for filling. Monitoring can be done before, during or after filling and hardening of the filling structure with filling medium. Specific pressures which can be monitored include the pressure within the internal space of the filling structure as well as the pressure in the space between the external walls of the filling structure and the inner wall of the aneurysm. A composite measurement can also be made combining pressures such as those measured within the interior space of the filling structure, together with that in the space between the external walls of the structure and the aneurysm wall or other space at the aneurysm site and an external delivery pressure used by a fluid delivery device, such as a pump or syringe, to deliver the filling medium. Control decisions can be made using any one of these pressure measurements or a combination thereof. U.S. patent application Ser. No. 11/482,503 discloses a number of pressure measuring embodiments, the entire contents of which are incorporated herein by reference.

Figure 48A:
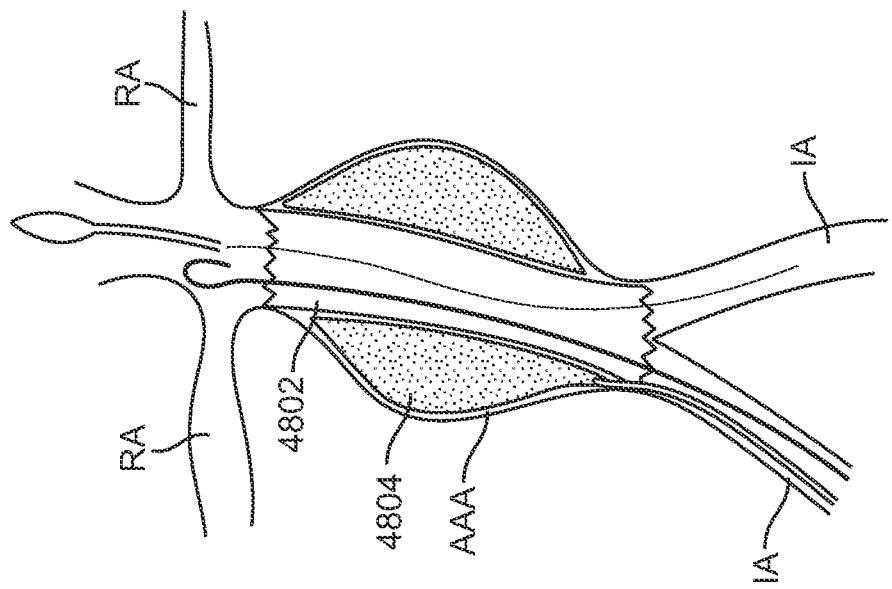
FIGS. 48A-48B illustrate the use of pressure monitoring during treatment of an aneurysm.
Figure 48B:
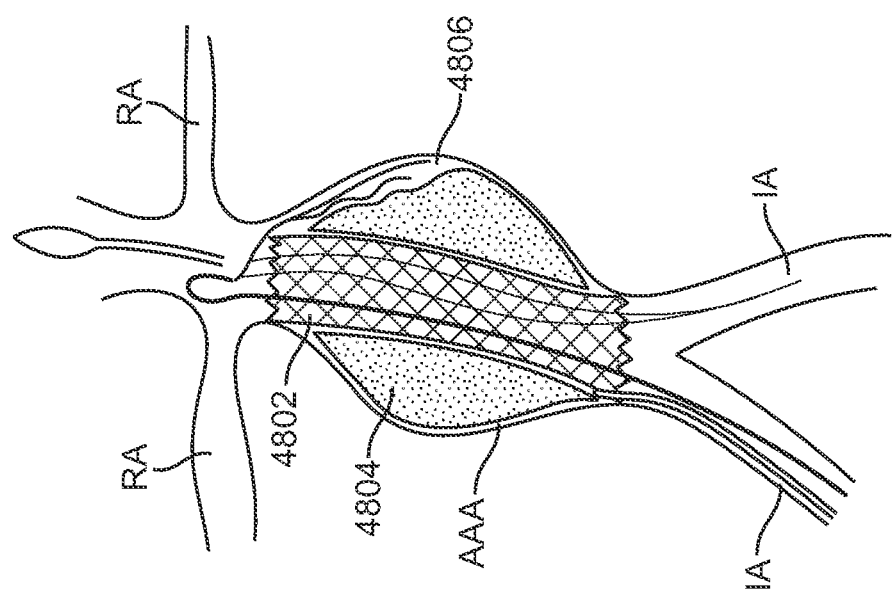

For example, in FIG. 48A, an endoframe 4802 and filling structure 4808 are positioned in the aneurysm AAA. After preliminary expansion of the endoframe 4802 and filling of the filling structure 4803 with saline or other fluid, contrast media may be injected into the aneurysm and observed under fluoroscopy. If a leak is observed 4806 around the filling structure, the physician may add additional saline or fluid to the filling structure until the leak is no longer observed as illustrated in FIG. 48B. The saline may then be removed from the filling structure. The volume of filling medium and pressure used to obtain this result are recorded and then used when the filling structure is filled with the hardenable filling medium. An exemplary embodiment of a delivery system capable of treating the aneurysm and providing the contrast media to the aneurysm is illustrated in FIG. 49. In FIG. 49, a filling structure 4906 having a filling tube 4914 is mounted over an endoframe 4914 which in turn is disposed over a balloon 4916 coupled with the delivery catheter shaft 4918. A wire 4910 is coupled with a nosecone 4908 on the distal end of the delivery catheter 4918. The wire 4910 is used to guide an angiography catheter, here a single lumen tube 4912 around the filling structure 4906. During delivery to the aneurysm, the entire system is housed in a delivery sheath 4902. While disposed in the sheath, the angiography catheter 4912 is proximal to the filling structure 4906 in order to keep profile to a minimum. Once near the device has been advanced to the aneurysm, the sheath 4902 may be refracted proximally thereby exposing the angiography catheter and filling structure. The angiography catheter 4912 may be advanced distally over the wire 4910 so that contrast media may be delivered upstream of the filling structure or between the aneurysm wall and the filling structure.

Similar to the filling tube, the angiography catheter should also have a low profile but it's lumen should also have as large a cross-sectional area in order to allow easy, low pressure delivery of contrast media at very high flow rates, 500-1,000 cc/minute. FIG. 50A illustrates one possible embodiment for an angiography catheter. In FIG. 50A, the angiography catheter 5010 has a flat, crescent shaped profile that lays flat and can fit in the annular space between the scaffold 5006 and the filling structure 5008. The scaffold 5006 is carried by a balloon mounted near a distal end of the delivery catheter 5002. FIG. 50B illustrates another embodiment where the delivery catheter 5002 includes a guidewire lumen. The lumen is large enough to accommodate a guidewire GW and still allow delivery of contrast media. In some embodiments, the distal end of the catheter 5002 may include a nosecone 5012 having side ports 5014 that allow the contrast media to exit laterally, as well as the distal port 5016.

In an exemplary method of deploying a filling structure and scaffolding, pressure monitoring may be utilized in the following way. After two filling structures have been delivered to the treatment site, both scaffolds are radially expanded to help create a lumen for blood flow through the filling structure across the aneurysm. Using data from a patient's computerized tomography (CT) scans, a fill volume of the aneurysm treatment site may be estimated and then divided by two, half for each of the two filling structures. This represents the baseline filling volume for each filling structure and is the minimum volume of filling material to be injected into each of the filling structures. Syringes or other injection devices coupled with a pressure gage may be used to optionally pre-fill each filling structure with contrast material using the baseline volume and the resulting baseline fill pressure may be noted. This allows unfurling of the filling structure and provides a preliminary assessment of how the expanded filling structures fit into the aneurismal space. Once this is accomplished, the contrast material is removed from the filling structures. Again using the patient CT data, a functional fill volume may be determined. This volume is a percentage of the aneurysm volume obtained from the CT data, or it may be a predetermined number and is the volume of filling material that effectively seals and excludes the aneurysm. Functional fill pressure will be the pressure at which the functional fill volume is attained. A polymer fill dispenser may then be used to fill each filling structure with the functional fill volume and the functional fill pressure is noted. While holding the functional fill volume and pressure, the filling structure may be observed under fluoroscopy to check for proper positioning, filling and the absence of leakage across the aneurysm. If leaks are observed, additional polymer may be added to the filling structures until the leaks are prevented or minimized. Excessive additional polymer should not be added to the filling structure in order to avoid exceeding a safe fill volume or safe fill pressure. Once the physician is satisfied with the filling and positioning of the filling structures, stopcocks to the filling structures may be closed to allow the polymer to harden and then the delivery devices may be removed from the patient.

Figure 13A:
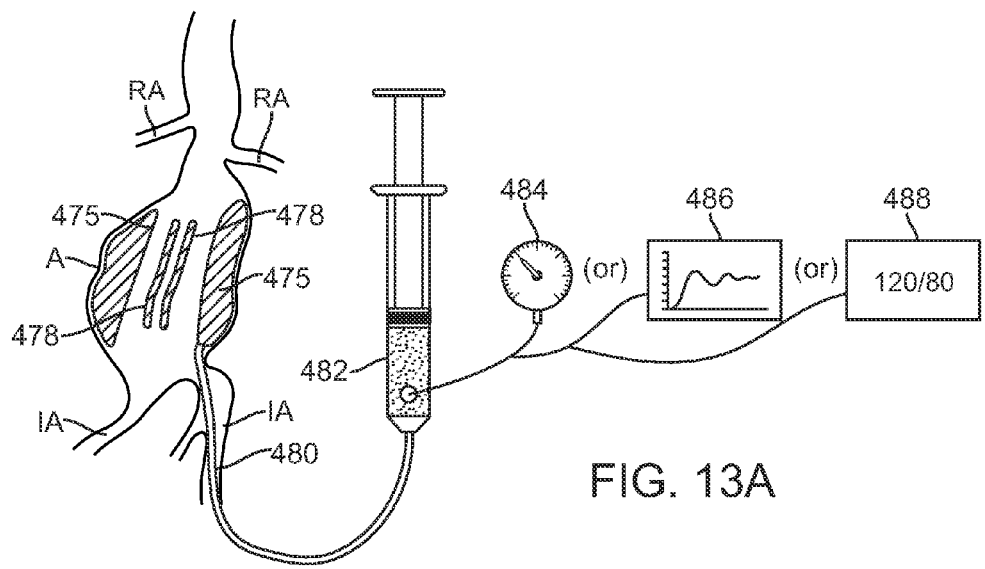
FIGS. 13A-13D illustrate the use of pressure monitoring to facilitate filling of the filling structure.
Figure 13B:
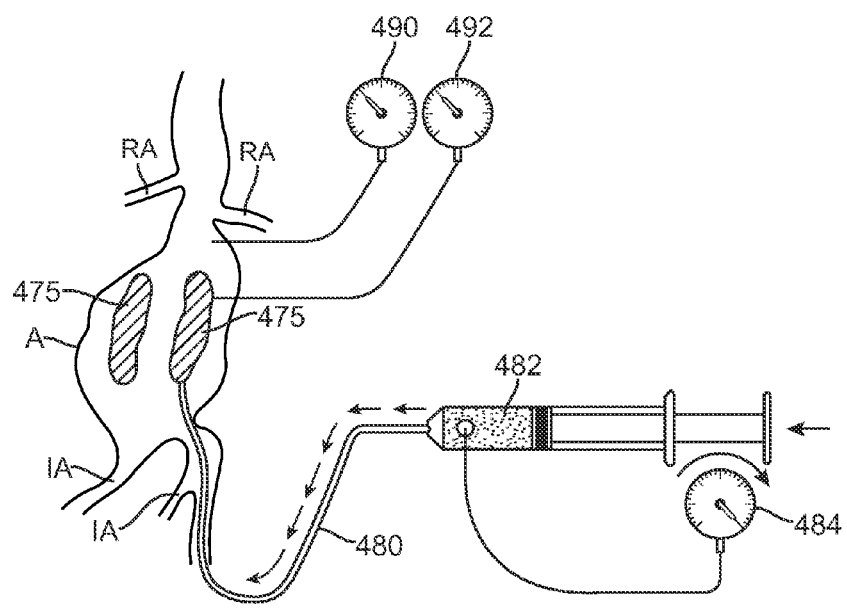
Figure 13C:
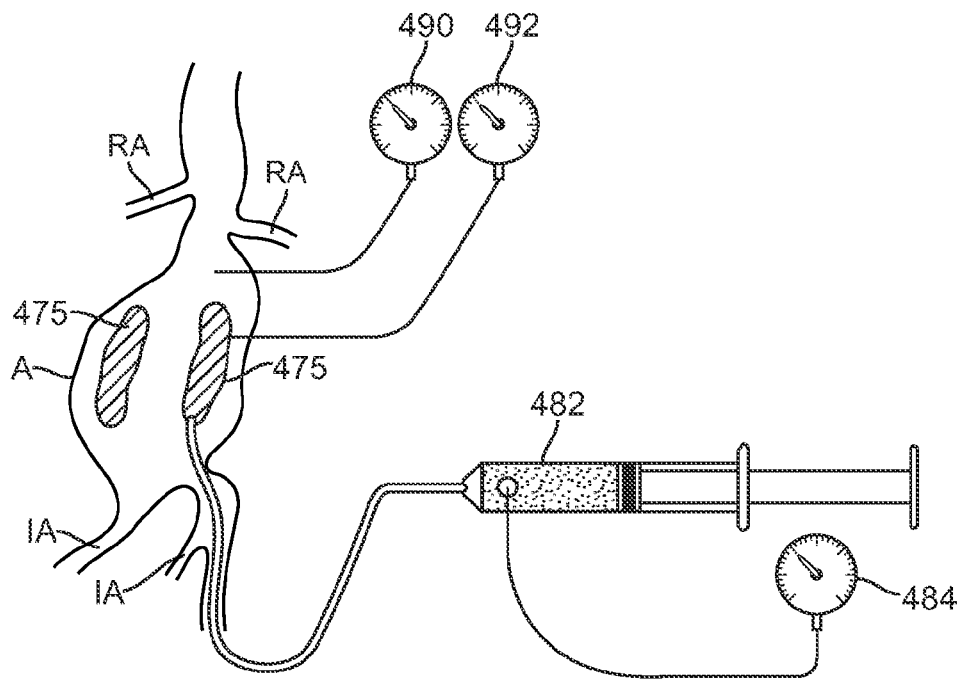
Figure 13D:
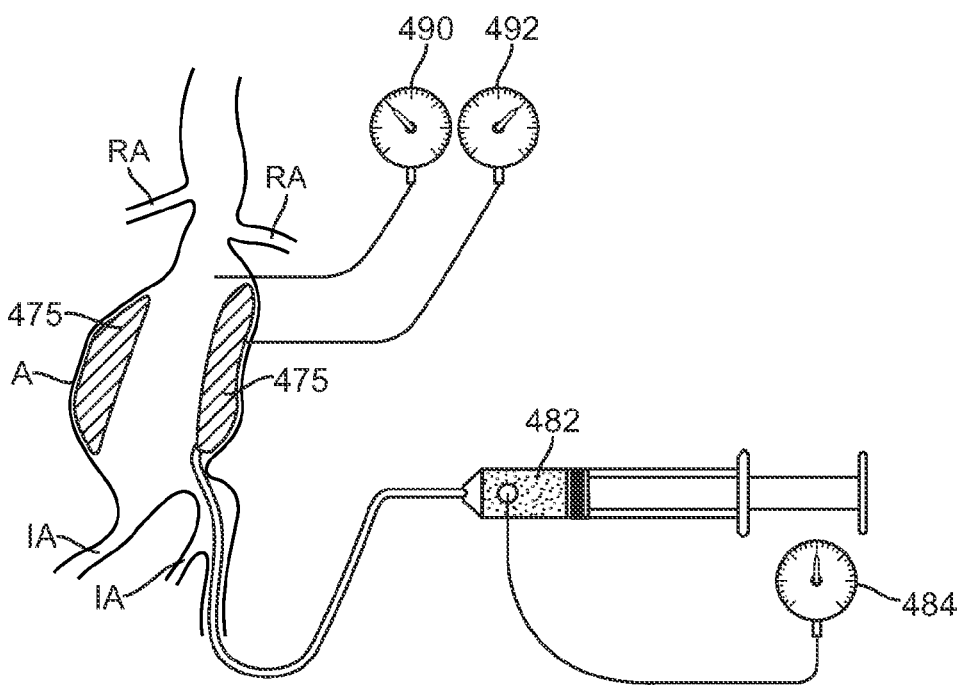

FIGS. 13A-13D illustrate an exemplary method of directly monitoring pressure in the filling structure to help ensure that it is properly inflated relative to the aneurysm. In FIG. 13A, a filling structure 475 is placed in the aneurysm A and scaffolding 478 provides support to the lumen created by filling structure 475 so that blood may flow from above the aneurysm into the iliac arteries IA A syringe 482 containing a filling material such as polyethylene glycol (PEG) is fluidly coupled to the filling structure 475 via fluid line 480. Filling pressure may be monitored in a number of ways including using a pressure gage 484 coupled to syringe 482, a graphical pressure monitor 486 or a blood pressure cuff 488. In FIG. 13B, as syringe 482 is actuated, the pressure will spike and the PEG will be injected into the filling structure 475. A pressure relief valve may be used to eliminate or reduce the spiking or electronic filtering may be used to remove the unwanted spike. Due to the viscosity of the PEG, as the polymer is being injected, the pressure will rise in the syringe 482 as measured by gage 484 relative to the pressure in the filling structure 475 as measured by gage 492 and also relative to the blood pressure as indicated by gage 490. This pressure will rise until high enough to move the PEG through the fluid line 480 into the filling structure 475 against the pressure of the blood 490. During filling, filling pressure 484 measured at the syringe 482 by gage 484 is equivalent to blood pressure measured at gage 490 and within filling structure 492, and this is illustrated in FIG. 13C. As the filling structure 475 fills and begins to expand into engagement with the aneurysm wall A, filling pressure measured by gage 484 will increase again. This time syringe pressure will also match pressure in the filling structure 492, both of which will be greater than the blood pressure 490, as seen in FIG. 13D.

Figure 14A:
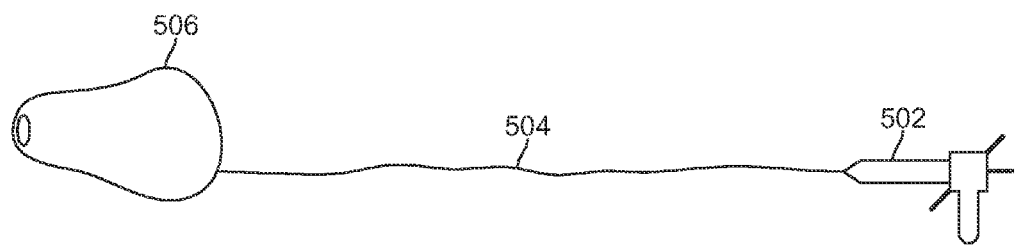
FIG. 14A-14C illustrate the use of a pressure relief valve and overflow reservoir.
Figure 14B:
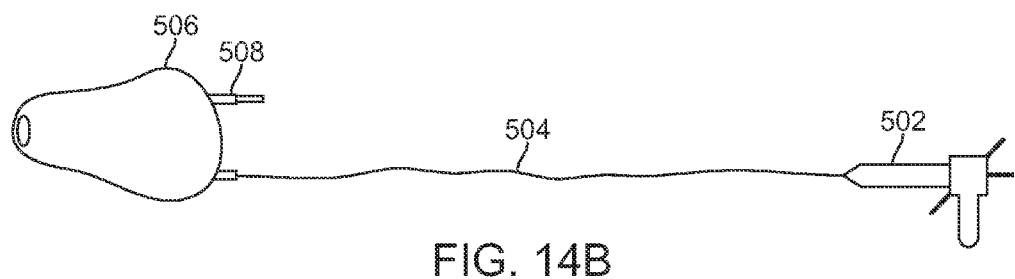
Figure 14C:
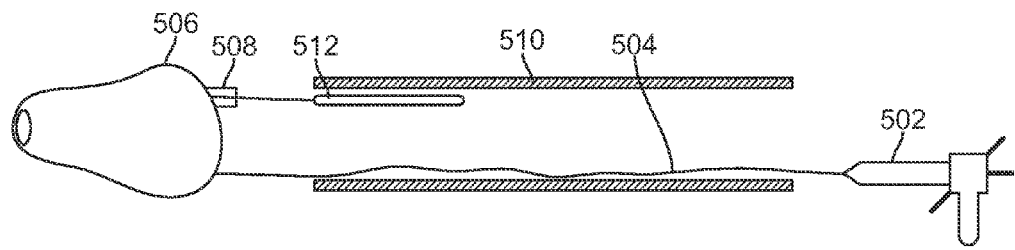

In addition to actual pressure monitoring by gages and graphical displays, etc., other pressure indicators may also be used to facilitate determining the filling status of the filling structure. FIGS. 14A-14C show an exemplary embodiment employing a relief valve. In FIG. 14A, a filling device 502 is used to fill filling structure 506 via fluid line 504. As filling device 502 is actuated, fluid will be delivered to the filling structure 506. Initially, there will be a pressure spike at the filling device 502 end of the system and because of this spike, the higher pressure drives the fluid filling medium into the filling structure 506. The pressure spike also makes it challenging to use an over-pressure relief valve to prevent over pressurizing the filling structure. However, a relief valve may be located closer to the filling structure end thereby reducing the potential for unintentional bleeding of the system due to pressure spikes. In FIG. 14B, a relief valve 508 is coupled to filling structure 506. The relief valve is preset to a certain pressure such that beyond the preset pressure, any additional filling material will bleed out of the filling structure. While the relief valve may be adjacent the filling structure, preferably the filling material will be vented toward the proximal end (handle end) of the catheter, outside the body. This keeps potentially dangerous fluids or other filling material from being introduced into the body. In another embodiment seen in FIG. 14C, when fluid bleeds out of relief valve 508 it fills a reservoir 512 which may be disposed either in or alongside catheter shaft 510. As reservoir 512 fills with filling medium, it is observed under fluoroscopy or other imaging modalities and when filled, the operator knows to stop filling the filling structure 506.

Figure 25A:
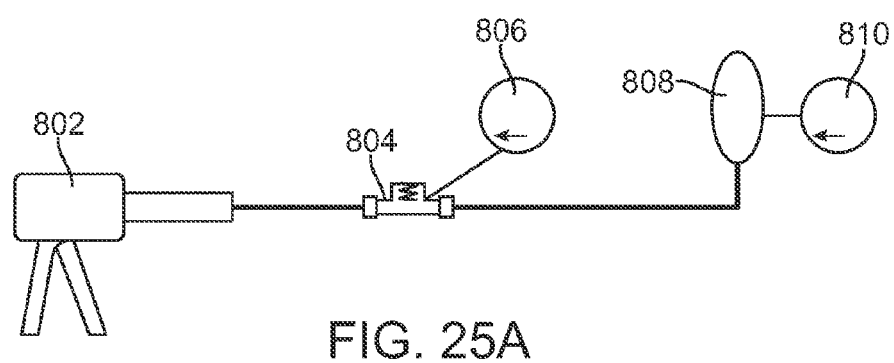
FIGS. 25A-25B illustrate the use of a pressure relief valve.
Figure 25B:
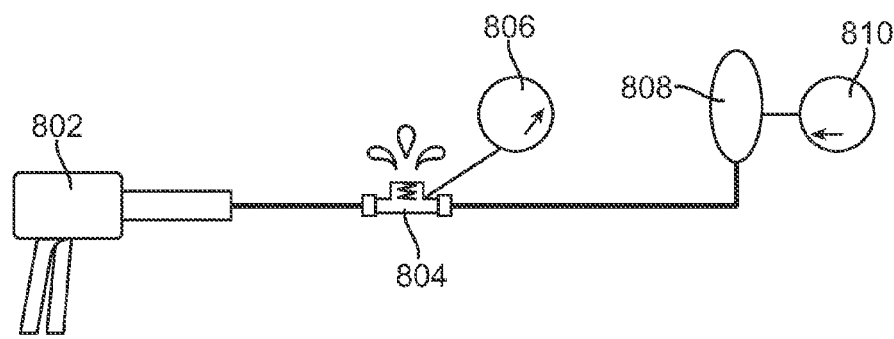
Figure 26A:
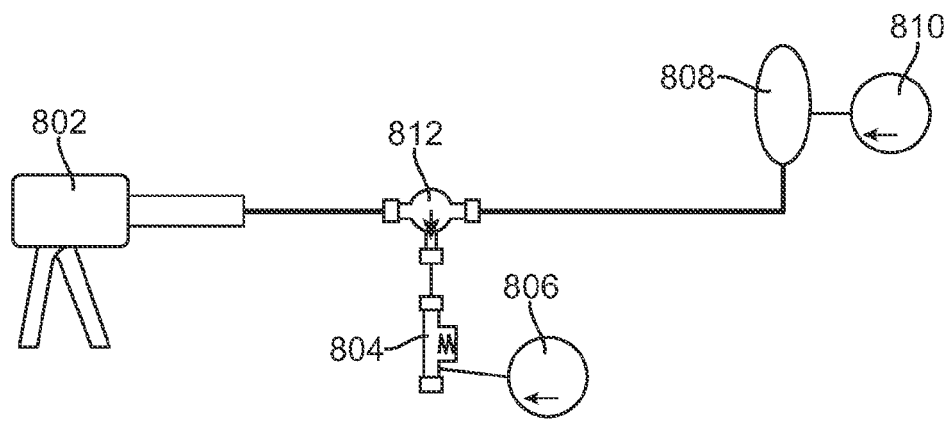
FIGS. 26A-26C show the use of a stopcock.
Figure 26B:
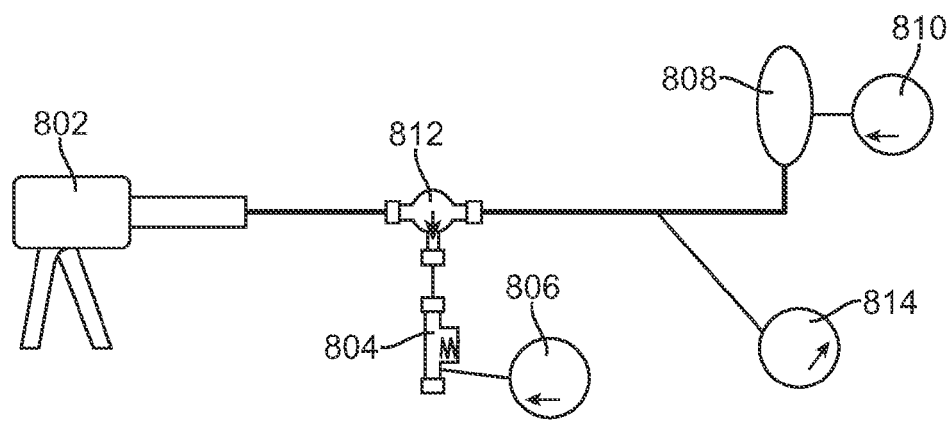
Figure 26C:
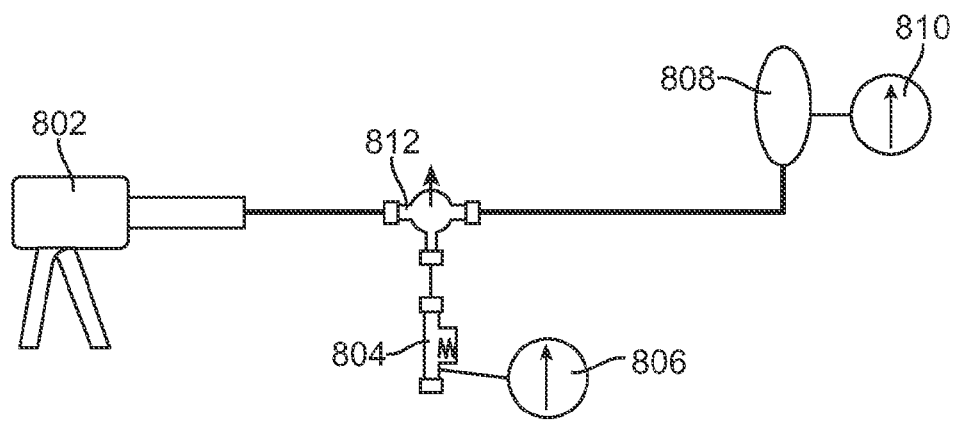

While the use of a pressure relief valve such as described with respect to FIGS. 14A-14C can be advantageous, it also can present challenges. For example, in FIG. 25A, a pressure relief valve 804 is placed in between a filling device 802 and the filling structure 808 with pressure gages 806, 810 positioned to monitor pressure at the pressure relief valve 804 and at the filling structure 808. Once the filling device 802 is actuated, pressure in the system will increase significantly which can trip the relief valve 804 into venting the excess pressure as seen in FIG. 25B before the filling structure is pressurized as seen in gage 810. Thus, it will be very difficult to fill the filling structure 808 since most of the filling material will be vented out of relief valve 804. FIGS. 26A-26C illustrate a potential solution for this challenge. In FIG. 26A, a four-way, 3 port stopcock 812 is placed in between the filling device 802 and the filling structure 808. Prior to actuating the filling device 802, stopcock 804 is adjusted so that flow is turned off to the pressure relief valve 804. Then, filling device 802 may be actuated and stopcock 804 may be adjusted to turn flow on in all directions. By turning the stopcock 804 off during actuation of filling device 802, the relief valve will not be exposed to pressure spikes, thereby preventing unwanted venting. FIG. 26A shows the stopcock adjusted to turn flow off to the pressure relief valve 804. FIG. 26B shows actuation of filling device 802 with the stopcock 812 still adjusted to stop flow to pressure relief valve 804. FIG. 26C shows stopcock 812 adjusted to allow flow in all directions. Pressure gages 806, 810 and 814 show relative pressure at various positions between filling device 802 and filling structure 808.

Some embodiments do not utilize a pressure relief valve and therefore other ways of masking the pressure line from pressure spikes are also desirable. For example, when an electronic pressure transducer is used, a low pass filter may be used to eliminate the pressure spike observed during actuation of the filling device. Additionally, electronic recording devices may be set to calculate and display the average pressure over a longer period of time (e.g. sample pressure over 20 seconds rather than 2 seconds), or sampling frequency may be reduced. This will effectively eliminate the pressure spike or "mask" it out and the resulting pressure display is a value that more closely indicates pressure of the filling structure. An exemplary embodiment of a pressure gage that masks pressure spikes is illustrated in FIGS. 51A-51B. In FIG. 51A, pressure measuring device 5104 includes an internal flexible membrane 5106 such that when high pressure fluid is delivered from a source such as syringe 5102, the membrane 5106 will compress and absorb some of the pressure, thereby masking any spikes. Once the membrane 5106 is pressed against the housing 5108, it cannot deform any further and thus higher pressures will not be transmitted to the gage as seen in FIG. 51B. One advantage of this type of pressure gage is that there are no static areas during pressurization and thus the hardenable filling medium cannot pool and obstruct flow.

Figure 15A:
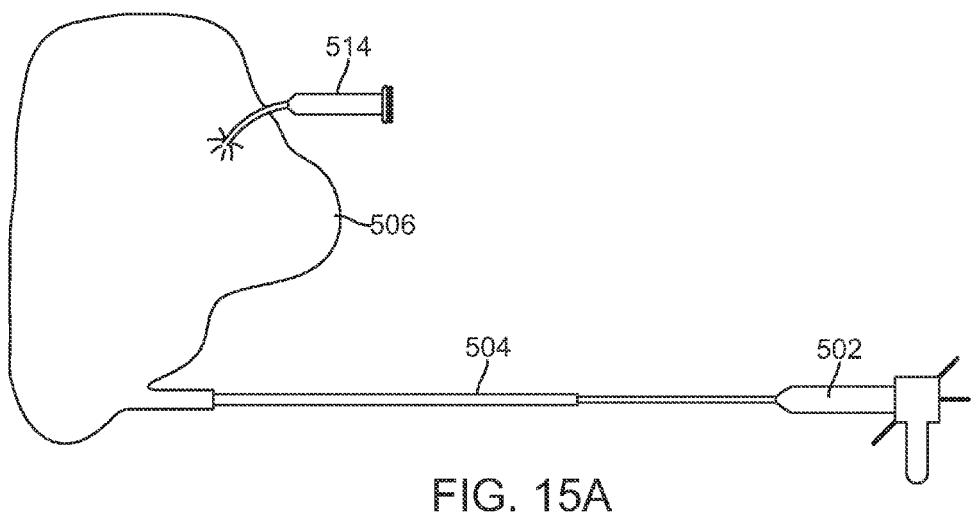
FIGS. 15A-15B illustrate use of another pressure indicator mechanism.
Figure 15B:
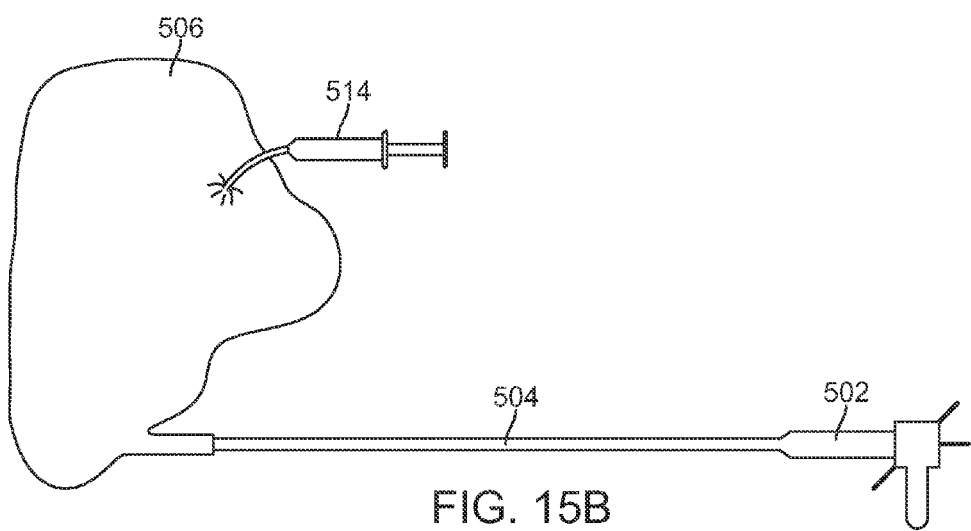

FIGS. 15A-15B illustrate still another visual indicator that may be used to control filling of the filling structure. In FIG. 15A, a filling device 502 is fluidly coupled to filling structure 506 via fluid line 504. A mechanical pressure indicator 514 is coupled with filling structure 506. The mechanical pressure indicator 514 has two positions, a first closed position as seen in FIG. 15A and a second open position see in FIG. 15B. The indicator springs open from the closed to opened position at a predetermined pressure value. The indicator is radiopaque and thus may be seen under fluoroscopy. Thus, when the indicator pops out, the operator knows that the filling structure 506 has reached a certain pressure and/or volume.

Figure 16A:
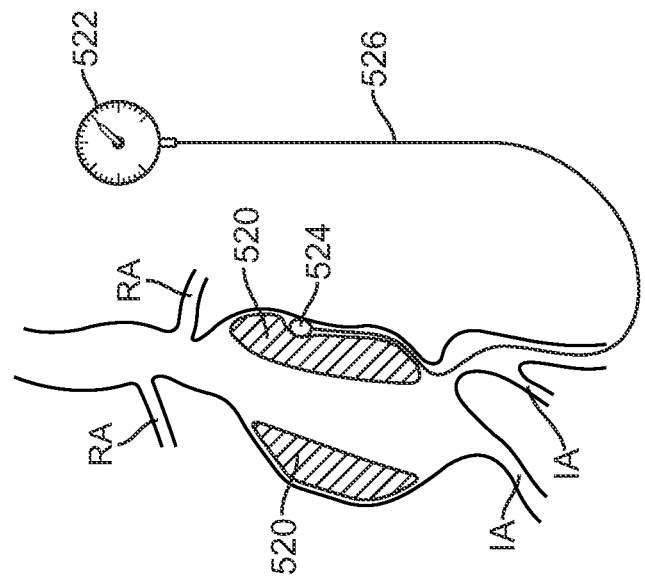
FIGS. 16A-16B illustrate pressure monitoring in the space between the filling structure and the aneurysm wall.
Figure 16B:
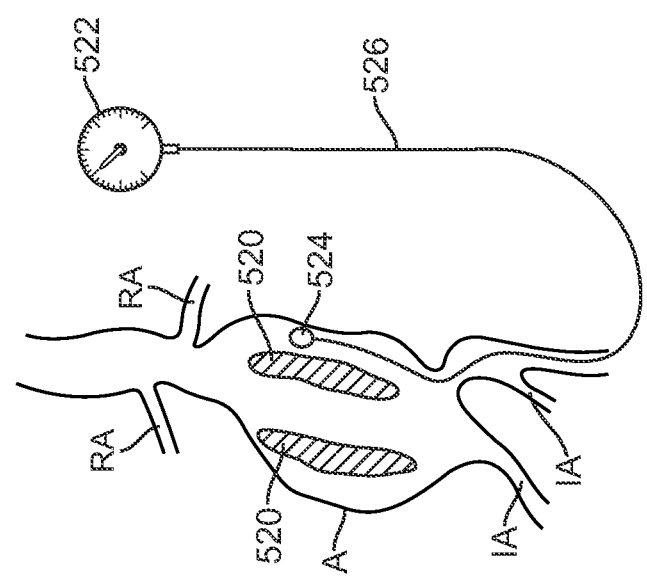

Placing a fluid filled balloon tipped catheter in the space between the filling structure and the aneurysm wall allows the pressure exerted by the filling structure against the aneurysm wall to be measured, and this is illustrated in FIGS. 16A-16B. In FIG. 16A, a partially filled, compliant balloon tipped catheter 524 is placed between an outer wall of filling structure 520 and an inner wall of the aneurysm A. The balloon catheter 524 may be deployed separately from or together with the filling structure deployment catheter. The balloon 524 may be filled with saline, carbon dioxide or like fluids. The catheter 524 is fluidly coupled with a pressure monitor such as gage 522 via a fluid line 526. At neutral fill volumes, the pressure of the blood is transmitted through the balloon 524, along fluid line 526 to pressure monitoring device 522, here a pressure gage. As the filling structure 520 is filled with a hardenable material, it will begin to press the balloon 524 against the aneurysm wall, squeezing it and thus exerting a higher pressure which is transmitted along fluid line 526 to pressure gage 522, as seen in FIG. 16B. Thus, an operator may continue to fill the filling structure 520 until gage 522 indicates a desired pressure, thereby demonstrating adequate contact between the filling structure 520 and aneurysm wall.

Figure 17A:
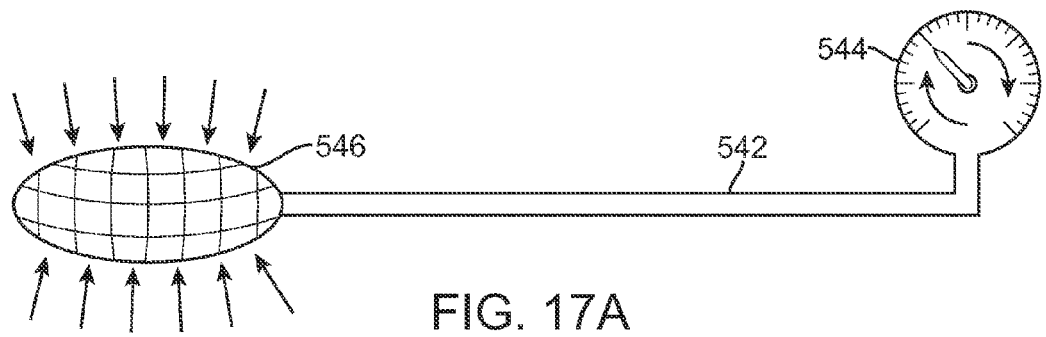
FIGS. 17A-17C show a balloon catheter having various pressure monitoring devices.
Figure 17B:
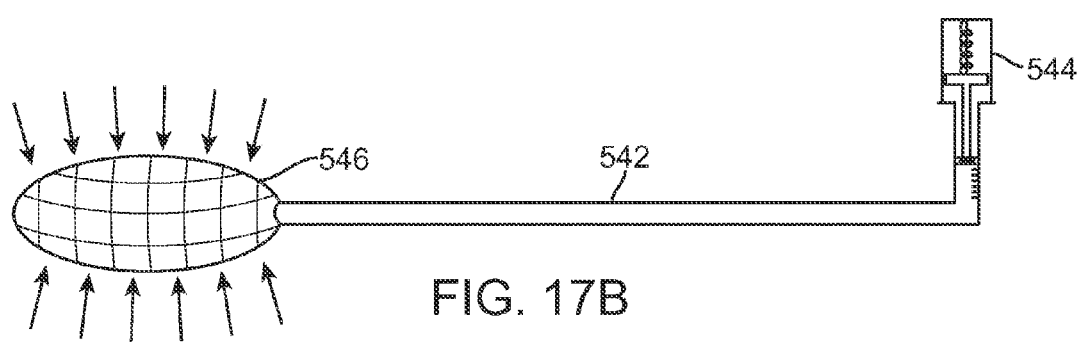
Figure 17C:
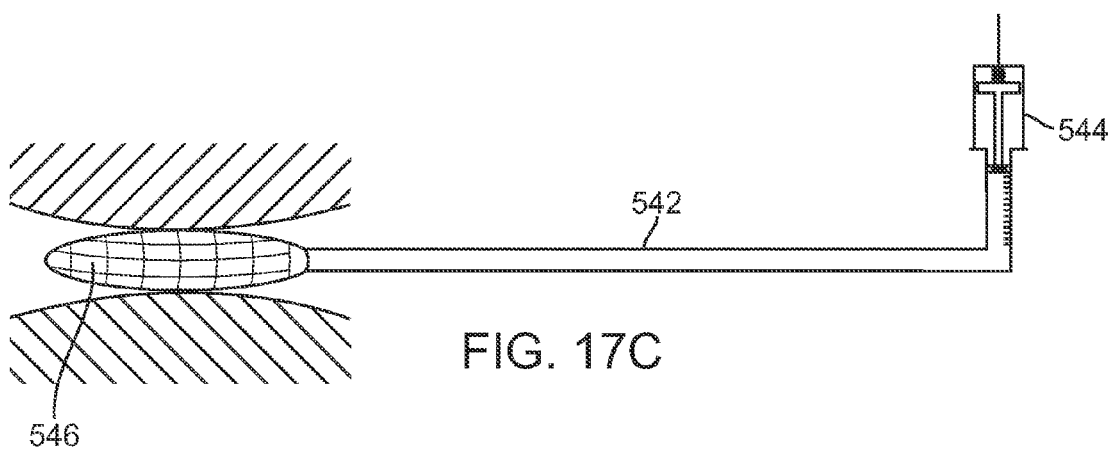

In addition to monitoring pressure of a balloon 524 placed between the filling structure and the aneurysm wall, other pressure indicators may be used to determine when to stop filling the filling structure. FIG. 17A shows how inwardly directed pressures exerted by an expanding filling structure and an aneurysm wall are directed against a balloon 546 coupled to pressure gage 544 via fluid line 542. This is similar to the embodiment previously discussed in FIGS. 16A-16B. However, in FIGS. 17B-17C, the pressure gage 544 is substituted with a spring loaded pressure indicator 544. Balloon 546 may be partially filled and preferably has a flat section that may be placed in the space between an outer wall of a filling structure and an inner wall of the aneurysm and is fabricated from a compliant material in order to provide accurate pressure feedback. As the filling structure expands and begins to compress the balloon 546 against the aneurysm wall, balloon 546 is compressed. The pressure transmitted by fluid line 542 to spring loaded pressure indicator 544 increases. However, the spring mechanism in indicator 544 resists the force until a predetermined value is reached. In FIG. 17C, once the predetermined value is exceeded, the spring collapses and a pin pops out of the indicator housing, alerting the user that the filling structure has been filled or that a desired pressure has been obtained. Different springs may be used in order to adjust the indicator to different pressure set points. In alternative embodiments, other compression mechanisms other than springs may be used.

Figure 18A:
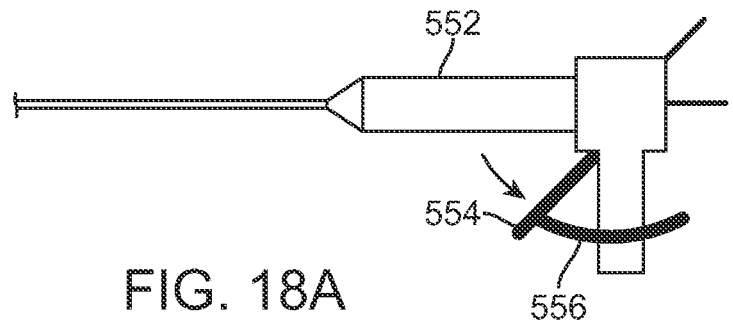
FIGS. 18A-18B illustrate a filling device with a locking mechanism.
Figure 18B:
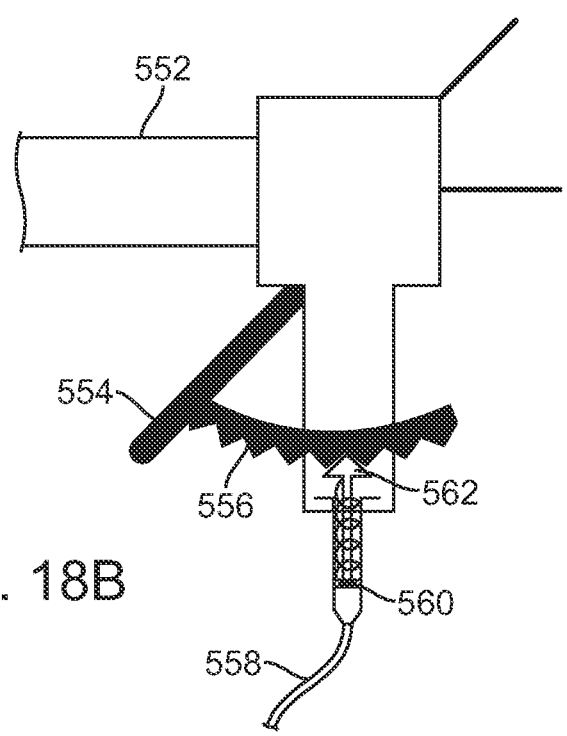

The balloon 546 and pressure indicator 544 may be integrated with a filling mechanism or the two may be separate from one another. FIGS. 18A-18B illustrate a combined filling mechanism with pressure indicator that serves as a lockout mechanism to prevent overfilling of the filling structure. In FIG. 18A, a gun-like filling device 552 comprises a handle 554 for actuating the filling device 552. As handle 554 is actuated by squeezing, filling material is discharged from a reservoir through a filling tube into the filling structure. A rack 556 having teeth is coupled with handle 554 to provide an operator with tactile feedback so that the operator knows how far handle 554 has been actuated. A locking mechanism 560 similar to the pressure indicator described above with respect to FIGS. 17A-17C is also coupled with filling device 552. In this embodiment, when pressure from fluid line 558 coupled to the filling structure or a balloon catheter exceeds a predetermined value, plunger 562 springs out of the locking mechanism 560 and engages one of the teeth on rack 556, thereby preventing further actuation of handle 554. Thus, filling mechanism 552 may be used to fill the filling structure but without overfilling it.

Figure 19A:
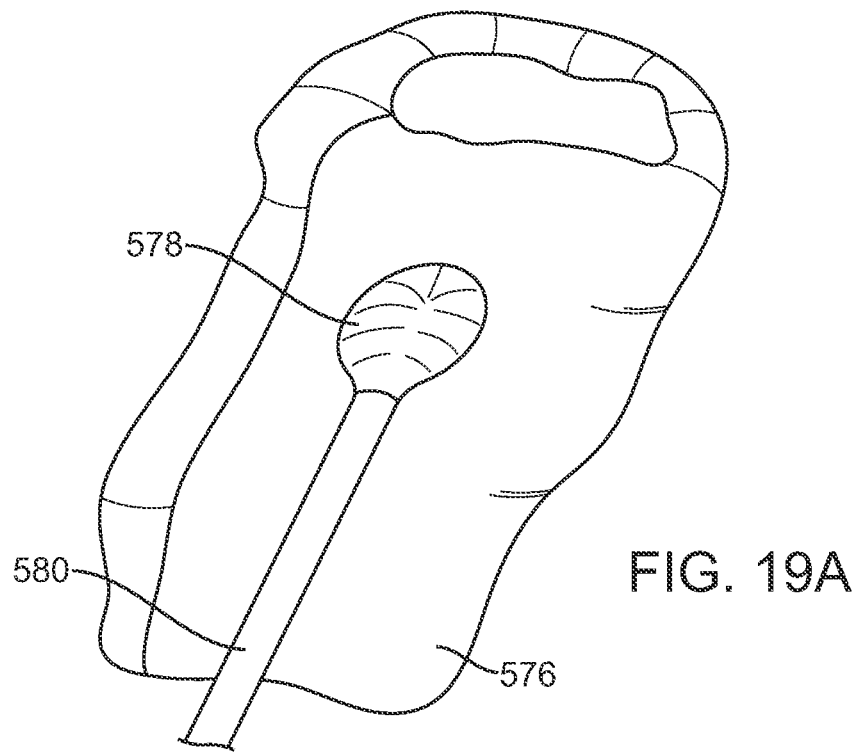
FIGS. 19A-19D illustrate various compartments in the filling structure.
Figure 19B:
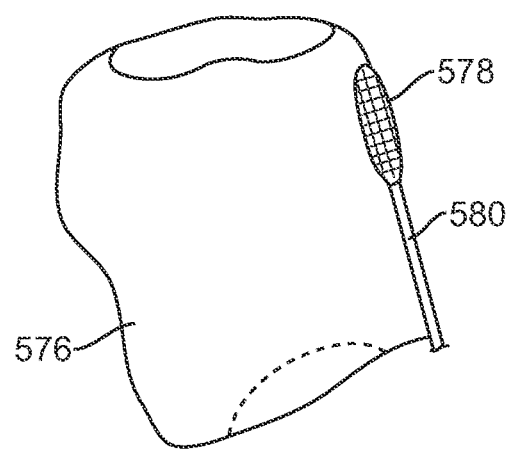

Instead of a separate balloon catheter placed between the filling structure and aneurysm wall, the filling structure may include a separate compartment that acts like the balloon catheter previously described in FIGS. 16A-16B. FIG. 19A illustrates a filling structure 576 having a separate compliant compartment 578. Compartment 578 may be pre-filled with a fluid such as saline or carbon dioxide. As filling structure 576 is filled and expands into the aneurysm wall, compartment 578 will be compressed and pressure therein will increase. Pressure in compartment 578 may be monitored via fluid line 580 by any number of methods including using a gage, a display or the like. This embodiment saves the operator from having to deliver a balloon catheter like that of FIGS. 16A-16B to the site of the aneurysm. FIG. 19B illustrates a side view of the embodiment in FIG. 19A.

Figure 19D:
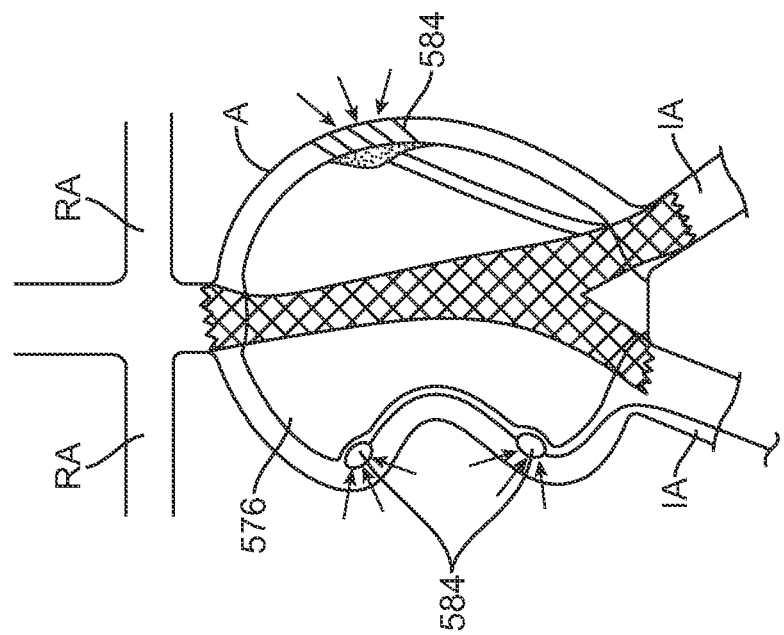
Figure 19C:
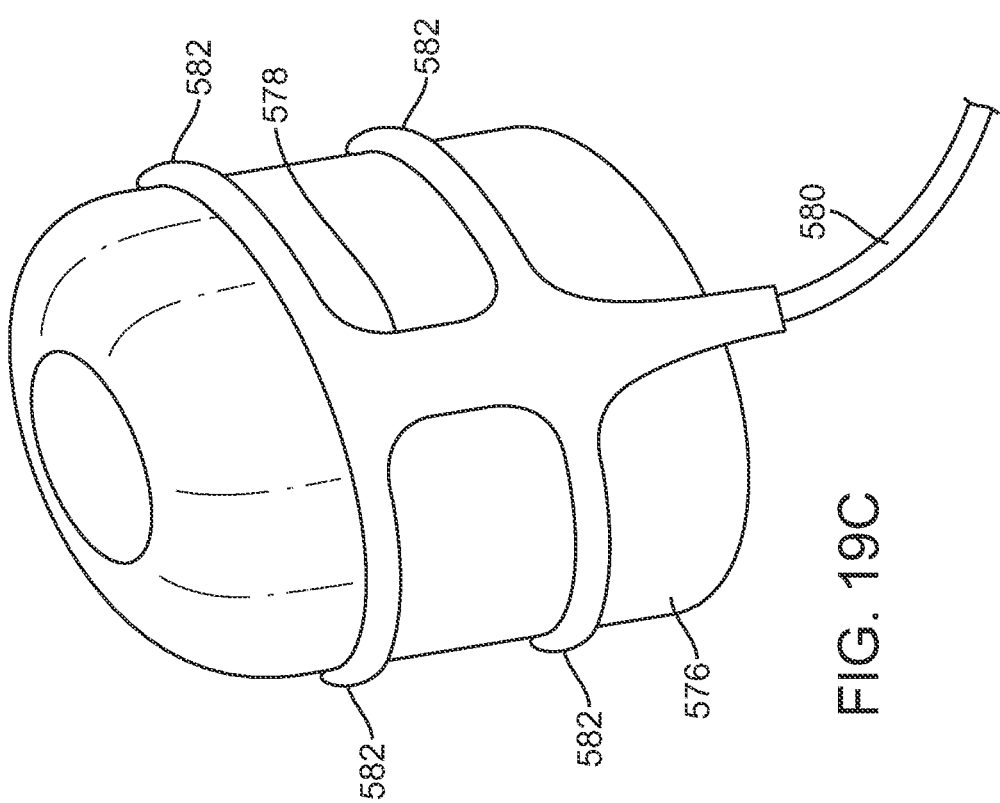

FIG. 19C illustrates how the filling structure 576 may include a compliant balloon-like member 578 for monitoring pressure between the filling structure and the aneurysm wall. In this embodiment, the balloon-like member 578 includes upper and lower arms 582 that circumferentially extend around all or a portion of the filling structure 576. The arms 582 allow contact between different parts of the filling structure to be monitored thereby preventing over inflation in one region and underinflation in another region. A fluid line 580 allows the balloon-like member 578 to be coupled with a pressure monitoring device. FIG. 19D illustrates still another embodiment of a filling structure having multiple separate compartments 584 located at several different points around filling structure 576. Similar to the embodiment of FIG. 19C, having multiple compartments allow filling of the filling structure to be assessed at several locations to ensure uniformity of filling. Each compartment may monitor pressure independently of the other compartments or they may be fluidly coupled together.

Figure 20A:
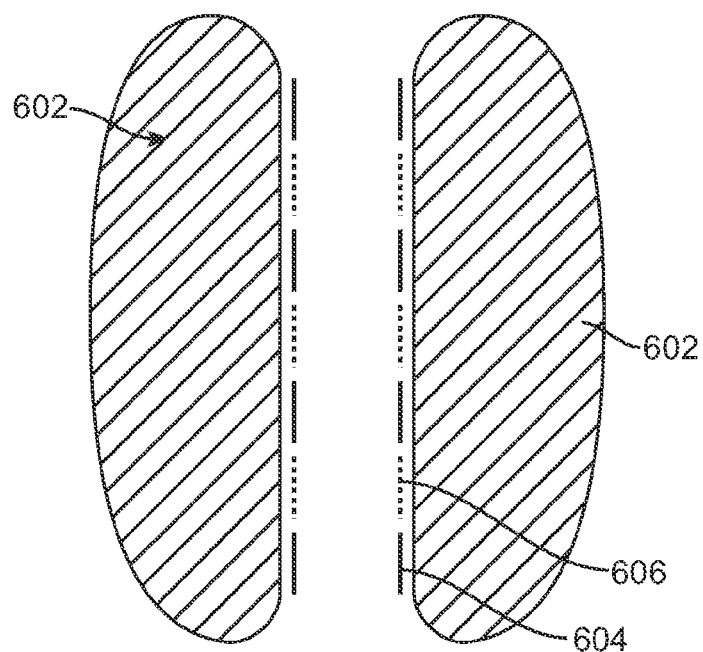
FIGS. 20A-20B illustrate the use of crumple zones in the scaffolding as pressure indicators.
Figure 20B:
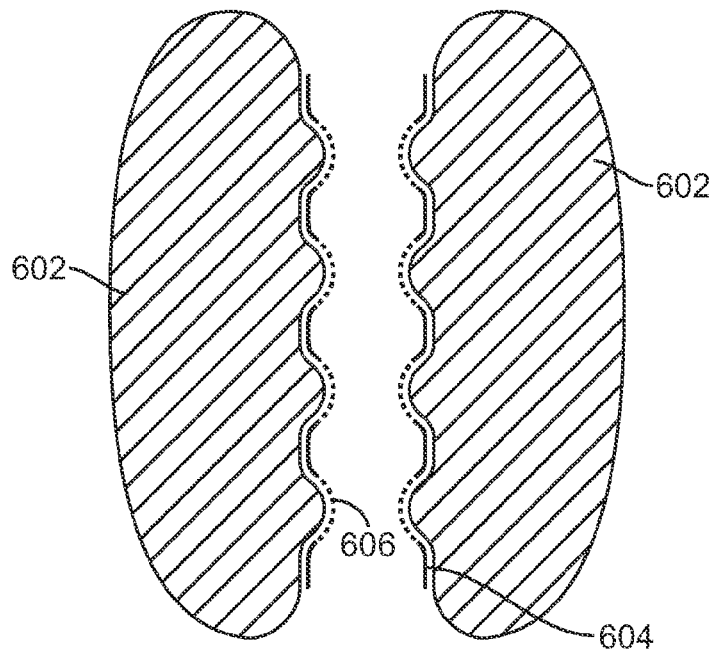

The scaffolding itself may also be used to indicate the filling status of the filling structure. In FIG. 20A, a filling structure is disposed over scaffold 604. Scaffold 604 has regions 606 which are designed to collapse at a lower radial pressure than the rest of the scaffold. Thus, when filling structure 602 is filled, it will exert a force against scaffold 604. The weakened regions 606 collapse inwardly slightly, without substantially occluding the lumen for blood flow, thereby forming a series of peaks and valleys which are visible under fluoroscopy. This is illustrated in FIG. 20B. An operator may therefore use this to monitor the extent of filling in the filling structure 602.

In still another embodiment, the balloon used to radially expand the scaffolding may also be used to monitor pressure. In FIG. 21, a delivery catheter 610 comprises an expandable balloon 618 disposed on a distal end of the catheter shaft and a scaffolding 614 is disposed thereover. Once the filling structure 616 is advanced into the aneurysm it may be filled. Balloon 618 is partially expanded into engagement with the filling structure 616. As the filling structure enlarges, it begins to compress the balloon 614. Catheter 610 transmits the pressure from balloon 616 to a pressure gage 612 so that the operator may monitor filling pressure. Thus, the operator may stop filling the filling structure when a predetermined pressure value is obtained. The scaffolding 614 may then be fully expanded either before, during or after filling the filling structure. The balloon 618 is then deflated and the delivery catheter 610 is removed from the aneurysm.

Other embodiments may control filling of the filling structures by using either a balloon on the delivery catheter or the filling structures themselves. For example, in FIGS. 27A-27B, two filling structures 852, 854 are positioned in the aneurysm AAA and partially filled with a filling device 862 to a predetermined volume or pressure. Balloons 856, 858 on a delivery catheter are inflated using an inflation device 860. As the balloons expand, the partially filled filling structures 852, 854 are pressed against the aneurysm walls, filling the aneurismal space and excess fluid is then forced out of the filling structures 852, 854 via a relief valve 868 seen in FIG. 27B. Scaffolds 864, 866 help maintain the lumen after the balloons 856, 858 are deflated.

FIGS. 28A-28B illustrate another embodiment where the filling structures themselves are used to help control their filling status. In FIG. 28A, two filling structures 852, 854 are positioned in the aneurysm AAA. A first filling structure 852 is at least partially filled. In FIG. 28B, the second filling structure 854 is filled so that it compresses filling structure 852. As filling structure 852 is compressed, excess fluid is vented from filling structure 852 via a pressure relief valve 868. This process is continued until the filling structures are essentially symmetrical with one another as may be observed under fluoroscopy.

While the above is a complete description of the preferred embodiments of the invention, various alternatives, modifications, and equivalents may be used. The various features of the embodiments disclosed herein may be combined or substituted with one another. Therefore, the above description should not be taken as limiting in scope of the invention which is defined by the appended claims.

The invention claimed is:

1. A system for treating an aneurysm in a blood vessel, the system comprising:
    an elongate flexible shaft having a proximal region and a distal region;
    a first double-walled filling structure disposed over the distal region of the shaft, the filling structure having an outer wall and an inner wall, wherein the filling structure is adapted to be filled with a hardenable fluid filing medium so that the outer wall conforms to an inside surface of the aneurysm and the inner wall forms a first substantially tubular lumen to provide a path for blood flow across the aneurysm;
    at least a first expandable scaffold disposed at least partly within the filling structure during delivery, the first scaffold radially expandable within at least a portion of the tubular lumen of the filling structure, wherein the first scaffold and the first double-walled filling structure are distinctly separate elements; and
    one or more tethers coupling the first scaffold to the first filling structure, wherein the one or more tethers are configured to limit axial movement of the first filling structure relative the first scaffold so that the first scaffold and the first filling structure remain concentric with each other along the first flexible shaft during delivery and deployment of the first scaffold and the first double-walled filling structure, wherein the one or more tethers comprise a first releasable coupling mechanism that limits axial movement of the first filling structure relative the first scaffold.

2. The system of claim 1, wherein the first releasable coupling mechanism comprises a thin flexible rod that traverses the first filling structure and has a distal-most portion that extends substantially parallel to a longitudinal axis of the filling structure and one or more guides attached to the first filling structure through which the rod extends.

3. The system of claim 2, wherein the one or more guides comprise one or more loops.

4. The system of claim 2, wherein the one or more guides comprise one or more eyelets.

5. The system of claim 2, wherein the one or more guides comprise at least a first guide near a distal end of the filling structure and a second guide near a proximal end of the filling structure such that when the thin flexible rod extends through the first and second guides during delivery, axial movement of the proximal end relative a distal end of the filling structure is inhibited.

6. The system of claim 2, wherein the rod comprises a lock wire or a tether.

7. The system of claim 2, wherein the thin flexible rod extends proximally outside the patient during delivery so as to allow proximal retraction of the thin rod to withdraw the thin flexible rod from the one or more guides to release the filling structure from the coupling mechanism.

8. The system of claim 7, wherein the thin flexible rod extends distal of the one or more guides to the distal region of the elongate rod.

9. The system of claim 8, wherein the thin flexible rod is releasably coupled with a distal nosecone dispose on a distal end of the elongate shaft.

10. The system of claim 9, wherein the distal nosecone includes an aperture through which the thin flexible rod extends.

11. The system of claim 2, wherein the thin flexible rod comprises a lock wire and the one or more guides comprises a loop, wherein the releasable coupling mechanism further includes a hollow post through which the lock wire extends that includes an aperture near a distal region thereof, wherein the loop extends around a portion of the lock wire exposed within the aperture during delivery of the filling structure.

12. The system of claim 1 further comprising:
    a second elongate flexible shaft having a proximal region and a distal region;
    a second double-walled filling structure disposed over the distal region of the second shaft, the filling structure having an outer wall and an inner wall, wherein the filling structure is adapted to be filled with a hardenable fluid filing medium so that the outer wall conforms to an inside surface of the aneurysm and the inner wall forms a first substantially tubular lumen to provide a path for blood flow across the aneurysm; and
    a second expandable scaffold disposed at least partly within the second filling structure during delivery, the second scaffold radially expandable within at least a portion of the tubular lumen of the second filling structure.

13. The system of claim 12, further comprising:
    a second releasable coupling mechanism that limits axial movement of the second filling structure relative the first scaffold such that the second scaffold and the second filling structure remain concentric with each other along the second flexible shaft during delivery and deployment of the second scaffold and second filling structure.

14. The system of claim 13, wherein the second releasable coupling mechanism comprises a second thin flexible rod that traverses the second filling structure and has a distal-most portion that extends substantially parallel to a longitudinal axis of the filling structure and one or more guides attached to the second filling structure through which the rod extends.

15. The system of claim 14, wherein the one or more guides comprise at least a first guide near a distal end of the filling structure and a second guide near a proximal end of the filling structure such that when the second rod extends through the first and second guides during delivery, axial movement of the proximal end relative a distal end of the filling structure is inhibited.

16. The system of claim 14, wherein the second rod extends proximally outside the patient during delivery so as to allow proximal retraction of the thin rod to withdraw the thin flexible rod from the one or more guides to release the filling structure from the coupling mechanism.

17. The system of claim 14, wherein the thin flexible rod comprises a lock wire and the one or more guides comprises a loop, wherein the releasable coupling mechanism further includes a hollow post through which the lock wire extends that includes an aperture near a distal region thereof, wherein the loop extends around a portion of the lock wire exposed within the aperture during delivery of the filling structure.

18. The system of claim 1, further comprising one or both of:

a pressure monitor, the pressure monitor coupled with the filling structure so as to permit pressure monitoring of the filling structure as the filling structure is filled with the hardenable fluid filling medium; and a visual indicator fluidly coupled therewith and having first and second positions, wherein the indicator moves from the first position to the second position when a predetermined pressure is applied to the visual indicator.

19. A system for treating an aneurysm in a blood vessel, the system comprising:

an elongate flexible shaft having a proximal region and a distal region;

a first double-walled filling structure disposed over the distal region of the shaft, the filling structure having an outer wall and an inner wall, wherein the filling structure is adapted to be filled with a hardenable fluid filling medium so that the outer wall conforms to an inside surface of the aneurysm and the inner wall forms a first substantially tubular lumen to provide a path for blood flow across the aneurysm;

at least a first expandable scaffold disposed at least partly within the filling structure during delivery, the first scaffold radially expandable within at least a portion of the tubular lumen of the filling structure, wherein the first scaffold and the first double-walled filling structure are distinctly separate elements;

a plurality of tether loops coupling the first scaffold to the first filling structure, the plurality of tether loops being distributed about a proximal end of each of the first filling structure and the first scaffold so as to limit axial movement of the first filling structure relative the first scaffold during delivery so that the first scaffold and the first filling structure remain concentric with each other during delivery and deployment; and a first releasable coupling mechanism configured to limit relative movement of the first double-walled filling structure and the first expandable scaffold and release from the elongate flexible shaft to facilitate delivery and deployment.

20. The system of claim 19, wherein the first releasable coupling mechanism comprises a first tether interfacing with a first tether loop attached to the first double-walled filling structure.

21. The system of claim 20, wherein the first releasable coupling mechanism further comprises a lockwire releasably coupled to the first tether.

* * * * *